(12) United States Patent
Reed et al.

(10) Patent No.: US 6,953,691 B2
(45) Date of Patent: Oct. 11, 2005

(54) NUCLEIC ACID MOLECULE ENCODING A PANG6 POLYPEPTIDE

(75) Inventors: John C Reed, San Diego, CA (US); Adam Godzik, San Diego, CA (US); Zhi-Liang Chu, San Diego, CA (US); Krzysztof Pawlowski, Malmo (SE); Loredana Fiorentino, San Diego, CA (US); Maria Eugenia Ariza, San Diego, CA (US); Christian Stehlik, San Diego, CA (US)

(73) Assignee: The Burnham Institute, La Jolla, CA (US)

(*) Notice: Subject to any disclaimer, the term of this patent is extended or adjusted under 35 U.S.C. 154(b) by 0 days.

(21) Appl. No.: 10/781,294

(22) Filed: Feb. 17, 2004

(65) Prior Publication Data

US 2004/0142374 A1 Jul. 22, 2004

Related U.S. Application Data

(63) Continuation of application No. 09/965,621, filed on Sep. 25, 2001, now abandoned.
(60) Provisional application No. 60/367,367, filed on Sep. 26, 2000, now abandoned.

(51) Int. Cl.[7] .............................. C12N 5/10; C12N 1/00; C12N 15/12; C12N 15/63
(52) U.S. Cl. ..................... 435/325; 435/320.1; 435/243; 435/419; 536/23.5
(58) Field of Search ............................ 536/23.5, 24.31; 435/320.1, 325, 419, 243

(56) References Cited

FOREIGN PATENT DOCUMENTS

WO    WO 01/61005    8/2001

OTHER PUBLICATIONS

NIH–MGC, National Institutes of Health, mammalian Gene Collection, Apr. 11, 2000, Database entry, Accession No. AW673661.*
Aderem et al., "Toll–like receptors in the induction of the innate immune responses," *Nature* 406:782–787 (2000).
Aravind et al., "The domains of death: evolution of the apoptosis machinery," *TIBS* 24(2):47–53 (1999).
Bertin and DiStefano, "The PYRIN domain: a novel motif found in apoptosis and inflammation proteins," *Cell Death and Differentiation* 7:1273–1274 (2000).
Beutler, "Autoimmunity and apoptosis: The Crohn's connection," *Immunity* 15:5–14 (2001).
Carpentier et al., "TRAF1 is a TNF inducible regulator of NF–κB activation," *FEBS Letters* 460:246–250 (1999).
Chu et al, "A novel enhancer of the Apaf1 apoptosome involved in cytochrome c–dependent caspase activation and apoptosis," *J. Biol. Chem.* 276:9239–9245 (2001).
Cohen et al., "IKAP is a scaffold protein of the IkappaB kinase complex," *Nature*, 395(6699):292–6 (1998).
Damiano et al., "CLAN, a novel human CED–4–like gene," *Genomics* 75:77–83(2001).
Dawson and Trapani, "The interferon–inducible autoantigen, IFI 16:localization to the nucleolus and identification of a DNA–binding domain," *Biochem Biophys. Res. Commun.* 214:152–162 (1995).
DeYoung et al., "Cloning a novel member of the human interferoninducible gene family associated with control of tumorigenicity in a model of human melanoma," *Oncogene* 15:453–457 (1997).
Fairbrother et al., "The PYRIN domain: a member of the death domain–fold superfamily," *Protein Science* 10:1911–1918 (2001).
French FMF Consortium, The "A candidate gene for familial Mediterranean fever," *Nature Genetics* 17:25–31 (1997).
Hayashi et al., "The innate immune response to bacterial flagellin is mediated by Toll–like receptor 5," *Nature* 410:1099–1103 (2001).
Hlaing et al., "Molecular cloning and characterization of DEFCAP–L and –S, two isoforms of a novel member of the mammalian Ced–4 family of apoptosis proteins," *J. Biol. Chem*, 276:9230–9238 (2001).
Inohara and Nunez, "Genes with homology to mammalian apoptosis regulators identified in zebrafish," *Cell Death and Differentiation* 7:509–510 (2000).
Inohara et al., "Nod1, an Apaf–1–like activator of caspase–9 and nuclear factor–6B," *J. Biol. Chem.* 274:14560–14567 (1999).
Johnstone et al., "The human interferon–inducible protein, IFI 16, is a repressor of transcription," *J. Biol. Chem.* 273:17172–17177 (1998).
Jones, "GenTHREADER: an efficient and reliable protein fold recognition method for genomic sequences," *J. Mol. Biol.* 287:797–815 (1999).

(Continued)

Primary Examiner—Terry McKelvey
(74) Attorney, Agent, or Firm—McDermott Will & Emery LLP

(57) ABSTRACT

The invention provides isolated nucleic acid molecules encoding PAAD-domain containing polypeptides and functional fragments thereof, including fragments containing PAAD domains, NB-ARC domains and LRR domains, encoded polypeptides, and antibodies. Also provided are methods of identifying polypeptides and agents that associate with a PAAD-domain containing polypeptide or fragment thereof, or that alter an association of a PAAD domain-containing polypeptides. Further provided are methods of identifying agents that modulate PAAD domain-mediated inhibition of NFκB activity, or modulate an activity of an NB-ARC domain of a PAAD domain-containing polypeptide. Also provided are methods of modulating NFκB transcriptional activity in a cell, and methods of altering expression of a PAAD domain-containing polypeptide in a cell.

4 Claims, 15 Drawing Sheets

OTHER PUBLICATIONS

Karin et al., "Phosphorylation meets ubiquitination: The control of NF–κB activity," *Ann. Rev. Immunol.* 18:621–663 (2000).

Karplus et al., "Hidden Markov models for detecting remote protein homologies," *Bioinformatics* 14(10):846–856 (1998).

Koonin and Aravind, "The NACHT family—a new group of predicted NTPases implicated in apoptosis and MHC transcription activation," *TIBS* 25(5):223–224 (2000).

Lawrence et al, "Detecting subtle sequence signals: a Gibbs sampling strategy for multiple alignment," *Science* 262:208–214 (1993).

Lee et al., "COP, a caspase recruitment domain–containing protein and inhibitor of caspase–1 activation processing," *J. Biol. Chem.* 276:34495–34500 (2001).

Lennon et al., "The I.M.A.G.E. consortium: an integrated molecular analysis of genomes and their expression," *Genomics* 33:151–152 (1996).

Martinon et al., "The pyrin domain: a possible member of the death domain–fold family implicated in apoptosis and inflammation," *Current Biology* 10(4):R118–R120 (2001).

Masumoto et al., "ASC, a novel 22–kDA protein, aggregates during apoptosis of human promyelocytic leukemia HL–60 cells," *J. Bio. Chem.* 274(48):33835–33838 (1999).

Masumoto et al., "Pyrin N–terminal homology domain– and caspase recruitment domain–dependent oligomerization of ASC," *Bichem. Biophys. Res. Commun.* 280(3):652–655 (2001).

Masumoto et al., "Murine ortholog of ASC, a CARD–containing protein, self–associates and exhibits restricted distribution in developing mouse embryos," *Exp. Cell Res.* 262(2):128–133 (2001).

Pawlowski et al., "PAAD—a new protein domain associated with apoptosis, cancer and autoimmune diseases," *TIBS* 26(2):85–87 (2001).

Pras, "Familial mediterranean fever: from the clinical syndrome to the cloning of the pyrin gene," *Scand J. Rheumatol,* 27:92–97 (1998).

Reed et al., "A strategy for generating monoclonal antibodies against recombinant baculovirus–produced proteins: application to the Bcl–2 oncoprotein," *Anal Biochem.* 205(1):70–6 (1992).

Rost et al., "PHD—an automatic mall server for protein secondary structure prediction," *CABIOS* 10:53–60 (1994).

Ruiz–Opazo et al., "Identification of a novel dual angiotensin II/vasopressin receptor on the basis of molecular recognition theory," *Nature Med.* 1:1074–1081 (1995).

Rychiewski et al., "Comparison of sequence profiles. Strategies for structural predictions using sequence information," *Protein Science* 9:232–241 (2000).

Sali and Blundell, "Comparative protein modelling by satisfaction of spatial restraints," *J. Mol. Biol.* 234:779–815 (1993).

Staub et al., "The DAPIN family: a novel domain links apoptotic and interferon response proteins," *TIBS* 26(2): 83–85 (2001).

Takeuchi et al., "TLR6: A novel member of an expanding Toll–like receptor family," *Gene* 231:59–65 (1999).

Tao et al., "Bcl–xS and Bad potentiate the death suppressing activities of Bcl–xL, Bcl–2, and A1 in yeast," *J. Biol Chem.* 273(37):23704–8 (1998).

Thompson et al., "Clustal W: improving the sensitivity of progressive multiple sequence alignment through sequence weighting, position–specific gap penalties and weight matrix choice," *Nucleic Acids Research* 22 (22):4673–4680 (1994).

van der Biezen and Jones, "The NB–ARC domain: a novel signalling motif shared by plant resistance gene products and regulators of cell death in animals," *Curr. Biol.* 8:R226–R227 (1998).

Xie et al., "MNDA dimerizes through a complex motif involving an Nterminal basic region," *FEBS Letters* 408:151–155 (1997).

* cited by examiner

FIGURE 1

ASC

PAN1 - PAN6 (only some contain leucine rich repeats - LRR)

NAC zebrafish caspase pyrin

IFI16,

AIM2, MNDA

ASC2

SEQUENCE LISTING

```
<160> NUMBER OF SEQ ID NOS: 64

<210> SEQ ID NO 1
<211> LENGTH: 76
<212> TYPE: PRT
<213> ORGANISM: Homo sapien

<400> SEQUENCE: 1

Leu Leu Glu Gln Leu Ser Gln Asp Glu Leu Ser Lys Phe Lys Tyr Leu
1               5                   10                  15

Ile Thr Thr Phe Ser Leu Ala His Glu Leu Gln Lys Ile Pro His Lys
            20                  25                  30

Glu Val Asp Lys Ala Asp Gly Lys Gln Leu Val Glu Ile Leu Thr Thr
        35                  40                  45

His Cys Asp Ser Tyr Trp Val Glu Met Ala Ser Leu Gln Val Phe Glu
    50                  55                  60

Lys Met His Arg Met Asp Leu Ser Glu Arg Ala Lys
65                  70                  75
```

<210> SEQ ID NO 2
<211> LENGTH: 76
<212> TYPE: PRT
<213> ORGANISM: Homo sapien

<400> SEQUENCE: 2

Tyr Leu Glu Glu Leu Lys Lys Glu Glu Phe Arg Lys Phe Lys Glu His
 1               5                  10                  15

Leu Lys Gln Met Thr Leu Gln Leu Glu Leu Lys Gln Ile Pro Trp Thr
                20                  25                  30

Glu Val Lys Lys Ala Ser Arg Glu Glu Leu Ala Asn Leu Leu Ile Lys
            35                  40                  45

His Tyr Glu Glu Gln Gln Ala Trp Asn Ile Thr Leu Arg Ile Phe Gln
        50                  55                  60

Lys Met Asp Arg Lys Asp Leu Cys Met Lys Val Met
65                  70                  75

<210> SEQ ID NO 3
<211> LENGTH: 73
<212> TYPE: PRT
<213> ORGANISM: Homo sapien

<400> SEQUENCE: 3

Ala Leu Glu Glu Leu Ser Gln Glu Gln Leu Lys Arg Phe Arg His Lys
 1               5                  10                  15

Leu Arg Asp Val Gly Pro Asp Gly Arg Ser Ile Pro Trp Gly Arg Leu
                20                  25                  30

Glu Arg Ala Asp Ala Val Asp Leu Ala Glu Gln Leu Ala Gln Phe Tyr
            35                  40                  45

Gly Pro Glu Pro Ala Leu Glu Val Ala Arg Lys Thr Leu Lys Arg Ala
        50                  55                  60

Asp Ala Arg Asp Val Ala Ala Gln Leu
65                  70

<210> SEQ ID NO 4
<211> LENGTH: 75
<212> TYPE: PRT
<213> ORGANISM: Homo sapien

<400> SEQUENCE: 4

Tyr Met Arg Asn Val Ser His Glu Glu Leu Gln Arg Phe Lys Gln Leu
 1               5                  10                  15

Leu Leu Thr Glu Leu Ser Thr Gly Thr Met Pro Ile Thr Trp Asp Gln
                20                  25                  30

Val Glu Thr Ala Ser Trp Ala Glu Val Val His Leu Leu Ile Glu Arg
            35                  40                  45

Phe Pro Gly Arg Arg Ala Trp Asp Val Thr Ser Asn Ile Phe Ala Ile
        50                  55                  60

Met Asn Cys Asp Lys Met Cys Val Val Val Arg
65                  70                  75

<210> SEQ ID NO 5
<211> LENGTH: 76
<212> TYPE: PRT
<213> ORGANISM: Homo sapien

```
<400> SEQUENCE: 5

Ala Leu Ser Asp Leu Glu Glu Asn Asp Phe Lys Lys Leu Lys Phe Tyr
 1               5                  10                  15

Leu Arg Asp Met Thr Leu Ser Glu Gly Gln Pro Pro Leu Ala Arg Gly
             20                  25                  30

Glu Leu Glu Gly Leu Ile Pro Val Asp Leu Ala Glu Leu Leu Ile Ser
         35                  40                  45

Lys Tyr Gly Glu Lys Glu Ala Val Lys Val Val Leu Lys Gly Leu Lys
     50                  55                  60

Val Met Asn Leu Glu Leu Val Asp Gln Leu Ser
 65              70                  75

<210> SEQ ID NO 6
<211> LENGTH: 75
<212> TYPE: PRT
<213> ORGANISM: Homo sapien

<400> SEQUENCE: 6

Tyr Leu Glu Glu Leu Glu Ala Val Glu Leu Lys Lys Phe Lys Leu Tyr
 1               5                  10                  15

Leu Gly Thr Ala Thr Glu Leu Gly Glu Gly Lys Ile Pro Trp Gly Ser
             20                  25                  30

Met Glu Lys Ala Gly Pro Leu Glu Met Ala Gln Leu Leu Ile Thr His
         35                  40                  45

Phe Gly Pro Glu Glu Ala Trp Arg Leu Ala Leu Ser Thr Phe Glu Arg
     50                  55                  60

Ile Asn Arg Lys Asp Leu Trp Glu Arg Gly Gln
 65              70                  75

<210> SEQ ID NO 7
<211> LENGTH: 76
<212> TYPE: PRT
<213> ORGANISM: Homo sapien

<400> SEQUENCE: 7

Thr Leu Glu Glu Leu Val Pro Tyr Asp Phe Glu Lys Phe Lys Phe Lys
 1               5                  10                  15

Leu Gln Asn Thr Ser Val Gln Lys Glu His Ser Arg Ile Pro Arg Ser
             20                  25                  30

Gln Ile Gln Arg Ala Arg Pro Val Lys Met Ala Thr Leu Leu Val Thr
         35                  40                  45

Tyr Tyr Gly Glu Glu Tyr Ala Val Gln Leu Thr Leu Gln Val Leu Arg
     50                  55                  60

Ala Ile Asn Gln Arg Leu Leu Ala Glu Glu Leu His
 65              70                  75

<210> SEQ ID NO 8
<211> LENGTH: 71
<212> TYPE: PRT
<213> ORGANISM: Homo sapien

<400> SEQUENCE: 8

Tyr Leu Glu Asp Leu Glu Asp Val Asp Leu Lys Lys Phe Lys Met His
 1               5                  10                  15

Leu Glu Asp Tyr Pro Pro Gln Lys Gly Cys Ile Pro Leu Pro Arg Gly
             20                  25                  30

Gln Thr Glu Lys Ala Asp His Val Asp Leu Ala Thr Leu Met Ile Asp
         35                  40                  45
```

```
Phe Asn Gly Glu Glu Lys Ala Trp Ala Met Val Val Trp Ile Phe Ala
    50                  55                  60

Ala Ile Asn Arg Arg Asp Leu
65                  70

<210> SEQ ID NO 9
<211> LENGTH: 76
<212> TYPE: PRT
<213> ORGANISM: Homo sapien

<400> SEQUENCE: 9

Ala Leu Glu Asn Leu Thr Ala Glu Glu Leu Lys Lys Phe Lys Leu Lys
 1               5                  10                  15

Leu Leu Ser Val Pro Leu Arg Glu Gly Tyr Gly Arg Ile Pro Arg Gly
                20                  25                  30

Ala Leu Leu Pro Met Asp Ala Leu Asp Leu Thr Asp Lys Leu Val Ser
            35                  40                  45

Phe Tyr Leu Glu Thr Tyr Gly Ala Glu Leu Thr Ala Asn Val Leu Arg
    50                  55                  60

Asp Met Gly Leu Gln Glu Met Ala Gly Gln Leu Gln
65                  70                  75

<210> SEQ ID NO 10
<211> LENGTH: 76
<212> TYPE: PRT
<213> ORGANISM: Homo sapien

<400> SEQUENCE: 10

Val Leu Glu Asn Leu Thr Pro Glu Glu Leu Lys Lys Phe Lys Met Lys
 1               5                  10                  15

Leu Gly Thr Val Pro Leu Arg Glu Gly Phe Glu Arg Ile Pro Arg Gly
                20                  25                  30

Ala Leu Gly Gln Leu Asp Ile Val Asp Leu Thr Asp Lys Leu Val Ala
            35                  40                  45

Ser Tyr Tyr Glu Asp Tyr Ala Ala Glu Leu Val Val Ala Val Leu Arg
    50                  55                  60

Asp Met Arg Met Leu Glu Glu Ala Ala Arg Leu Gln
65                  70                  75

<210> SEQ ID NO 11
<211> LENGTH: 76
<212> TYPE: PRT
<213> ORGANISM: Homo sapien

<400> SEQUENCE: 11

Tyr Leu Glu Phe Leu Lys Lys Glu Glu Leu Lys Glu Phe Gln Leu Leu
 1               5                  10                  15

Leu Ala Asn Lys Ala His Ser Arg Ser Ser Ser Gly Glu Thr Pro Ala
                20                  25                  30

Gln Pro Glu Lys Thr Ser Gly Met Glu Val Ala Ser Tyr Leu Val Ala
            35                  40                  45

Gln Tyr Gly Glu Gln Arg Ala Trp Asp Leu Ala Leu His Thr Trp Glu
    50                  55                  60

Gln Met Gly Leu Arg Ser Leu Cys Ala Gln Ala Gln
65                  70                  75
```

-continued

```
<210> SEQ ID NO 12
<211> LENGTH: 70
<212> TYPE: PRT
<213> ORGANISM: Homo sapien

<400> SEQUENCE: 12

Gly Leu Asp Asn Ile Thr Asp Glu Glu Leu Asp Arg Phe Lys Phe Phe
 1               5                  10                  15

Leu Ser Asp Glu Phe Asn Ile Ala Thr Gly Lys Leu His Thr Ala Asn
            20                  25                  30

Arg Ile Gln Val Ala Thr Leu Met Ile Gln Asn Ala Gly Ala Val Ser
        35                  40                  45

Ala Val Met Lys Thr Ile Arg Ile Phe Gln Lys Leu Asn Tyr Met Leu
    50                  55                  60

Leu Ala Lys Arg Leu Gln
65                  70

<210> SEQ ID NO 13
<211> LENGTH: 71
<212> TYPE: PRT
<213> ORGANISM: Homo sapien

<400> SEQUENCE: 13

Gly Leu Glu Val Ile Asn Asp Tyr His Phe Arg Met Val Lys Ser Leu
 1               5                  10                  15

Leu Ser Asn Asp Leu Lys Leu Asn Leu Lys Met Arg Glu Glu Tyr Asp
            20                  25                  30

Lys Ile Gln Ile Ala Asp Leu Met Glu Glu Lys Phe Arg Gly Asp Ala
        35                  40                  45

Gly Leu Gly Lys Leu Ile Lys Ile Phe Glu Asp Ile Pro Thr Leu Glu
    50                  55                  60

Asp Leu Ala Glu Thr Leu Lys
65                  70

<210> SEQ ID NO 14
<211> LENGTH: 70
<212> TYPE: PRT
<213> ORGANISM: Myxoma virus

<400> SEQUENCE: 14

Val Leu Glu Asn Leu Ser Asp Tyr Gln Phe Lys Met Phe Ile Tyr Leu
 1               5                  10                  15

Ala Met Glu Asp Leu Tyr Ile Glu Arg Ala Glu Lys Glu Lys Ile Asp
            20                  25                  30

Arg Ile Asp Leu Ala His Lys Ile Ser Glu Gln Tyr Leu Gly Thr Asp
        35                  40                  45

Tyr Ile Glu Phe Met Lys Arg Val Thr Asp Phe Ile Pro Asn Lys Val
    50                  55                  60

Tyr Val Asp Ser Leu Leu
65                  70

<210> SEQ ID NO 15
<211> LENGTH: 2985
<212> TYPE: DNA
<213> ORGANISM: Homo sapien
<220> FEATURE:
<221> NAME/KEY: CDS
<222> LOCATION: (1)...(2985)
```

-continued

```
<220> FEATURE:
<221> NAME/KEY: misc_feature
<222> LOCATION: (1)...(1857)
<223> OTHER INFORMATION: n = A,T,C or G

<400> SEQUENCE: 15 atg gca gcc tct ttc ttc tct gat ttt ggt ctt atg tgg tat ctg gag        48
Met Ala Ala Ser Phe Phe Ser Asp Phe Gly Leu Met Trp Tyr Leu Glu
 1               5                  10                  15 gag ctc aaa aag gag gag ttc agg aaa ttt aaa gaa cat ctc aag caa        96
Glu Leu Lys Lys Glu Glu Phe Arg Lys Phe Lys Glu His Leu Lys Gln
            20                  25                  30 atg act ttg cag ctt gaa ctc aag cag att ccc tgg act gag gtc aaa       144
Met Thr Leu Gln Leu Glu Leu Lys Gln Ile Pro Trp Thr Glu Val Lys
        35                  40                  45 aaa gca tcc cgg gaa gaa ctt gca aac ctc ttg atc aag cac tat gaa       192
Lys Ala Ser Arg Glu Glu Leu Ala Asn Leu Leu Ile Lys His Tyr Glu
    50                  55                  60 gaa caa caa gct tgg aac ata acc tta aga atc ttt caa aag atg gat       240
Glu Gln Gln Ala Trp Asn Ile Thr Leu Arg Ile Phe Gln Lys Met Asp
65                  70                  75                  80 aga aag gat ctc tgc atg aag gtc atg agg gag aga aca gga tac aca       288
Arg Lys Asp Leu Cys Met Lys Val Met Arg Glu Arg Thr Gly Tyr Thr
                85                  90                  95 aag acc tat caa gct cac gca aag cag aaa ttc agc cgc tta tgg tcc       336
Lys Thr Tyr Gln Ala His Ala Lys Gln Lys Phe Ser Arg Leu Trp Ser
            100                 105                 110 agc aag tct gtc act gag att cac cta tac ttt gag gag gaa gtc aag       384
Ser Lys Ser Val Thr Glu Ile His Leu Tyr Phe Glu Glu Glu Val Lys
        115                 120                 125 caa gaa gaa tgt gac cat ttg gac cgc ctt ttt gct ccc aag gaa act       432
Gln Glu Glu Cys Asp His Leu Asp Arg Leu Phe Ala Pro Lys Glu Thr
    130                 135                 140 ggg aaa cag cca cgt aca gtg att att caa gga cca caa gga att gga       480
Gly Lys Gln Pro Arg Thr Val Ile Ile Gln Gly Pro Gln Gly Ile Gly
145                 150                 155                 160 aaa acg aca ctc ctg atg aag ctg atg atg gcc tgg tcg gac aac aag       528
Lys Thr Thr Leu Leu Met Lys Leu Met Met Ala Trp Ser Asp Asn Lys
                165                 170                 175 atc ttt cgg gat agg ttc ctg tac acg ttc tat ttc tgc tgc aga gaa       576
Ile Phe Arg Asp Arg Phe Leu Tyr Thr Phe Tyr Phe Cys Cys Arg Glu
            180                 185                 190 ctg agg gag ttg ccg cca acg agt ttg gct gac ttg att tcc aga gag       624
Leu Arg Glu Leu Pro Pro Thr Ser Leu Ala Asp Leu Ile Ser Arg Glu
        195                 200                 205 tgg cct gac ccc gct gct cct ata aca gag atc gtg tct caa ccg gag       672
Trp Pro Asp Pro Ala Ala Pro Ile Thr Glu Ile Val Ser Gln Pro Glu
    210                 215                 220 aga ctc ttg ttc gtc atc gac agc ttc gaa gag ctg cag ggc ggc ttg       720
Arg Leu Leu Phe Val Ile Asp Ser Phe Glu Glu Leu Gln Gly Gly Leu
225                 230                 235                 240 aac gaa ccc gat tcg gat ctg tgt ggt gac ttg atg gag aaa cgg ccg       768
Asn Glu Pro Asp Ser Asp Leu Cys Gly Asp Leu Met Glu Lys Arg Pro
                245                 250                 255 gtg cag gtg ctt ctg agc agt ttg ctg agg aag aag atg ctc ccg gag       816
Val Gln Val Leu Leu Ser Ser Leu Leu Arg Lys Lys Met Leu Pro Glu
            260                 265                 270 gcc tcc ctg ctc atc gcc atc aaa ccc gtg tgc ccg aag gag ctc cgg       864
Ala Ser Leu Leu Ile Ala Ile Lys Pro Val Cys Pro Lys Glu Leu Arg
        275                 280                 285
```

```
gat cag gtg acg atc tca gaa atc tac cag ccc cgg gga ttc aac gag      912
Asp Gln Val Thr Ile Ser Glu Ile Tyr Gln Pro Arg Gly Phe Asn Glu
    290                 295                 300 agt gat agg tta gtg tat ttc tgc tgt ttc ttc aaa gac ccg aaa aga      960
Ser Asp Arg Leu Val Tyr Phe Cys Cys Phe Phe Lys Asp Pro Lys Arg
305                 310                 315                 320 gcc atg gaa gcc ttc aat ctt gta aga gaa agt gaa cag ctg ttt tcc     1008
Ala Met Glu Ala Phe Asn Leu Val Arg Glu Ser Glu Gln Leu Phe Ser
                325                 330                 335 ata tgc caa atc ccg ctc ctc tgc tgg atc ctg tgt acc agt ctg aag     1056
Ile Cys Gln Ile Pro Leu Leu Cys Trp Ile Leu Cys Thr Ser Leu Lys
    340                 345                 350 caa gag atg cag aaa gga aaa gac ctg gcc ctg acc tgc cag agc act     1104
Gln Glu Met Gln Lys Gly Lys Asp Leu Ala Leu Thr Cys Gln Ser Thr
355                 360                 365 acc tct gtg tac tcc tct ttc gtc ttt aac ctg ttc aca cct gag ggt     1152
Thr Ser Val Tyr Ser Ser Phe Val Phe Asn Leu Phe Thr Pro Glu Gly
                370                 375                 380 gcc gag ggc ccg act ccg caa acc cag cac cag ctg aag gcc ctg tgc     1200
Ala Glu Gly Pro Thr Pro Gln Thr Gln His Gln Leu Lys Ala Leu Cys
385                 390                 395                 400 tcc ctg gct gca gag ggt atg tgg aca gac aca ttt gag ttt tgt gaa     1248
Ser Leu Ala Ala Glu Gly Met Trp Thr Asp Thr Phe Glu Phe Cys Glu
                405                 410                 415 gac gac ctc cgg aga aat ggg gtt gtt gac gct gac atc cct gcg ctg     1296
Asp Asp Leu Arg Arg Asn Gly Val Val Asp Ala Asp Ile Pro Ala Leu
                420                 425                 430 ctg ggc acc aag ata ctt ctg aag tac ggg gag cgt gag agc tcc tac     1344
Leu Gly Thr Lys Ile Leu Leu Lys Tyr Gly Glu Arg Glu Ser Ser Tyr
            435                 440                 445 gtg ttc ctc cac gtg tgt atc cag gag ttc tgt gcc gcc ttg ttc tat     1392
Val Phe Leu His Val Cys Ile Gln Glu Phe Cys Ala Ala Leu Phe Tyr
450                 455                 460 ttg ctc aag agc cat ctt gat cat cct cac cca gct gtg aga tgt gta     1440
Leu Leu Lys Ser His Leu Asp His Pro His Pro Ala Val Arg Cys Val
465                 470                 475                 480 cag gaa ttg cta gtt gcc aat ttt gaa aaa gca agg aga gca cat tgg     1488
Gln Glu Leu Leu Val Ala Asn Phe Glu Lys Ala Arg Arg Ala His Trp
                485                 490                 495 att ttt ttg ggg tgt ttt cta act ggc ctt tta aat aaa aag gaa caa     1536
Ile Phe Leu Gly Cys Phe Leu Thr Gly Leu Leu Asn Lys Lys Glu Gln
                500                 505                 510 gaa aaa ctg gat gcg ttt ttt ggc ttc caa ctg tcc caa gag ata aag     1584
Glu Lys Leu Asp Ala Phe Phe Gly Phe Gln Leu Ser Gln Glu Ile Lys
            515                 520                 525 cag caa att cac cag tgc ctg aag agc tta ggg gag cgt ggc aat cct     1632
Gln Gln Ile His Gln Cys Leu Lys Ser Leu Gly Glu Arg Gly Asn Pro
530                 535                 540 cag gga cag gtg gat tcc ttg gcg ata ttt tac tgt ctc ttt gaa atg     1680
Gln Gly Gln Val Asp Ser Leu Ala Ile Phe Tyr Cys Leu Phe Glu Met
545                 550                 555                 560 cag gat cct gcc ttt gtg aag cag gca gtg aac ctc ctc caa gaa gct     1728
Gln Asp Pro Ala Phe Val Lys Gln Ala Val Asn Leu Leu Gln Glu Ala
                565                 570                 575 aac ttt cat att att gac aac gtg gac ttg gtg gtt tct gcc tac tgc     1776
Asn Phe His Ile Ile Asp Asn Val Asp Leu Val Val Ser Ala Tyr Cys
                580                 585                 590 tta aaa tac tgc tcc agc ttg agg aaa ctc tgt ttt tcc gtt caa aat     1824
Leu Lys Tyr Cys Ser Ser Leu Arg Lys Leu Cys Phe Ser Val Gln Asn
                595                 600                 605
```

```
                                                      -continued gtc ttt aag aaa gag gat gaa cac agc tct acg tcg gat tac agc ctc      1872
Val Phe Lys Lys Glu Asp Glu His Ser Ser Thr Ser Asp Tyr Ser Leu
    610             615                 620 atc tgt tgg cat cac atc tgc tct gtg ctc acc acc agc ggg cac ctc      1920
Ile Cys Trp His His Ile Cys Ser Val Leu Thr Thr Ser Gly His Leu
625                 630                 635                 640 aga gag ctc cag gtg cag gac agc acc ctc agc gag tcg acc ttt gtg      1968
Arg Glu Leu Gln Val Gln Asp Ser Thr Leu Ser Glu Ser Thr Phe Val
                645                 650                 655 acc tgg tgt aac cag ctg agg cat ccc agc tgt cgc ctt cag aag ctt      2016
Thr Trp Cys Asn Gln Leu Arg His Pro Ser Cys Arg Leu Gln Lys Leu
            660                 665                 670 gga ata aat aac gtt tcc ttt tct ggc cag agt gtt ctg ctc ttt gag      2064
Gly Ile Asn Asn Val Ser Phe Ser Gly Gln Ser Val Leu Leu Phe Glu
        675                 680                 685 gtg ctc ttt tat cag cca gac ttg aaa tac ctg agc ttc acc ctc acg      2112
Val Leu Phe Tyr Gln Pro Asp Leu Lys Tyr Leu Ser Phe Thr Leu Thr
    690                 695                 700 aaa ctc tct cgt gat gac atc agg tcc ctc tgt gat gcc ttg aac tac      2160
Lys Leu Ser Arg Asp Asp Ile Arg Ser Leu Cys Asp Ala Leu Asn Tyr
705                 710                 715                 720 cca gca ggc aac gtc aaa gag cta gcg ctg gta aat tgt cac ctc tca      2208
Pro Ala Gly Asn Val Lys Glu Leu Ala Leu Val Asn Cys His Leu Ser
                725                 730                 735 ccc att gat tgt gaa gtc ctt gct ggc ctt cta acc aac aac aag aag      2256
Pro Ile Asp Cys Glu Val Leu Ala Gly Leu Leu Thr Asn Asn Lys Lys
            740                 745                 750 ctg acg tat ctg aat gta tcc tgc aac cag tta gac aca ggc gtg ccc      2304
Leu Thr Tyr Leu Asn Val Ser Cys Asn Gln Leu Asp Thr Gly Val Pro
        755                 760                 765 ctt ttg tgt gaa gcc ctg tgc agc cca gac acg gtc ctg gta tac ctg      2352
Leu Leu Cys Glu Ala Leu Cys Ser Pro Asp Thr Val Leu Val Tyr Leu
    770                 775                 780 atg ttg gct ttc tgc cac ctc agc gag cag tgc tgc gaa tac atc tct      2400
Met Leu Ala Phe Cys His Leu Ser Glu Gln Cys Cys Glu Tyr Ile Ser
785                 790                 795                 800 gaa atg ctt ctg cgt aac aag agc gtg cgc tat cta gac ctc agt gcc      2448
Glu Met Leu Leu Arg Asn Lys Ser Val Arg Tyr Leu Asp Leu Ser Ala
                805                 810                 815 aat gtc ctg aag gac gaa gga ctg aaa act ctc tgc gag gcc ttg aaa      2496
Asn Val Leu Lys Asp Glu Gly Leu Lys Thr Leu Cys Glu Ala Leu Lys
            820                 825                 830 cat ccg gac tgc tgc ctg gat tca ctg tgt ttg gta aaa tgt ttt atc      2544
His Pro Asp Cys Cys Leu Asp Ser Leu Cys Leu Val Lys Cys Phe Ile
        835                 840                 845 act gct gct ggc tgt gaa gac ctc gcc tct gct ctc atc agc aat caa      2592
Thr Ala Ala Gly Cys Glu Asp Leu Ala Ser Ala Leu Ile Ser Asn Gln
    850                 855                 860 aac ctg aag att ctg caa att ggg tgc aat gaa atc gga gat gtg ggt      2640
Asn Leu Lys Ile Leu Gln Ile Gly Cys Asn Glu Ile Gly Asp Val Gly
865                 870                 875                 880 gtg cag ctg ttg tgt cgg gct ctg acg cat acg gat tgc cgc tta gag      2688
Val Gln Leu Leu Cys Arg Ala Leu Thr His Thr Asp Cys Arg Leu Glu
                885                 890                 895 att ctt ggg ttg gaa gaa tgt ggg tta acg agc acc tgc tgt aag gat      2736
Ile Leu Gly Leu Glu Glu Cys Gly Leu Thr Ser Thr Cys Cys Lys Asp
            900                 905                 910 ctc gcg tct gtt ctc acc tgc agt aag acc ctg cag cag ctc aac ctg      2784
Leu Ala Ser Val Leu Thr Cys Ser Lys Thr Leu Gln Gln Leu Asn Leu
        915                 920                 925
```

```
acc ttg aac acc ttg gac cac aca ggg gtt gtt gta ctc tgt gag gcc    2832
Thr Leu Asn Thr Leu Asp His Thr Gly Val Val Val Leu Cys Glu Ala
930                 935                 940 ctg aga cac cca gag tgt gcc ctg cag gtc ctc ggg ctg aga aaa act    2880
Leu Arg His Pro Glu Cys Ala Leu Gln Val Leu Gly Leu Arg Lys Thr
945                 950                 955                 960 gat ttt gat gag gaa acc cag gca ctt ctg acg gct gag gaa gag aga    2928
Asp Phe Asp Glu Glu Thr Gln Ala Leu Leu Thr Ala Glu Glu Glu Arg
                965                 970                 975 aat cct aac ctg acc atc aca gac gac tgt gac aca atc aca agg gta    2976
Asn Pro Asn Leu Thr Ile Thr Asp Asp Cys Asp Thr Ile Thr Arg Val
            980                 985                 990 gag atc tga                                                         2985
Glu Ile *

<210> SEQ ID NO 16
<211> LENGTH: 994
<212> TYPE: PRT
<213> ORGANISM: Homo sapien

<400> SEQUENCE: 16

Met Ala Ala Ser Phe Phe Ser Asp Phe Gly Leu Met Trp Tyr Leu Glu
1               5                   10                  15

Glu Leu Lys Lys Glu Glu Phe Arg Lys Phe Lys Glu His Leu Lys Gln
            20                  25                  30

Met Thr Leu Gln Leu Glu Leu Lys Gln Ile Pro Trp Thr Glu Val Lys
        35                  40                  45

Lys Ala Ser Arg Glu Glu Leu Ala Asn Leu Leu Ile Lys His Tyr Glu
    50                  55                  60

Glu Gln Gln Ala Trp Asn Ile Thr Leu Arg Ile Phe Gln Lys Met Asp
65                  70                  75                  80

Arg Lys Asp Leu Cys Met Lys Val Met Arg Glu Arg Thr Gly Tyr Thr
                85                  90                  95

Lys Thr Tyr Gln Ala His Ala Lys Gln Lys Phe Ser Arg Leu Trp Ser
            100                 105                 110

Ser Lys Ser Val Thr Glu Ile His Leu Tyr Phe Glu Glu Glu Val Lys
        115                 120                 125

Gln Glu Glu Cys Asp His Leu Asp Arg Leu Phe Ala Pro Lys Glu Thr
    130                 135                 140

Gly Lys Gln Pro Arg Thr Val Ile Ile Gln Gly Pro Gln Gly Ile Gly
145                 150                 155                 160

Lys Thr Thr Leu Leu Met Lys Leu Met Met Ala Trp Ser Asp Asn Lys
                165                 170                 175

Ile Phe Arg Asp Arg Phe Leu Tyr Thr Phe Tyr Phe Cys Cys Arg Glu
            180                 185                 190

Leu Arg Glu Leu Pro Pro Thr Ser Leu Ala Asp Leu Ile Ser Arg Glu
        195                 200                 205

Trp Pro Asp Pro Ala Ala Pro Ile Thr Glu Ile Val Ser Gln Pro Glu
    210                 215                 220

Arg Leu Leu Phe Val Ile Asp Ser Phe Glu Glu Leu Gln Gly Gly Leu
225                 230                 235                 240

Asn Glu Pro Asp Ser Asp Leu Cys Gly Asp Leu Met Glu Lys Arg Pro
                245                 250                 255

Val Gln Val Leu Leu Ser Ser Leu Leu Arg Lys Lys Met Leu Pro Glu
            260                 265                 270
```

-continued

```
Ala Ser Leu Leu Ile Ala Ile Lys Pro Val Cys Pro Lys Glu Leu Arg
            275                 280                 285

Asp Gln Val Thr Ile Ser Glu Ile Tyr Gln Pro Arg Gly Phe Asn Glu
        290                 295                 300

Ser Asp Arg Leu Val Tyr Phe Cys Cys Phe Phe Lys Asp Pro Lys Arg
305                 310                 315                 320

Ala Met Glu Ala Phe Asn Leu Val Arg Glu Ser Glu Gln Leu Phe Ser
                325                 330                 335

Ile Cys Gln Ile Pro Leu Leu Cys Trp Ile Leu Cys Thr Ser Leu Lys
            340                 345                 350

Gln Glu Met Gln Lys Gly Lys Asp Leu Ala Leu Thr Cys Gln Ser Thr
            355                 360                 365

Thr Ser Val Tyr Ser Ser Phe Val Phe Asn Leu Phe Thr Pro Glu Gly
        370                 375                 380

Ala Glu Gly Pro Thr Pro Gln Thr Gln His Gln Leu Lys Ala Leu Cys
385                 390                 395                 400

Ser Leu Ala Ala Glu Gly Met Trp Thr Asp Thr Phe Glu Phe Cys Glu
                405                 410                 415

Asp Asp Leu Arg Arg Asn Gly Val Val Asp Ala Asp Ile Pro Ala Leu
            420                 425                 430

Leu Gly Thr Lys Ile Leu Leu Lys Tyr Gly Glu Arg Glu Ser Ser Tyr
        435                 440                 445

Val Phe Leu His Val Cys Ile Gln Glu Phe Cys Ala Ala Leu Phe Tyr
        450                 455                 460

Leu Leu Lys Ser His Leu Asp His Pro His Pro Ala Val Arg Cys Val
465                 470                 475                 480

Gln Glu Leu Leu Val Ala Asn Phe Glu Lys Ala Arg Arg Ala His Trp
                485                 490                 495

Ile Phe Leu Gly Cys Phe Leu Thr Gly Leu Leu Asn Lys Lys Glu Gln
            500                 505                 510

Glu Lys Leu Asp Ala Phe Phe Gly Phe Gln Leu Ser Gln Glu Ile Lys
        515                 520                 525

Gln Gln Ile His Gln Cys Leu Lys Ser Leu Gly Glu Arg Gly Asn Pro
530                 535                 540

Gln Gly Gln Val Asp Ser Leu Ala Ile Phe Tyr Cys Leu Phe Glu Met
545                 550                 555                 560

Gln Asp Pro Ala Phe Val Lys Gln Ala Val Asn Leu Leu Gln Glu Ala
                565                 570                 575

Asn Phe His Ile Ile Asp Asn Val Asp Leu Val Val Ser Ala Tyr Cys
            580                 585                 590

Leu Lys Tyr Cys Ser Ser Leu Arg Lys Leu Cys Phe Ser Val Gln Asn
        595                 600                 605

Val Phe Lys Lys Glu Asp Glu His Ser Ser Thr Ser Asp Tyr Ser Leu
        610                 615                 620

Ile Cys Trp His His Ile Cys Ser Val Leu Thr Thr Ser Gly His Leu
625                 630                 635                 640

Arg Glu Leu Gln Val Gln Asp Ser Thr Leu Ser Glu Ser Thr Phe Val
                645                 650                 655

Thr Trp Cys Asn Gln Leu Arg His Pro Ser Cys Arg Leu Gln Lys Leu
            660                 665                 670

Gly Ile Asn Asn Val Ser Phe Ser Gly Gln Ser Val Leu Leu Phe Glu
        675                 680                 685
```

```
Val Leu Phe Tyr Gln Pro Asp Leu Lys Tyr Leu Ser Phe Thr Leu Thr
    690                 695                 700

Lys Leu Ser Arg Asp Asp Ile Arg Ser Leu Cys Asp Ala Leu Asn Tyr
705                 710                 715                 720

Pro Ala Gly Asn Val Lys Glu Leu Ala Leu Val Asn Cys His Leu Ser
                725                 730                 735

Pro Ile Asp Cys Glu Val Leu Ala Gly Leu Leu Thr Asn Asn Lys Lys
            740                 745                 750

Leu Thr Tyr Leu Asn Val Ser Cys Asn Gln Leu Asp Thr Gly Val Pro
        755                 760                 765

Leu Leu Cys Glu Ala Leu Cys Ser Pro Asp Thr Val Leu Val Tyr Leu
    770                 775                 780

Met Leu Ala Phe Cys His Leu Ser Glu Gln Cys Cys Glu Tyr Ile Ser
785                 790                 795                 800

Glu Met Leu Leu Arg Asn Lys Ser Val Arg Tyr Leu Asp Leu Ser Ala
                805                 810                 815

Asn Val Leu Lys Asp Glu Gly Leu Lys Thr Leu Cys Glu Ala Leu Lys
            820                 825                 830

His Pro Asp Cys Cys Leu Asp Ser Leu Cys Leu Val Lys Cys Phe Ile
        835                 840                 845

Thr Ala Ala Gly Cys Glu Asp Leu Ala Ser Ala Leu Ile Ser Asn Gln
    850                 855                 860

Asn Leu Lys Ile Leu Gln Ile Gly Cys Asn Glu Ile Gly Asp Val Gly
865                 870                 875                 880

Val Gln Leu Leu Cys Arg Ala Leu Thr His Thr Asp Cys Arg Leu Glu
                885                 890                 895

Ile Leu Gly Leu Glu Glu Cys Gly Leu Thr Ser Thr Cys Cys Lys Asp
            900                 905                 910

Leu Ala Ser Val Leu Thr Cys Ser Lys Thr Leu Gln Gln Leu Asn Leu
        915                 920                 925

Thr Leu Asn Thr Leu Asp His Thr Gly Val Val Leu Cys Glu Ala
    930                 935                 940

Leu Arg His Pro Glu Cys Ala Leu Gln Val Leu Gly Leu Arg Lys Thr
945                 950                 955                 960

Asp Phe Asp Glu Glu Thr Gln Ala Leu Leu Thr Ala Glu Glu Arg
                965                 970                 975

Asn Pro Asn Leu Thr Ile Thr Asp Asp Cys Asp Thr Ile Thr Arg Val
            980                 985                 990

Glu Ile

<210> SEQ ID NO 17
<211> LENGTH: 2844
<212> TYPE: DNA
<213> ORGANISM: Homo sapien
<220> FEATURE:
<221> NAME/KEY: CDS
<222> LOCATION: (1)...(2841)

<400> SEQUENCE: 17 atg gac cag cca gag gcc ccc tgc tcc agc acg ggg ccg cgc ctc gcg      48
Met Asp Gln Pro Glu Ala Pro Cys Ser Ser Thr Gly Pro Arg Leu Ala
1               5                   10                  15 gtg gcc cgc gag ctg ctc ctg gct gcg ctg gag gaa ctg agc caa gag      96
Val Ala Arg Glu Leu Leu Leu Ala Ala Leu Glu Glu Leu Ser Gln Glu
            20                  25                  30
```

-continued

| | |
|---|---|
| cag ctg aag cgc ttc cgc cac aag ctg cgc gac gtg ggc ccg gac gga<br>Gln Leu Lys Arg Phe Arg His Lys Leu Arg Asp Val Gly Pro Asp Gly<br>35                       40                       45 | 144 |
| cgc agc atc ccg tgg ggg cgg ctg gag cgc gcg gac gcc gtg gac ctc<br>Arg Ser Ile Pro Trp Gly Arg Leu Glu Arg Ala Asp Ala Val Asp Leu<br>50                       55                       60 | 192 |
| gcg gag cag ctg gcc cag ttc tac ggc ccg gag cct gcc ctg gag gtg<br>Ala Glu Gln Leu Ala Gln Phe Tyr Gly Pro Glu Pro Ala Leu Glu Val<br>65                       70                       75                       80 | 240 |
| gcc cgc aag acc ctc aag agg gcg gac gcg cgc gac gtg gcg gcg cag<br>Ala Arg Lys Thr Leu Lys Arg Ala Asp Ala Arg Asp Val Ala Ala Gln<br>                       85                       90                       95 | 288 |
| ctc cag gag cgg cgg ctg cag cgg ctc ggc ctc ggc tcc ggg acg ctg<br>Leu Gln Glu Arg Arg Leu Gln Arg Leu Gly Leu Gly Ser Gly Thr Leu<br>                       100                   105                   110 | 336 |
| ctc tcc gtg tcc gag tac aag aag aag tac cgg gag cac gtg ctg cag<br>Leu Ser Val Ser Glu Tyr Lys Lys Lys Tyr Arg Glu His Val Leu Gln<br>               115                   120                   125 | 384 |
| ctg cac gct cgg gtg aag gag agg aac gcc cgc tcc gtg aag atc acc<br>Leu His Ala Arg Val Lys Glu Arg Asn Ala Arg Ser Val Lys Ile Thr<br>130                       135                   140 | 432 |
| aag cgc ttc acc aag ctg ctc atc gcg ccc gag agc gcc gcc ccg gag<br>Lys Arg Phe Thr Lys Leu Leu Ile Ala Pro Glu Ser Ala Ala Pro Glu<br>145                       150                   155                   160 | 480 |
| gag gcg ctg ggg ccc gcg gaa gag cct gag ccg ggg cgc gcg cgg cgc<br>Glu Ala Leu Gly Pro Ala Glu Glu Pro Glu Pro Gly Arg Ala Arg Arg<br>                       165                   170                   175 | 528 |
| tcg gac acg cac act ttc aac cgc ctc ttc cgc cgc gac gag gag ggc<br>Ser Asp Thr His Thr Phe Asn Arg Leu Phe Arg Arg Asp Glu Glu Gly<br>                          180                   185                   190 | 576 |
| cgg cgg ccg ctg acc gtg gtg ctg cag ggc ccg gcg ggc atc ggc aag<br>Arg Arg Pro Leu Thr Val Val Leu Gln Gly Pro Ala Gly Ile Gly Lys<br>               195                   200                   205 | 624 |
| acc atg gcg gcc aaa aag atc ctg tac gac tgg gcg gcg ggc aag ctg<br>Thr Met Ala Ala Lys Lys Ile Leu Tyr Asp Trp Ala Ala Gly Lys Leu<br>210                       215                   220 | 672 |
| tac cag ggc cag gtg gac ttc gcc ttc ttc atg ccc tgc ggc gag ctg<br>Tyr Gln Gly Gln Val Asp Phe Ala Phe Phe Met Pro Cys Gly Glu Leu<br>225                       230                   235                   240 | 720 |
| ctg gag agg ccg ggc acg cgc agc ctg gct gac ctg atc ctg gac cag<br>Leu Glu Arg Pro Gly Thr Arg Ser Leu Ala Asp Leu Ile Leu Asp Gln<br>                       245                   250                   255 | 768 |
| tgc ccc gac cgc ggc gcg ccg gtg ccg cag atg ctg gcc cag ccg cag<br>Cys Pro Asp Arg Gly Ala Pro Val Pro Gln Met Leu Ala Gln Pro Gln<br>                       260                   265                   270 | 816 |
| cgg ctg ctc ttc atc ctg gac ggc gcg gac gag ctg ccg gcg ctg ggg<br>Arg Leu Leu Phe Ile Leu Asp Gly Ala Asp Glu Leu Pro Ala Leu Gly<br>               275                   280                   285 | 864 |
| ggc ccc gag gcc gcg ccc tgc aca gac ccc ttc gag gcg gcg agc ggc<br>Gly Pro Glu Ala Ala Pro Cys Thr Asp Pro Phe Glu Ala Ala Ser Gly<br>290                       295                   300 | 912 |
| gcg cgg gtg cta ggc ggg ctg ctg agc aag gcg ctg ctg ccc acg gcc<br>Ala Arg Val Leu Gly Gly Leu Leu Ser Lys Ala Leu Leu Pro Thr Ala<br>305                       310                   315                   320 | 960 |
| ctc ctg ctg gtg acc acg cgc gcc gcc gcc ccc ggg agg ctg cag ggc<br>Leu Leu Leu Val Thr Thr Arg Ala Ala Ala Pro Gly Arg Leu Gln Gly<br>                       325                   330                   335 | 1008 |
| cgc ctg tgt tcc ccg cag tgc gcc gag gtg cgc ggc ttc tcc gac aag<br>Arg Leu Cys Ser Pro Gln Cys Ala Glu Val Arg Gly Phe Ser Asp Lys<br>                       340                   345                   350 | 1056 |

-continued

| | |
|---|---|
| gac aag aag aag tat ttc tac aag ttc ttc cgg gat gag agg agg gcc<br>Asp Lys Lys Lys Tyr Phe Tyr Lys Phe Phe Arg Asp Glu Arg Arg Ala<br>355                            360                     365 | 1104 |
| gag cgc gcc tac cgc ttc gtg aag gag aac gag acg ctg ttc gcg ctg<br>Glu Arg Ala Tyr Arg Phe Val Lys Glu Asn Glu Thr Leu Phe Ala Leu<br>370                            375                     380 | 1152 |
| tgc ttc gtg ccc ttc gtg tgc tgg atc gtg tgc acc gtg ctg cgc cag<br>Cys Phe Val Pro Phe Val Cys Trp Ile Val Cys Thr Val Leu Arg Gln<br>385                            390                     395                     400 | 1200 |
| cag ctg gag ctc ggt cgg gac ctg tcg cgc acg tcc aag acc acc acg<br>Gln Leu Glu Leu Gly Arg Asp Leu Ser Arg Thr Ser Lys Thr Thr Thr<br>                           405                     410                     415 | 1248 |
| tca gtg tac ctg ctt ttc atc acc agc gtt ctg agc tcg gct ccg gta<br>Ser Val Tyr Leu Leu Phe Ile Thr Ser Val Leu Ser Ser Ala Pro Val<br>                 420                     425                     430 | 1296 |
| gcc gac ggg ccc cgg ttg cag ggc gac ctg cgc aat ctg tgc cgc ctg<br>Ala Asp Gly Pro Arg Leu Gln Gly Asp Leu Arg Asn Leu Cys Arg Leu<br>                 435                     440                     445 | 1344 |
| gcc cgc gag ggc gtc ctc gga cgc agg gcg cag ttt gcc gag aag gaa<br>Ala Arg Glu Gly Val Leu Gly Arg Arg Ala Gln Phe Ala Glu Lys Glu<br>450                            455                     460 | 1392 |
| ctg gag caa ctg gag ctt cgt ggc tcc aaa gtg cag acg ctg ttt ctc<br>Leu Glu Gln Leu Glu Leu Arg Gly Ser Lys Val Gln Thr Leu Phe Leu<br>465                            470                     475                     480 | 1440 |
| agc aaa aag gag ctg ccg ggc gtg ctg gag aca gag gtc acc tac cag<br>Ser Lys Lys Glu Leu Pro Gly Val Leu Glu Thr Glu Val Thr Tyr Gln<br>                 485                     490                     495 | 1488 |
| ttc atc gac cag agc ttc cag gag ttc ctc gcg gca ctg tcc tac ctg<br>Phe Ile Asp Gln Ser Phe Gln Glu Phe Leu Ala Ala Leu Ser Tyr Leu<br>                 500                     505                     510 | 1536 |
| ctg gag gac ggc ggg gtg ccc agg acc gcg gct ggc ggc gtt ggg aca<br>Leu Glu Asp Gly Gly Val Pro Arg Thr Ala Ala Gly Gly Val Gly Thr<br>                 515                     520                     525 | 1584 |
| ctc ctg cgt ggg gac gcc cag ccg cac agc cac ttg gtg ctc acc acg<br>Leu Leu Arg Gly Asp Ala Gln Pro His Ser His Leu Val Leu Thr Thr<br>530                            535                     540 | 1632 |
| cgc ttc ctc ttc gga ctg ctg agc gcg gag cgg atg cgc gac atc gag<br>Arg Phe Leu Phe Gly Leu Leu Ser Ala Glu Arg Met Arg Asp Ile Glu<br>545                            550                     555                     560 | 1680 |
| cgc cac ttc ggc tgc atg gtt tca gag cgt gtg aag cag gag gcc ctg<br>Arg His Phe Gly Cys Met Val Ser Glu Arg Val Lys Gln Glu Ala Leu<br>                 565                     570                     575 | 1728 |
| cgg tgg gtg cag gga cag gga cag ggc tgc ccc gga gtg gca cca gag<br>Arg Trp Val Gln Gly Gln Gly Gln Gly Cys Pro Gly Val Ala Pro Glu<br>                 580                     585                     590 | 1776 |
| gtg acc gag ggg gcc aaa ggg ctc gag gac acc gaa gag cca gag gag<br>Val Thr Glu Gly Ala Lys Gly Leu Glu Asp Thr Glu Glu Pro Glu Glu<br>                           595                     600                     605 | 1824 |
| gag gag gag gga gag gag ccc aac tac cca ctg gag ttg ctg tac tgc<br>Glu Glu Glu Gly Glu Glu Pro Asn Tyr Pro Leu Glu Leu Leu Tyr Cys<br>                 610                     615                     620 | 1872 |
| ctg tac gag acg cag gag gac gcg ttt gtg cgc caa gcc ctg tgc cgg<br>Leu Tyr Glu Thr Gln Glu Asp Ala Phe Val Arg Gln Ala Leu Cys Arg<br>625                            630                     635                     640 | 1920 |
| ttc ccg gag ctg gcg ctg cag cga gtg cgc ttc tgc cgc atg gac gtg<br>Phe Pro Glu Leu Ala Leu Gln Arg Val Arg Phe Cys Arg Met Asp Val<br>                           645                     650                     655 | 1968 |
| gct gtt ctg agc tac tgc gtg agg tgc tgc cct gct gga cag gca ctg<br>Ala Val Leu Ser Tyr Cys Val Arg Cys Cys Pro Ala Gly Gln Ala Leu<br>                 660                     665                     670 | 2016 |

```
cgg ctg atc agc tgc aga ttg gtt gct gcg cag gag aag aag aag aag      2064
Arg Leu Ile Ser Cys Arg Leu Val Ala Ala Gln Glu Lys Lys Lys Lys
            675                 680                 685 agc ctg ggg aag cgg ctc cag gcc agc ctg ggt ggc ggc agc tgg ctg      2112
Ser Leu Gly Lys Arg Leu Gln Ala Ser Leu Gly Gly Gly Ser Trp Leu
        690                 695                 700 ggg acc caa ctg gct cca gaa gta ccc ttt cga ccc tgc tgt gac          2160
Gly Thr Gln Leu Ala Pro Glu Val Pro Phe Arg Pro Pro Cys Cys Asp
705                 710                 715                 720 atc tgc ccc aca cct cca cca gac cct cgg ctc ctc cag ggc aag gct      2208
Ile Cys Pro Thr Pro Pro Pro Asp Pro Arg Leu Leu Gln Gly Lys Ala
                725                 730                 735 ttt gcc aga gtt cct ttg aat ata gct cca att cag ccc ctg ccc agg      2256
Phe Ala Arg Val Pro Leu Asn Ile Ala Pro Ile Gln Pro Leu Pro Arg
            740                 745                 750 ggc ttg gca tct gtt gag agg atg aat gtc acg gtg ttg gca ggg gct      2304
Gly Leu Ala Ser Val Glu Arg Met Asn Val Thr Val Leu Ala Gly Ala
        755                 760                 765 ggg cct ggg gac cca aag acc cat gca atg act gac cca ctg tgc cat      2352
Gly Pro Gly Asp Pro Lys Thr His Ala Met Thr Asp Pro Leu Cys His
770                 775                 780 ctg agc agc ctc acg ctg tcc cac tgc aaa ctc cct gac gcg gtc tgc      2400
Leu Ser Ser Leu Thr Leu Ser His Cys Lys Leu Pro Asp Ala Val Cys
785                 790                 795                 800 cga gac ctt tct gag gcc ctg agg gca gcc ccc gca ctg acg gag ctg      2448
Arg Asp Leu Ser Glu Ala Leu Arg Ala Ala Pro Ala Leu Thr Glu Leu
                805                 810                 815 ggc ctc ctc cac aac agg ctc agt gag gca gga ctg cgt atg ctg agt      2496
Gly Leu Leu His Asn Arg Leu Ser Glu Ala Gly Leu Arg Met Leu Ser
            820                 825                 830 gag ggc cta gcc tgg ccg cag tgc agg gtg cag acg gtc agg gta cag      2544
Glu Gly Leu Ala Trp Pro Gln Cys Arg Val Gln Thr Val Arg Val Gln
        835                 840                 845 ctg cct gac ccc cag cga ggg ctc cag tac ctg gtg ggt atg ctt cgg      2592
Leu Pro Asp Pro Gln Arg Gly Leu Gln Tyr Leu Val Gly Met Leu Arg
850                 855                 860 cag agc cct gcc ctg acc acc ctg gat ctc agc ggc tgc caa ctg ccc      2640
Gln Ser Pro Ala Leu Thr Thr Leu Asp Leu Ser Gly Cys Gln Leu Pro
865                 870                 875                 880 gcc ccc atg gtg acc tac ctg tgt gca gtc ctg cag cac cag gga tgc      2688
Ala Pro Met Val Thr Tyr Leu Cys Ala Val Leu Gln His Gln Gly Cys
                885                 890                 895 ggc ctg cag acc ctc agt ctg gcc tct gtg gag ctg agc gag cag tca      2736
Gly Leu Gln Thr Leu Ser Leu Ala Ser Val Glu Leu Ser Glu Gln Ser
            900                 905                 910 cta cag gag ctt cag gct gtg aag aga gca aag ccg gat ctg gtc atc      2784
Leu Gln Glu Leu Gln Ala Val Lys Arg Ala Lys Pro Asp Leu Val Ile
        915                 920                 925 aca cac cca gcg ctg gac ggc cac cca caa cct ccc aag gaa ctc atc      2832
Thr His Pro Ala Leu Asp Gly His Pro Gln Pro Pro Lys Glu Leu Ile
930                 935                 940 tcg acc ttc tga                                                      2844
Ser Thr Phe
945

<210> SEQ ID NO 18
<211> LENGTH: 947
<212> TYPE: PRT
<213> ORGANISM: Homo sapien
```

<400> SEQUENCE: 18

```
Met Asp Gln Pro Glu Ala Pro Cys Ser Ser Thr Gly Pro Arg Leu Ala
 1               5                  10                  15

Val Ala Arg Glu Leu Leu Ala Ala Leu Glu Glu Leu Ser Gln Glu
             20                  25                  30

Gln Leu Lys Arg Phe Arg His Lys Leu Arg Asp Val Gly Pro Asp Gly
             35                  40                  45

Arg Ser Ile Pro Trp Gly Arg Leu Glu Arg Ala Asp Ala Val Asp Leu
         50                  55                  60

Ala Glu Gln Leu Ala Gln Phe Tyr Gly Pro Glu Pro Ala Leu Glu Val
 65                  70                  75                  80

Ala Arg Lys Thr Leu Lys Arg Ala Asp Ala Arg Asp Val Ala Ala Gln
                 85                  90                  95

Leu Gln Glu Arg Arg Leu Gln Arg Leu Gly Leu Gly Ser Gly Thr Leu
            100                 105                 110

Leu Ser Val Ser Glu Tyr Lys Lys Lys Tyr Arg Glu His Val Leu Gln
            115                 120                 125

Leu His Ala Arg Val Lys Glu Arg Asn Ala Arg Ser Val Lys Ile Thr
        130                 135                 140

Lys Arg Phe Thr Lys Leu Leu Ile Ala Pro Glu Ser Ala Ala Pro Glu
145                 150                 155                 160

Glu Ala Leu Gly Pro Ala Glu Glu Pro Glu Pro Gly Arg Ala Arg Arg
                165                 170                 175

Ser Asp Thr His Thr Phe Asn Arg Leu Phe Arg Arg Asp Glu Glu Gly
            180                 185                 190

Arg Arg Pro Leu Thr Val Val Leu Gln Gly Pro Ala Gly Ile Gly Lys
        195                 200                 205

Thr Met Ala Ala Lys Lys Ile Leu Tyr Asp Trp Ala Ala Gly Lys Leu
210                 215                 220

Tyr Gln Gly Gln Val Asp Phe Ala Phe Phe Met Pro Cys Gly Glu Leu
225                 230                 235                 240

Leu Glu Arg Pro Gly Thr Arg Ser Leu Ala Asp Leu Ile Leu Asp Gln
                245                 250                 255

Cys Pro Asp Arg Gly Ala Pro Val Pro Gln Met Leu Ala Gln Pro Gln
            260                 265                 270

Arg Leu Leu Phe Ile Leu Asp Gly Ala Asp Glu Leu Pro Ala Leu Gly
        275                 280                 285

Gly Pro Glu Ala Ala Pro Cys Thr Asp Pro Phe Glu Ala Ala Ser Gly
290                 295                 300

Ala Arg Val Leu Gly Gly Leu Leu Ser Lys Ala Leu Leu Pro Thr Ala
305                 310                 315                 320

Leu Leu Leu Val Thr Thr Arg Ala Ala Ala Pro Gly Arg Leu Gln Gly
                325                 330                 335

Arg Leu Cys Ser Pro Gln Cys Ala Glu Val Arg Gly Phe Ser Asp Lys
            340                 345                 350

Asp Lys Lys Lys Tyr Phe Tyr Lys Phe Phe Arg Asp Glu Arg Arg Ala
        355                 360                 365

Glu Arg Ala Tyr Arg Phe Val Lys Glu Asn Glu Thr Leu Phe Ala Leu
370                 375                 380

Cys Phe Val Pro Phe Val Cys Trp Ile Val Cys Thr Val Leu Arg Gln
385                 390                 395                 400

Gln Leu Glu Leu Gly Arg Asp Leu Ser Arg Thr Ser Lys Thr Thr Thr
                405                 410                 415
```

```
Ser Val Tyr Leu Leu Phe Ile Thr Ser Val Leu Ser Ser Ala Pro Val
                420                 425                 430

Ala Asp Gly Pro Arg Leu Gln Gly Asp Leu Arg Asn Leu Cys Arg Leu
            435                 440                 445

Ala Arg Glu Gly Val Leu Gly Arg Arg Ala Gln Phe Ala Glu Lys Glu
        450                 455                 460

Leu Glu Gln Leu Glu Leu Arg Gly Ser Lys Val Gln Thr Leu Phe Leu
465                 470                 475                 480

Ser Lys Lys Glu Leu Pro Gly Val Leu Glu Thr Glu Val Thr Tyr Gln
                485                 490                 495

Phe Ile Asp Gln Ser Phe Gln Glu Phe Leu Ala Ala Leu Ser Tyr Leu
            500                 505                 510

Leu Glu Asp Gly Gly Val Pro Arg Thr Ala Ala Gly Gly Val Gly Thr
        515                 520                 525

Leu Leu Arg Gly Asp Ala Gln Pro His Ser His Leu Val Leu Thr Thr
530                 535                 540

Arg Phe Leu Phe Gly Leu Leu Ser Ala Glu Arg Met Arg Asp Ile Glu
545                 550                 555                 560

Arg His Phe Gly Cys Met Val Ser Glu Arg Val Lys Gln Glu Ala Leu
                565                 570                 575

Arg Trp Val Gln Gly Gln Gly Gln Gly Cys Pro Gly Val Ala Pro Glu
            580                 585                 590

Val Thr Glu Gly Ala Lys Gly Leu Glu Asp Thr Glu Glu Pro Glu Glu
        595                 600                 605

Glu Glu Glu Gly Glu Glu Pro Asn Tyr Pro Leu Glu Leu Leu Tyr Cys
610                 615                 620

Leu Tyr Glu Thr Gln Glu Asp Ala Phe Val Arg Gln Ala Leu Cys Arg
625                 630                 635                 640

Phe Pro Glu Leu Ala Leu Gln Arg Val Arg Phe Cys Arg Met Asp Val
                645                 650                 655

Ala Val Leu Ser Tyr Cys Val Arg Cys Cys Pro Ala Gly Gln Ala Leu
            660                 665                 670

Arg Leu Ile Ser Cys Arg Leu Val Ala Ala Gln Glu Lys Lys Lys Lys
        675                 680                 685

Ser Leu Gly Lys Arg Leu Gln Ala Ser Leu Gly Gly Gly Ser Trp Leu
690                 695                 700

Gly Thr Gln Leu Ala Pro Glu Val Pro Phe Arg Pro Pro Cys Cys Asp
705                 710                 715                 720

Ile Cys Pro Thr Pro Pro Asp Pro Arg Leu Leu Gln Gly Lys Ala
                725                 730                 735

Phe Ala Arg Val Pro Leu Asn Ile Ala Pro Ile Gln Pro Leu Pro Arg
            740                 745                 750

Gly Leu Ala Ser Val Glu Arg Met Asn Val Thr Val Leu Ala Gly Ala
        755                 760                 765

Gly Pro Gly Asp Pro Lys Thr His Ala Met Thr Asp Pro Leu Cys His
770                 775                 780

Leu Ser Ser Leu Thr Leu Ser His Cys Lys Leu Pro Asp Ala Val Cys
785                 790                 795                 800

Arg Asp Leu Ser Glu Ala Leu Arg Ala Ala Pro Ala Leu Thr Glu Leu
                805                 810                 815

Gly Leu Leu His Asn Arg Leu Ser Glu Ala Gly Leu Arg Met Leu Ser
            820                 825                 830
```

```
Glu Gly Leu Ala Trp Pro Gln Cys Arg Val Gln Thr Val Arg Val Gln
        835                 840                 845

Leu Pro Asp Pro Gln Arg Gly Leu Gln Tyr Leu Val Gly Met Leu Arg
        850                 855             860

Gln Ser Pro Ala Leu Thr Thr Leu Asp Leu Ser Gly Cys Gln Leu Pro
865                 870                 875                 880

Ala Pro Met Val Thr Tyr Leu Cys Ala Val Leu Gln His Gln Gly Cys
                885                 890                 895

Gly Leu Gln Thr Leu Ser Leu Ala Ser Val Glu Leu Ser Glu Gln Ser
                900                 905                 910

Leu Gln Glu Leu Gln Ala Val Lys Arg Ala Lys Pro Asp Leu Val Ile
        915                 920                 925

Thr His Pro Ala Leu Asp Gly His Pro Gln Pro Pro Lys Glu Leu Ile
        930                 935                 940

Ser Thr Phe
945

<210> SEQ ID NO 19
<211> LENGTH: 2046
<212> TYPE: DNA
<213> ORGANISM: Homo sapien
<220> FEATURE:
<221> NAME/KEY: CDS
<222> LOCATION: (1)...(2043)

<400> SEQUENCE: 19 atg agt gac gtg aat cca ccc tct gac acc ccc att ccc ttt tca tcc      48
Met Ser Asp Val Asn Pro Pro Ser Asp Thr Pro Ile Pro Phe Ser Ser
 1               5                  10                  15 tcc tcc act cac agt tct cat att ccg ccc tgg aca ttc tct tgc tac      96
Ser Ser Thr His Ser Ser His Ile Pro Pro Trp Thr Phe Ser Cys Tyr
                20                  25                  30 ccc ggc tcc cca tgt gaa aat ggg gtc atg ctg tac atg aga aac gtg     144
Pro Gly Ser Pro Cys Glu Asn Gly Val Met Leu Tyr Met Arg Asn Val
            35                  40                  45 agc cat gag gag cta caa cgg ttc aag cag ctc tta ctg act gag ctc     192
Ser His Glu Glu Leu Gln Arg Phe Lys Gln Leu Leu Leu Thr Glu Leu
        50                  55                  60 agt act ggc acc atg ccc atc acc tgg gac cag gtc gag aca gcc agc     240
Ser Thr Gly Thr Met Pro Ile Thr Trp Asp Gln Val Glu Thr Ala Ser
65                  70                  75                  80 tgg gca gag gtg gtt cat ctc ttg ata gag cgt ttc cct gga cga cgc     288
Trp Ala Glu Val Val His Leu Leu Ile Glu Arg Phe Pro Gly Arg Arg
                85                  90                  95 gct tgg gat gtg act tcg aac atc ttt gcc att atg aac tgt gat aaa     336
Ala Trp Asp Val Thr Ser Asn Ile Phe Ala Ile Met Asn Cys Asp Lys
            100                 105                 110 atg tgt gtt gta gtc cgc aga gag ata aat gcc att ctg cct acc ttg     384
Met Cys Val Val Arg Arg Glu Ile Asn Ala Ile Leu Pro Thr Leu
        115                 120                 125 gaa cca gag gac ttg aat gtg gga gaa aca cag gtg aat ctg gag gaa     432
Glu Pro Glu Asp Leu Asn Val Gly Glu Thr Gln Val Asn Leu Glu Glu
    130                 135                 140 gga gaa tct ggt aaa ata cgg cgg tat aaa tcg aat gtg atg gaa aag     480
Gly Glu Ser Gly Lys Ile Arg Arg Tyr Lys Ser Asn Val Met Glu Lys
145                 150                 155                 160 ttt ttc ccc ata tgg gac att acg act tgg cct gga aac cag agg gac     528
Phe Phe Pro Ile Trp Asp Ile Thr Thr Trp Pro Gly Asn Gln Arg Asp
                165                 170                 175
```

```
ttc ttc tac caa ggt gta cac agg cac gag gag tac tta cca tgt ctg      576
Phe Phe Tyr Gln Gly Val His Arg His Glu Glu Tyr Leu Pro Cys Leu
        180                 185                 190 ctt ctg ccc aaa aga ccc cag ggt aga cag ccc aag acc gtg gcc ata      624
Leu Leu Pro Lys Arg Pro Gln Gly Arg Gln Pro Lys Thr Val Ala Ile
            195                 200                 205 cag gga gct cct ggg atc gga aaa aca atc ctg gcc aaa aag gtg atg      672
Gln Gly Ala Pro Gly Ile Gly Lys Thr Ile Leu Ala Lys Lys Val Met
    210                 215                 220 ttt gag tgg gcc aga aac aag ttc tac gcc cac aag cgc tgg tgt gct      720
Phe Glu Trp Ala Arg Asn Lys Phe Tyr Ala His Lys Arg Trp Cys Ala
225                 230                 235                 240 ttc tac ttc cat tgc caa gag gtg aac cag acg aca gac cag agc ttc      768
Phe Tyr Phe His Cys Gln Glu Val Asn Gln Thr Thr Asp Gln Ser Phe
                245                 250                 255 tcc gag ctg att gag caa aag tgg cct gga tct cag gac ctc gtg tca      816
Ser Glu Leu Ile Glu Gln Lys Trp Pro Gly Ser Gln Asp Leu Val Ser
            260                 265                 270 aag att atg tcc aaa ccc gac caa ctt ctg ctg ctc ttg gat ggc ttt      864
Lys Ile Met Ser Lys Pro Asp Gln Leu Leu Leu Leu Leu Asp Gly Phe
        275                 280                 285 gag gag ctc aca tct acc ctc att gac aga ctg gag gac ctg agt gaa      912
Glu Glu Leu Thr Ser Thr Leu Ile Asp Arg Leu Glu Asp Leu Ser Glu
    290                 295                 300 gac tgg agg cag aaa ttg cct ggg tct gtc cta ctg agc agt ttg ctg      960
Asp Trp Arg Gln Lys Leu Pro Gly Ser Val Leu Leu Ser Ser Leu Leu
305                 310                 315                 320 agc aaa acg atg ctt cca gag gcc acg cta ctg atc atg ata aga ttt     1008
Ser Lys Thr Met Leu Pro Glu Ala Thr Leu Leu Ile Met Ile Arg Phe
                325                 330                 335 acc tct tgg cag aca tgc aag ccc ttg ctg aaa tgt ccc tct ctc gta     1056
Thr Ser Trp Gln Thr Cys Lys Pro Leu Leu Lys Cys Pro Ser Leu Val
            340                 345                 350 acc ctt ccg ggg ttt aat acg atg gaa aaa atc aag tat ttc cag atg     1104
Thr Leu Pro Gly Phe Asn Thr Met Glu Lys Ile Lys Tyr Phe Gln Met
        355                 360                 365 tat ttt gga cac aca gag gag gga gac caa gtc ttg agt ttc gcc atg     1152
Tyr Phe Gly His Thr Glu Glu Gly Asp Gln Val Leu Ser Phe Ala Met
    370                 375                 380 gaa aac acc att ctc ttc tcc atg tgc cgg gtc cct gtg gtt tgc tgg     1200
Glu Asn Thr Ile Leu Phe Ser Met Cys Arg Val Pro Val Val Cys Trp
385                 390                 395                 400 atg gtc tgc tct ggt ctg aaa cag caa atg gag aga gga aac aat ctc     1248
Met Val Cys Ser Gly Leu Lys Gln Gln Met Glu Arg Gly Asn Asn Leu
                405                 410                 415 aca cag tca tgt cca aat gcc acc tct gtg ttc gtc cgg tat att tct     1296
Thr Gln Ser Cys Pro Asn Ala Thr Ser Val Phe Val Arg Tyr Ile Ser
            420                 425                 430 agc ttg ttt ccc acc aga gct gag aac ttt tcc aga aag atc cac caa     1344
Ser Leu Phe Pro Thr Arg Ala Glu Asn Phe Ser Arg Lys Ile His Gln
        435                 440                 445 gca caa ctg gaa ggt ctg tgt cac ttg gcc gca gac agc atg tgg cac     1392
Ala Gln Leu Glu Gly Leu Cys His Leu Ala Ala Asp Ser Met Trp His
    450                 455                 460 agg aaa tgg gtg tta ggt aaa gaa gat ctt gag gaa gcc aag ctg gat     1440
Arg Lys Trp Val Leu Gly Lys Glu Asp Leu Glu Glu Ala Lys Leu Asp
465                 470                 475                 480 cag acg gga gtc acc gcc ttc ctt ggc atg agt att ctt cgg aga att     1488
Gln Thr Gly Val Thr Ala Phe Leu Gly Met Ser Ile Leu Arg Arg Ile
                485                 490                 495
```

| | | | | | | | | | | | | | | | | |
|---|---|---|---|---|---|---|---|---|---|---|---|---|---|---|---|---|
| gca | ggt | gag | gaa | gac | cac | tat | gtc | ttt | acc | ctc | gtg | act | ttt | cag | gaa | 1536 |
| Ala | Gly | Glu | Glu | Asp | His | Tyr | Val | Phe | Thr | Leu | Val | Thr | Phe | Gln | Glu | |
| | | 500 | | | | | 505 | | | | | 510 | | | | |
| ttt | ttt | gcg | gcc | ttg | ttt | tat | gtt | ctc | tgt | ttc | cca | caa | aga | ctc | aaa | 1584 |
| Phe | Phe | Ala | Ala | Leu | Phe | Tyr | Val | Leu | Cys | Phe | Pro | Gln | Arg | Leu | Lys | |
| | | 515 | | | | | 520 | | | | | 525 | | | | |
| aat | ttt | cat | gtg | ttg | agc | cac | gtg | aat | atc | cag | cgc | ctg | ata | gcg | agt | 1632 |
| Asn | Phe | His | Val | Leu | Ser | His | Val | Asn | Ile | Gln | Arg | Leu | Ile | Ala | Ser | |
| 530 | | | | | 535 | | | | | 540 | | | | | | |
| ccc | aga | gga | agc | aaa | agc | tat | ctc | tct | cac | atg | gga | ctt | ttc | tta | ttc | 1680 |
| Pro | Arg | Gly | Ser | Lys | Ser | Tyr | Leu | Ser | His | Met | Gly | Leu | Phe | Leu | Phe | |
| 545 | | | | | 550 | | | | | 555 | | | | | 560 | |
| ggt | ttt | ctg | aac | gag | gcc | tgc | gct | tcg | gcc | gtg | gaa | cag | tca | ttc | caa | 1728 |
| Gly | Phe | Leu | Asn | Glu | Ala | Cys | Ala | Ser | Ala | Val | Glu | Gln | Ser | Phe | Gln | |
| | | | | 565 | | | | | 570 | | | | | 575 | | |
| tgc | aag | gtg | tct | ttc | ggt | aat | aag | agg | aaa | ctg | ctg | aaa | gtc | ata | cct | 1776 |
| Cys | Lys | Val | Ser | Phe | Gly | Asn | Lys | Arg | Lys | Leu | Leu | Lys | Val | Ile | Pro | |
| | | | 580 | | | | | 585 | | | | | 590 | | | |
| ctg | ttg | cat | aaa | tgt | gac | cca | cct | tct | ccg | ggc | agt | ggg | gtc | ccg | cag | 1824 |
| Leu | Leu | His | Lys | Cys | Asp | Pro | Pro | Ser | Pro | Gly | Ser | Gly | Val | Pro | Gln | |
| | | 595 | | | | | 600 | | | | | 605 | | | | |
| tta | ttc | tac | tgt | ctg | cat | gaa | atc | cgg | gag | gaa | gcc | ttt | gta | agc | caa | 1872 |
| Leu | Phe | Tyr | Cys | Leu | His | Glu | Ile | Arg | Glu | Glu | Ala | Phe | Val | Ser | Gln | |
| | | | | 610 | | | | | 615 | | | | | 620 | | |
| gcc | cta | aat | gat | tat | cat | aaa | gtt | gtc | ttg | aga | att | ggc | aac | aac | aaa | 1920 |
| Ala | Leu | Asn | Asp | Tyr | His | Lys | Val | Val | Leu | Arg | Ile | Gly | Asn | Asn | Lys | |
| 625 | | | | | 630 | | | | | 635 | | | | | 640 | |
| gaa | gtt | caa | gtg | tct | gct | ttt | tgc | ctg | aag | cgg | tgt | caa | tat | ttg | cat | 1968 |
| Glu | Val | Gln | Val | Ser | Ala | Phe | Cys | Leu | Lys | Arg | Cys | Gln | Tyr | Leu | His | |
| | | | | 645 | | | | | 650 | | | | | 655 | | |
| gag | gtg | gaa | ctg | acc | gtc | acc | ctg | aac | ttc | atg | aac | gtg | tgg | aag | ctc | 2016 |
| Glu | Val | Glu | Leu | Thr | Val | Thr | Leu | Asn | Phe | Met | Asn | Val | Trp | Lys | Leu | |
| | | | | 660 | | | | | 665 | | | | | 670 | | |
| agc | tcc | agc | tcc | cat | cct | ggc | tct | gag | taa | | | | | | | 2046 |
| Ser | Ser | Ser | Ser | His | Pro | Gly | Ser | Glu | | | | | | | | |
| | | | 675 | | | | | 680 | | | | | | | | |

<210> SEQ ID NO 20
<211> LENGTH: 681
<212> TYPE: PRT
<213> ORGANISM: Homo sapien

<400> SEQUENCE: 20

Met Ser Asp Val Asn Pro Pro Ser Asp Thr Pro Ile Pro Phe Ser Ser
1               5                   10                  15

Ser Ser Thr His Ser Ser His Ile Pro Pro Trp Thr Phe Ser Cys Tyr
            20                  25                  30

Pro Gly Ser Pro Cys Glu Asn Gly Val Met Leu Tyr Met Arg Asn Val
        35                  40                  45

Ser His Glu Glu Leu Gln Arg Phe Lys Gln Leu Leu Leu Thr Glu Leu
    50                  55                  60

Ser Thr Gly Thr Met Pro Ile Thr Trp Asp Gln Val Glu Thr Ala Ser
65                  70                  75                  80

Trp Ala Glu Val Val His Leu Leu Ile Glu Arg Phe Pro Gly Arg Arg
                85                  90                  95

Ala Trp Asp Val Thr Ser Asn Ile Phe Ala Ile Met Asn Cys Asp Lys
            100                 105                 110

Met Cys Val Val Val Arg Arg Glu Ile Asn Ala Ile Leu Pro Thr Leu
        115                 120                 125

-continued

```
Glu Pro Glu Asp Leu Asn Val Gly Glu Thr Gln Val Asn Leu Glu Glu
    130                 135                 140

Gly Glu Ser Gly Lys Ile Arg Arg Tyr Lys Ser Asn Val Met Glu Lys
145                 150                 155                 160

Phe Phe Pro Ile Trp Asp Ile Thr Thr Trp Pro Gly Asn Gln Arg Asp
                165                 170                 175

Phe Phe Tyr Gln Gly Val His Arg His Glu Glu Tyr Leu Pro Cys Leu
                180                 185                 190

Leu Leu Pro Lys Arg Pro Gln Gly Arg Gln Pro Lys Thr Val Ala Ile
                195                 200                 205

Gln Gly Ala Pro Gly Ile Gly Lys Thr Ile Leu Ala Lys Lys Val Met
    210                 215                 220

Phe Glu Trp Ala Arg Asn Lys Phe Tyr Ala His Lys Arg Trp Cys Ala
225                 230                 235                 240

Phe Tyr Phe His Cys Gln Glu Val Asn Gln Thr Thr Asp Gln Ser Phe
                245                 250                 255

Ser Glu Leu Ile Glu Gln Lys Trp Pro Gly Ser Gln Asp Leu Val Ser
                260                 265                 270

Lys Ile Met Ser Lys Pro Asp Gln Leu Leu Leu Leu Asp Gly Phe
                275                 280                 285

Glu Glu Leu Thr Ser Thr Leu Ile Asp Arg Leu Glu Asp Leu Ser Glu
    290                 295                 300

Asp Trp Arg Gln Lys Leu Pro Gly Ser Val Leu Leu Ser Ser Leu Leu
305                 310                 315                 320

Ser Lys Thr Met Leu Pro Glu Ala Thr Leu Leu Ile Met Ile Arg Phe
                325                 330                 335

Thr Ser Trp Gln Thr Cys Lys Pro Leu Leu Lys Cys Pro Ser Leu Val
                340                 345                 350

Thr Leu Pro Gly Phe Asn Thr Met Glu Lys Ile Lys Tyr Phe Gln Met
                355                 360                 365

Tyr Phe Gly His Thr Glu Glu Gly Asp Gln Val Leu Ser Phe Ala Met
    370                 375                 380

Glu Asn Thr Ile Leu Phe Ser Met Cys Arg Val Pro Val Val Cys Trp
385                 390                 395                 400

Met Val Cys Ser Gly Leu Lys Gln Gln Met Glu Arg Gly Asn Asn Leu
                405                 410                 415

Thr Gln Ser Cys Pro Asn Ala Thr Ser Val Phe Val Arg Tyr Ile Ser
                420                 425                 430

Ser Leu Phe Pro Thr Arg Ala Glu Asn Phe Ser Arg Lys Ile His Gln
                435                 440                 445

Ala Gln Leu Glu Gly Leu Cys His Leu Ala Ala Asp Ser Met Trp His
    450                 455                 460

Arg Lys Trp Val Leu Gly Lys Glu Asp Leu Glu Glu Ala Lys Leu Asp
465                 470                 475                 480

Gln Thr Gly Val Thr Ala Phe Leu Gly Met Ser Ile Leu Arg Arg Ile
                485                 490                 495

Ala Gly Glu Glu Asp His Tyr Val Phe Thr Leu Val Thr Phe Gln Glu
                500                 505                 510

Phe Phe Ala Ala Leu Phe Tyr Val Leu Cys Phe Pro Gln Arg Leu Lys
                515                 520                 525

Asn Phe His Val Leu Ser His Val Asn Ile Gln Arg Leu Ile Ala Ser
                530                 535                 540
```

```
Pro Arg Gly Ser Lys Ser Tyr Leu Ser His Met Gly Leu Phe Leu Phe
545                 550                 555                 560

Gly Phe Leu Asn Glu Ala Cys Ala Ser Ala Val Glu Gln Ser Phe Gln
                565                 570                 575

Cys Lys Val Ser Phe Gly Asn Lys Arg Lys Leu Leu Lys Val Ile Pro
            580                 585                 590

Leu Leu His Lys Cys Asp Pro Pro Ser Pro Gly Ser Gly Val Pro Gln
        595                 600                 605

Leu Phe Tyr Cys Leu His Glu Ile Arg Glu Glu Ala Phe Val Ser Gln
    610                 615                 620

Ala Leu Asn Asp Tyr His Lys Val Val Leu Arg Ile Gly Asn Asn Lys
625                 630                 635                 640

Glu Val Gln Val Ser Ala Phe Cys Leu Lys Arg Cys Gln Tyr Leu His
                645                 650                 655

Glu Val Glu Leu Thr Val Thr Leu Asn Phe Met Asn Val Trp Lys Leu
                660                 665                 670

Ser Ser Ser Ser His Pro Gly Ser Glu
        675                 680
```

<210> SEQ ID NO 21
<211> LENGTH: 1515
<212> TYPE: DNA
<213> ORGANISM: Homo sapien
<220> FEATURE:
<221> NAME/KEY: CDS
<222> LOCATION: (1)...(1512)

<400> SEQUENCE: 21

```
atg gcc atg gcc aag gcc aga aag ccc cgg gag gca ttg ctc tgg gcc      48
Met Ala Met Ala Lys Ala Arg Lys Pro Arg Glu Ala Leu Leu Trp Ala
1               5                   10                  15 ttg agt gac ctt gag gag aac gat ttc aag aag tta aag ttc tac tta     96
Leu Ser Asp Leu Glu Glu Asn Asp Phe Lys Lys Leu Lys Phe Tyr Leu
                20                  25                  30 cgg gat atg acc ctg tct gag ggc cag ccc cca ctg gcc aga ggg gag    144
Arg Asp Met Thr Leu Ser Glu Gly Gln Pro Pro Leu Ala Arg Gly Glu
            35                  40                  45 ttg gag ggc ctg att ccg gtg gac ctg gca gaa tta ctg att tca aag    192
Leu Glu Gly Leu Ile Pro Val Asp Leu Ala Glu Leu Leu Ile Ser Lys
        50                  55                  60 tat gga gaa aag gag gct gtg aaa gtt gtc ctc aag ggc ttg aag gtc    240
Tyr Gly Glu Lys Glu Ala Val Lys Val Val Leu Lys Gly Leu Lys Val
65                  70                  75                  80 atg aac ctg ttg gaa ctt gtg gac cag ctc agc cat att tgt ctg cat    288
Met Asn Leu Leu Glu Leu Val Asp Gln Leu Ser His Ile Cys Leu His
                85                  90                  95 ggg gtc ggc tgg cac tgg aaa gac aac tct cgc cag aaa aag gtg ttg    336
Gly Val Gly Trp His Trp Lys Asp Asn Ser Arg Gln Lys Lys Val Leu
            100                 105                 110 gac tgg gcc acc ggt act ctg tac cca ggc cgg ttt gat tat gtc ttt    384
Asp Trp Ala Thr Gly Thr Leu Tyr Pro Gly Arg Phe Asp Tyr Val Phe
        115                 120                 125 tat gta agc tgc aaa gaa gtg gtc ctg ctg gag agc aaa ctg gag        432
Tyr Val Ser Cys Lys Glu Val Val Leu Leu Glu Ser Lys Leu Glu
    130                 135                 140 cag ctc ctt ttc tgg tgc tgc ggg gac aat caa gcc cct gtc aca gag    480
Gln Leu Leu Phe Trp Cys Cys Gly Asp Asn Gln Ala Pro Val Thr Glu
145                 150                 155                 160
```

-continued

| | |
|---|---|
| att ctg agg cag cca gag cgg ctc ctg ttc atc ctg gat ggc ttt gat<br>Ile Leu Arg Gln Pro Glu Arg Leu Leu Phe Ile Leu Asp Gly Phe Asp<br>165                                   170                       175 | 528 |
| gag ctg cag agg ccc ttt gaa gaa aag ttg aag aag agg ggt ttg agt<br>Glu Leu Gln Arg Pro Phe Glu Glu Lys Leu Lys Lys Arg Gly Leu Ser<br>           180                           185                     190 | 576 |
| ccc aag gag agc ctg ctg cac ctt cta att agg aga cat aca ctc ccc<br>Pro Lys Glu Ser Leu Leu His Leu Leu Ile Arg Arg His Thr Leu Pro<br>          195                         200                    205 | 624 |
| acg tgc tcc ctt ctc atc acc acc cgg ccc ctg gct ttg agg aat ctg<br>Thr Cys Ser Leu Leu Ile Thr Thr Arg Pro Leu Ala Leu Arg Asn Leu<br>210                                  215                       220 | 672 |
| gag ccc ttg ctg aaa caa gca cgt cat gtc cat atc cta ggc ttc tct<br>Glu Pro Leu Leu Lys Gln Ala Arg His Val His Ile Leu Gly Phe Ser<br>225                                230                      235                    240 | 720 |
| gag gag gag agg gcg agg tac ttc agc tcc tat ttc acg gat gag aag<br>Glu Glu Glu Arg Ala Arg Tyr Phe Ser Ser Tyr Phe Thr Asp Glu Lys<br>                       245                      250                      255 | 768 |
| caa gct gac cgt gcc ttc gac att gta cag aaa aat gac att ctc tac<br>Gln Ala Asp Arg Ala Phe Asp Ile Val Gln Lys Asn Asp Ile Leu Tyr<br>           260                          265                    270 | 816 |
| aaa gcg tgt cag gtt cca ggc att tgc tgg gtg gtc tgc tcc tgg ctg<br>Lys Ala Cys Gln Val Pro Gly Ile Cys Trp Val Val Cys Ser Trp Leu<br>         275                        280                    285 | 864 |
| cag ggg cag atg gag aga ggc aaa gtt gtc tta gag aca cct aga aac<br>Gln Gly Gln Met Glu Arg Gly Lys Val Val Leu Glu Thr Pro Arg Asn<br>         290                        295                    300 | 912 |
| agc act gac atc ttc atg gct tac gtc tcc acc ttt ctg ccg ccc gat<br>Ser Thr Asp Ile Phe Met Ala Tyr Val Ser Thr Phe Leu Pro Pro Asp<br>305                                310                      315                  320 | 960 |
| gat gat ggg ggc tgc tcc gag ctt tcc cgg cac agg gtc ctg agg agt<br>Asp Asp Gly Gly Cys Ser Glu Leu Ser Arg His Arg Val Leu Arg Ser<br>                       325                      330                    335 | 1008 |
| ctg tgc tcc cta gca gct gaa ggg att cag cac cag agg ttc cta ttt<br>Leu Cys Ser Leu Ala Ala Glu Gly Ile Gln His Gln Arg Phe Leu Phe<br>           340                          345                    350 | 1056 |
| gaa gaa gct gag ctc agg aaa cat aat tta gat ggc ccc agg ctt gcc<br>Glu Glu Ala Glu Leu Arg Lys His Asn Leu Asp Gly Pro Arg Leu Ala<br>         355                        360                    365 | 1104 |
| gct ttc ctg agt agt aac gac tac caa ttg gga ctt gcc atc aag aag<br>Ala Phe Leu Ser Ser Asn Asp Tyr Gln Leu Gly Leu Ala Ile Lys Lys<br>370                                375                    380 | 1152 |
| ttc tac agc ttc cgc cac atc agc ttc cag gac ttt ttt cat gcc atg<br>Phe Tyr Ser Phe Arg His Ile Ser Phe Gln Asp Phe Phe His Ala Met<br>385                                390                    395                  400 | 1200 |
| tct tac ctg gtg aaa gag gac caa agc cgg ctg ggg aag gag tcc cgc<br>Ser Tyr Leu Val Lys Glu Asp Gln Ser Arg Leu Gly Lys Glu Ser Arg<br>           405                          410                    415 | 1248 |
| aga gaa gtg caa agg ctg ctg gag gta aag gag cag gaa ggg aat gat<br>Arg Glu Val Gln Arg Leu Leu Glu Val Lys Glu Gln Glu Gly Asn Asp<br>                       420                      425                    430 | 1296 |
| gag atg acc ctc act atg cag ttt tta ctg gac atc tcg aaa aaa gac<br>Glu Met Thr Leu Thr Met Gln Phe Leu Leu Asp Ile Ser Lys Lys Asp<br>           435                          440                    445 | 1344 |
| agc ttc tcg aac ttg gag ctc aag ttc tgc ttc aga att tct ccc tgt<br>Ser Phe Ser Asn Leu Glu Leu Lys Phe Cys Phe Arg Ile Ser Pro Cys<br>         450                        455                    460 | 1392 |
| tta gcg cag gat ctg aag cat ttt aaa gaa cag atg gaa tct atg aag<br>Leu Ala Gln Asp Leu Lys His Phe Lys Glu Gln Met Glu Ser Met Lys<br>465                                470                    475                  480 | 1440 |

-continued

```
cac aac agg acc tgg gat ttg gaa ttc tcc ctg tat gaa gct aaa ata        1488
His Asn Arg Thr Trp Asp Leu Glu Phe Ser Leu Tyr Glu Ala Lys Ile
                485                 490                 495 aag aat ctg gta aaa gta ttc aga tga                                    1515
Lys Asn Leu Val Lys Val Phe Arg
            500
```

<210> SEQ ID NO 22
<211> LENGTH: 504
<212> TYPE: PRT
<213> ORGANISM: Homo sapien

<400> SEQUENCE: 22

```
Met Ala Met Ala Lys Ala Arg Lys Pro Arg Glu Ala Leu Leu Trp Ala
 1               5                  10                  15

Leu Ser Asp Leu Glu Glu Asn Asp Phe Lys Lys Leu Lys Phe Tyr Leu
                20                  25                  30

Arg Asp Met Thr Leu Ser Glu Gly Gln Pro Pro Leu Ala Arg Gly Glu
            35                  40                  45

Leu Glu Gly Leu Ile Pro Val Asp Leu Ala Glu Leu Leu Ile Ser Lys
        50                  55                  60

Tyr Gly Glu Lys Glu Ala Val Lys Val Val Leu Lys Gly Leu Lys Val
 65                 70                  75                  80

Met Asn Leu Leu Glu Leu Val Asp Gln Leu Ser His Ile Cys Leu His
                85                  90                  95

Gly Val Gly Trp His Trp Lys Asp Asn Ser Arg Gln Lys Lys Val Leu
                100                 105                 110

Asp Trp Ala Thr Gly Thr Leu Tyr Pro Gly Arg Phe Asp Tyr Val Phe
            115                 120                 125

Tyr Val Ser Cys Lys Glu Val Val Leu Leu Glu Ser Lys Leu Glu
        130                 135                 140

Gln Leu Leu Phe Trp Cys Cys Gly Asp Asn Gln Ala Pro Val Thr Glu
145                 150                 155                 160

Ile Leu Arg Gln Pro Glu Arg Leu Leu Phe Ile Leu Asp Gly Phe Asp
                165                 170                 175

Glu Leu Gln Arg Pro Phe Glu Glu Lys Leu Lys Lys Arg Gly Leu Ser
            180                 185                 190

Pro Lys Glu Ser Leu Leu His Leu Leu Ile Arg Arg His Thr Leu Pro
        195                 200                 205

Thr Cys Ser Leu Leu Ile Thr Thr Arg Pro Leu Ala Leu Arg Asn Leu
    210                 215                 220

Glu Pro Leu Leu Lys Gln Ala Arg His Val His Ile Leu Gly Phe Ser
225                 230                 235                 240

Glu Glu Glu Arg Ala Arg Tyr Phe Ser Ser Tyr Phe Thr Asp Glu Lys
                245                 250                 255

Gln Ala Asp Arg Ala Phe Asp Ile Val Gln Lys Asn Asp Ile Leu Tyr
            260                 265                 270

Lys Ala Cys Gln Val Pro Gly Ile Cys Trp Val Val Cys Ser Trp Leu
        275                 280                 285

Gln Gly Gln Met Glu Arg Gly Lys Val Val Leu Glu Thr Pro Arg Asn
    290                 295                 300

Ser Thr Asp Ile Phe Met Ala Tyr Val Ser Thr Phe Leu Pro Pro Asp
305                 310                 315                 320

Asp Asp Gly Gly Cys Ser Glu Leu Ser Arg His Arg Val Leu Arg Ser
                325                 330                 335
```

```
Leu Cys Ser Leu Ala Ala Glu Gly Ile Gln His Gln Arg Phe Leu Phe
            340                 345                 350

Glu Glu Ala Glu Leu Arg Lys His Asn Leu Asp Gly Pro Arg Leu Ala
            355                 360                 365

Ala Phe Leu Ser Ser Asn Asp Tyr Gln Leu Gly Leu Ala Ile Lys Lys
        370                 375                 380

Phe Tyr Ser Phe Arg His Ile Ser Phe Gln Asp Phe His Ala Met
385                 390                 395                 400

Ser Tyr Leu Val Lys Glu Asp Gln Ser Arg Leu Gly Lys Glu Ser Arg
                405                 410                 415

Arg Glu Val Gln Arg Leu Leu Glu Val Lys Glu Gln Glu Gly Asn Asp
            420                 425                 430

Glu Met Thr Leu Thr Met Gln Phe Leu Leu Asp Ile Ser Lys Lys Asp
            435                 440                 445

Ser Phe Ser Asn Leu Glu Leu Lys Phe Cys Phe Arg Ile Ser Pro Cys
        450                 455                 460

Leu Ala Gln Asp Leu Lys His Phe Lys Glu Gln Met Glu Ser Met Lys
465                 470                 475                 480

His Asn Arg Thr Trp Asp Leu Glu Phe Ser Leu Tyr Glu Ala Lys Ile
                485                 490                 495

Lys Asn Leu Val Lys Val Phe Arg
            500

<210> SEQ ID NO 23
<211> LENGTH: 3108
<212> TYPE: DNA
<213> ORGANISM: Homo sapien
<220> FEATURE:
<221> NAME/KEY: CDS
<222> LOCATION: (1)...(3105)

<400> SEQUENCE: 23 atg cta cga acc gca ggc agg gac ggc ctc tgt cgc ctg tcc acc tac      48
Met Leu Arg Thr Ala Gly Arg Asp Gly Leu Cys Arg Leu Ser Thr Tyr
 1               5                  10                  15 ttg gaa gaa ctc gag gct gtg gaa ctg aag aag ttc aag tta tac ctg      96
Leu Glu Glu Leu Glu Ala Val Glu Leu Lys Lys Phe Lys Leu Tyr Leu
            20                  25                  30 ggg acc gcg aca gag ctg gga gaa ggc aag atc ccc tgg gga agc atg     144
Gly Thr Ala Thr Glu Leu Gly Glu Gly Lys Ile Pro Trp Gly Ser Met
        35                  40                  45 gag aag gcc ggt ccc ctg gaa atg gcc cag ctg ctc atc acc cac ttc     192
Glu Lys Ala Gly Pro Leu Glu Met Ala Gln Leu Leu Ile Thr His Phe
    50                  55                  60 ggg cca gag gag gcc tgg agg ttg gct ctc agc acc ttt gag cgg ata     240
Gly Pro Glu Glu Ala Trp Arg Leu Ala Leu Ser Thr Phe Glu Arg Ile
 65                  70                  75                  80 aac agg aag gac ctg tgg gag aga gga cag aga gag gac ctg gtg agg     288
Asn Arg Lys Asp Leu Trp Glu Arg Gly Gln Arg Glu Asp Leu Val Arg
                 85                  90                  95 gat ccc cag gaa acc tac agg gac tat gtc cgc agg aaa ttc cgg ctc     336
Asp Pro Gln Glu Thr Tyr Arg Asp Tyr Val Arg Arg Lys Phe Arg Leu
            100                 105                 110 atg gaa gac cgc aat gcg cgc cta ggg gaa tgt gtc aac ctc agc cac     384
Met Glu Asp Arg Asn Ala Arg Leu Gly Glu Cys Val Asn Leu Ser His
        115                 120                 125 cgg tac acc cgg ctc ctg ctg gtg aag gag cac tca aac ccc atg cag     432
Arg Tyr Thr Arg Leu Leu Leu Val Lys Glu His Ser Asn Pro Met Gln
    130                 135                 140
```

-continued

| | | |
|---|---|---|
| gtc cag cag cag ctt ctg gac aca ggc cgg gga cac gcg agg acc gtg<br>Val Gln Gln Gln Leu Leu Asp Thr Gly Arg Gly His Ala Arg Thr Val<br>145                          150                     155                   160 | 480 |
| gga cac cag gct agc ccc atc aag ata gag acc ctc ttt gag cca gac<br>Gly His Gln Ala Ser Pro Ile Lys Ile Glu Thr Leu Phe Glu Pro Asp<br>                 165                   170                   175 | 528 |
| gag gag cgc ccc gag cca ccg cgc acc gtg gtc atg caa ggc gcg gca<br>Glu Glu Arg Pro Glu Pro Pro Arg Thr Val Val Met Gln Gly Ala Ala<br>        180                       185                   190 | 576 |
| ggg ata ggc aag tcc atg ctg gca cac aag gtg atg ctg gac tgg gcg<br>Gly Ile Gly Lys Ser Met Leu Ala His Lys Val Met Leu Asp Trp Ala<br>               195                   200                   205 | 624 |
| gac ggg aag ctc ttc caa ggc aga ttt gat tat ctc ttc tac atc aac<br>Asp Gly Lys Leu Phe Gln Gly Arg Phe Asp Tyr Leu Phe Tyr Ile Asn<br>210                          215                     220 | 672 |
| tgc agg gag atg aac cag agt gcc acg gaa tgc agc atg caa gac ctc<br>Cys Arg Glu Met Asn Gln Ser Ala Thr Glu Cys Ser Met Gln Asp Leu<br>225                          230                     235                   240 | 720 |
| atc ttc agc tgc tgg cct gag ccc agc gcg cct ctc cag gag ctc atc<br>Ile Phe Ser Cys Trp Pro Glu Pro Ser Ala Pro Leu Gln Glu Leu Ile<br>                        245                     250                   255 | 768 |
| cga gtt ccc gag cgc ctc ctt ttc atc atc gac ggc ttc gat gag ctc<br>Arg Val Pro Glu Arg Leu Leu Phe Ile Ile Asp Gly Phe Asp Glu Leu<br>                260                   265                   270 | 816 |
| aag cct tct ttc cac gat cct cag gga ccc tgg tgc ctc tgc tgg gag<br>Lys Pro Ser Phe His Asp Pro Gln Gly Pro Trp Cys Leu Cys Trp Glu<br>        275                       280                   285 | 864 |
| gag aaa cgg ccc acg gag ctg ctt ctt aac agc tta att cgg aag aag<br>Glu Lys Arg Pro Thr Glu Leu Leu Leu Asn Ser Leu Ile Arg Lys Lys<br>               290                   295                   300 | 912 |
| ctg ctc cct gag cta tct ttg ctc atc acc aca cgg ccc acg gct ttg<br>Leu Leu Pro Glu Leu Ser Leu Leu Ile Thr Thr Arg Pro Thr Ala Leu<br>305                          310                     315                   320 | 960 |
| gag aag ctc cac cgt ctg ctg gag cac ccc agg cat gtg gag atc ctg<br>Glu Lys Leu His Arg Leu Leu Glu His Pro Arg His Val Glu Ile Leu<br>                 325                   330                   335 | 1008 |
| ggc ttc tct gag gca gaa agg aag gaa tac ttc tac aag tat ttc cac<br>Gly Phe Ser Glu Ala Glu Arg Lys Glu Tyr Phe Tyr Lys Tyr Phe His<br>                        340                     345                   350 | 1056 |
| aat gca gag cag gcg ggc caa gtc ttc aat tac gtg agg gac aac gag<br>Asn Ala Glu Gln Ala Gly Gln Val Phe Asn Tyr Val Arg Asp Asn Glu<br>        355                       360                   365 | 1104 |
| cct ctc ttc acc atg tgc ttc gtc ccc ctg gtg tgc tgg gtg gtg tgt<br>Pro Leu Phe Thr Met Cys Phe Val Pro Leu Val Cys Trp Val Val Cys<br>370                          375                     380 | 1152 |
| acc tgc ctc cag cag cag ctg gag ggt ggg ggg ctg ttg aga cag acg<br>Thr Cys Leu Gln Gln Gln Leu Glu Gly Gly Gly Leu Leu Arg Gln Thr<br>385                          390                     395                   400 | 1200 |
| tcc agg acc acc act gca gtg tac atg ctc tac ctg ctg agt ctg atg<br>Ser Arg Thr Thr Thr Ala Val Tyr Met Leu Tyr Leu Leu Ser Leu Met<br>                        405                     410                   415 | 1248 |
| caa ccc aag ccg ggg gcc ccg cgc ctc cag ccc cca ccc aac cag aga<br>Gln Pro Lys Pro Gly Ala Pro Arg Leu Gln Pro Pro Pro Asn Gln Arg<br>        420                       425                   430 | 1296 |
| ggg ttg tgc tcc ttg gcg gca gat ggg ctc tgg aat cag aaa atc cta<br>Gly Leu Cys Ser Leu Ala Ala Asp Gly Leu Trp Asn Gln Lys Ile Leu<br>               435                   440                   445 | 1344 |
| ttt gag gag cag gac ctc cgg aag cac ggc cta gac ggg gaa gac gtc<br>Phe Glu Glu Gln Asp Leu Arg Lys His Gly Leu Asp Gly Glu Asp Val<br>450                          455                     460 | 1392 |

```
tct gcc ttc ctc aac atg aac atc ttc cag aag gac atc aac tgt gag    1440
Ser Ala Phe Leu Asn Met Asn Ile Phe Gln Lys Asp Ile Asn Cys Glu
465                 470                 475                 480 agg tac tac agc ttc atc cac ttg agt ttc cag gaa ttc ttt gca gct    1488
Arg Tyr Tyr Ser Phe Ile His Leu Ser Phe Gln Glu Phe Phe Ala Ala
                    485                 490                 495 atg tac tat atc ctg gac gag ggg gag ggc ggg gca ggc cca gac cag    1536
Met Tyr Tyr Ile Leu Asp Glu Gly Glu Gly Gly Ala Gly Pro Asp Gln
                500                 505                 510 gac gtg acc agg ctg ttg acc gag tac gcg ttt tct gaa agg agc ttc    1584
Asp Val Thr Arg Leu Leu Thr Glu Tyr Ala Phe Ser Glu Arg Ser Phe
            515                 520                 525 ctg gca ctc acc agc cgc ttc ctg ttt gga ctc ctg aac gag gag acc    1632
Leu Ala Leu Thr Ser Arg Phe Leu Phe Gly Leu Leu Asn Glu Glu Thr
530                 535                 540 agg agc cac ctg gag aag agt ctc tgc tgg aag gtc tcg ccg cac atc    1680
Arg Ser His Leu Glu Lys Ser Leu Cys Trp Lys Val Ser Pro His Ile
545                 550                 555                 560 aag atg gac ctg ttg cag tgg atc caa agc aaa gct cag agc gac ggc    1728
Lys Met Asp Leu Leu Gln Trp Ile Gln Ser Lys Ala Gln Ser Asp Gly
                565                 570                 575 tcc acc ctg cag cag ggc tcc ttg gag ttc ttc agc tgc ttg tac gag    1776
Ser Thr Leu Gln Gln Gly Ser Leu Glu Phe Phe Ser Cys Leu Tyr Glu
                580                 585                 590 atc cag gag gag gag ttt atc cag cag gcc ctg agc cac ttc cag gtg    1824
Ile Gln Glu Glu Glu Phe Ile Gln Gln Ala Leu Ser His Phe Gln Val
                595                 600                 605 atc gtg gtc agc aac att gcc tcc aag atg gag cac atg gtc tcc tcg    1872
Ile Val Val Ser Asn Ile Ala Ser Lys Met Glu His Met Val Ser Ser
610                 615                 620 ttc tgt ctg aag cgc tgc agg agc gcc cag gtg ctg cac ttg tat ggc    1920
Phe Cys Leu Lys Arg Cys Arg Ser Ala Gln Val Leu His Leu Tyr Gly
625                 630                 635                 640 gcc acc tac agc gcg gac ggg gaa gac cgc gcg agg tgc tcc gca gga    1968
Ala Thr Tyr Ser Ala Asp Gly Glu Asp Arg Ala Arg Cys Ser Ala Gly
                645                 650                 655 gcg cac acg ctg ttg gtg cag ctc aga cca gag agg acc gtt ctg ctg    2016
Ala His Thr Leu Leu Val Gln Leu Arg Pro Glu Arg Thr Val Leu Leu
                660                 665                 670 gac gcc tac agt gaa cat ctg gca gcg gcc ctg tgc acc aat cca aac    2064
Asp Ala Tyr Ser Glu His Leu Ala Ala Ala Leu Cys Thr Asn Pro Asn
            675                 680                 685 ctg ata gag ctg tct ctg tac cga aat gcc ctg ggc agc cgg ggg gtg    2112
Leu Ile Glu Leu Ser Leu Tyr Arg Asn Ala Leu Gly Ser Arg Gly Val
690                 695                 700 aag ctg ctc tgt caa gga ctc aga cac ccc aac tgc aaa ctt cag aac    2160
Lys Leu Leu Cys Gln Gly Leu Arg His Pro Asn Cys Lys Leu Gln Asn
705                 710                 715                 720 ctg agg ctg aag agg tgc cgc atc tcc agc tca gcc tgc gag gac ctc    2208
Leu Arg Leu Lys Arg Cys Arg Ile Ser Ser Ser Ala Cys Glu Asp Leu
                725                 730                 735 tct gca gct ctc ata gcc aat aag aat ttg aca agg atg gat ctc agt    2256
Ser Ala Ala Leu Ile Ala Asn Lys Asn Leu Thr Arg Met Asp Leu Ser
                740                 745                 750 ggc aac ggc gtt gga ttc cca ggc atg atg ctg ctt tgc gag ggc ctg    2304
Gly Asn Gly Val Gly Phe Pro Gly Met Met Leu Leu Cys Glu Gly Leu
                755                 760                 765 cgg cat ccc cag tgc agg ctg cag atg att cag ttg agg aag tgt cag    2352
Arg His Pro Gln Cys Arg Leu Gln Met Ile Gln Leu Arg Lys Cys Gln
                770                 775                 780
```

| | | |
|---|---|---|
| ctg gag tcc ggg gct tgt cag gag atg gct tct gtg ctc ggc acc aac<br>Leu Glu Ser Gly Ala Cys Gln Glu Met Ala Ser Val Leu Gly Thr Asn<br>785                    790                    795                800 | 2400 |
| cca cat ctg gtt gag ttg gac ctg aca gga aat gca ctg gag gat ttg<br>Pro His Leu Val Glu Leu Asp Leu Thr Gly Asn Ala Leu Glu Asp Leu<br>                    805                    810                    815 | 2448 |
| ggc ctg agg tta cta tgc cag gga ctg agg cac cca gtc tgc aga cta<br>Gly Leu Arg Leu Leu Cys Gln Gly Leu Arg His Pro Val Cys Arg Leu<br>        820                    825                    830 | 2496 |
| cgg act ttg tgg ctg aag atc tgc cgc ctc act gct gct gcc tgt gac<br>Arg Thr Leu Trp Leu Lys Ile Cys Arg Leu Thr Ala Ala Ala Cys Asp<br>835                    840                    845 | 2544 |
| gag ctg gcc tca act ctc agt gtg aac cag agc ctg aga gag ctg gac<br>Glu Leu Ala Ser Thr Leu Ser Val Asn Gln Ser Leu Arg Glu Leu Asp<br>        850                    855                    860 | 2592 |
| ctg agc ctg aat gag ctg ggg gac ctc ggg gtg ctg ctg tgt gag<br>Leu Ser Leu Asn Glu Leu Gly Asp Leu Gly Val Leu Leu Cys Glu<br>865                    870                    875                880 | 2640 |
| ggc ctc agg cat ccc acg tgc aag ctc cag acc ctg cgg ttg ggc atc<br>Gly Leu Arg His Pro Thr Cys Lys Leu Gln Thr Leu Arg Leu Gly Ile<br>                885                    890                    895 | 2688 |
| tgc cgg ctg ggc tct gcc gcc tgt gag ggt ctt tct gtg gtg ctc cag<br>Cys Arg Leu Gly Ser Ala Ala Cys Glu Gly Leu Ser Val Val Leu Gln<br>        900                    905                    910 | 2736 |
| gcc aac cac aac ctc cgg gag ctg gac ttg agt ttc aac gac ctg gga<br>Ala Asn His Asn Leu Arg Glu Leu Asp Leu Ser Phe Asn Asp Leu Gly<br>915                    920                    925 | 2784 |
| gac tgg ggc ctg tgg ttg ctg gct gag ggg ctg caa cat ccc gcc tgc<br>Asp Trp Gly Leu Trp Leu Leu Ala Glu Gly Leu Gln His Pro Ala Cys<br>930                    935                    940 | 2832 |
| aga ctc cag aaa ctg tgg ctg gat agc tgt ggc ctc aca gcc aag gct<br>Arg Leu Gln Lys Leu Trp Leu Asp Ser Cys Gly Leu Thr Ala Lys Ala<br>945                    950                    955                960 | 2880 |
| tgt gag aat ctt tac ttc acc ctg ggg atc aac cag acc ttg acc gac<br>Cys Glu Asn Leu Tyr Phe Thr Leu Gly Ile Asn Gln Thr Leu Thr Asp<br>                965                    970                    975 | 2928 |
| ctt tac ctg acc aac aac gcc cta ggg gac aca ggt gtc cga ctg ctt<br>Leu Tyr Leu Thr Asn Asn Ala Leu Gly Asp Thr Gly Val Arg Leu Leu<br>        980                    985                    990 | 2976 |
| tgc aag cgg ctg agc cat cct ggc tgc aaa ctc gga gtc ctc tgg tta<br>Cys Lys Arg Leu Ser His Pro Gly Cys Lys Leu Arg Val Leu Trp Leu<br>            995                    1000                  1005 | 3024 |
| ttt ggg atg gac ctg aat aaa atg acc cac agt agg ttg gca gcg ctt<br>Phe Gly Met Asp Leu Asn Lys Met Thr His Ser Arg Leu Ala Ala Leu<br>1010                    1015                    1020 | 3072 |
| cga gta aca aaa cct tat ttg gac att ggc tgc tga<br>Arg Val Thr Lys Pro Tyr Leu Asp Ile Gly Cys<br>1025                    1030                    1035 | 3108 |

<210> SEQ ID NO 24
<211> LENGTH: 1035
<212> TYPE: PRT
<213> ORGANISM: Homo sapien

<400> SEQUENCE: 24

Met Leu Arg Thr Ala Gly Arg Asp Gly Leu Cys Arg Leu Ser Thr Tyr
1                5                    10                  15

Leu Glu Glu Leu Glu Ala Val Glu Leu Lys Lys Phe Lys Leu Tyr Leu
                20                    25                    30

```
Gly Thr Ala Thr Glu Leu Gly Glu Gly Lys Ile Pro Trp Gly Ser Met
         35                  40                  45
Glu Lys Ala Gly Pro Leu Glu Met Ala Gln Leu Leu Ile Thr His Phe
 50                  55                  60
Gly Pro Glu Glu Ala Trp Arg Leu Ala Leu Ser Thr Phe Glu Arg Ile
 65                  70                  75                  80
Asn Arg Lys Asp Leu Trp Glu Arg Gly Gln Arg Glu Asp Leu Val Arg
                 85                  90                  95
Asp Pro Gln Glu Thr Tyr Arg Asp Tyr Val Arg Arg Lys Phe Arg Leu
             100                 105                 110
Met Glu Asp Arg Asn Ala Arg Leu Gly Glu Cys Val Asn Leu Ser His
             115                 120                 125
Arg Tyr Thr Arg Leu Leu Leu Val Lys Glu His Ser Asn Pro Met Gln
         130                 135                 140
Val Gln Gln Gln Leu Leu Asp Thr Gly Arg Gly His Ala Arg Thr Val
145                 150                 155                 160
Gly His Gln Ala Ser Pro Ile Lys Ile Glu Thr Leu Phe Glu Pro Asp
                 165                 170                 175
Glu Glu Arg Pro Glu Pro Pro Arg Thr Val Val Met Gln Gly Ala Ala
             180                 185                 190
Gly Ile Gly Lys Ser Met Leu Ala His Lys Val Met Leu Asp Trp Ala
         195                 200                 205
Asp Gly Lys Leu Phe Gln Gly Arg Phe Asp Tyr Leu Phe Tyr Ile Asn
         210                 215                 220
Cys Arg Glu Met Asn Gln Ser Ala Thr Glu Cys Ser Met Gln Asp Leu
225                 230                 235                 240
Ile Phe Ser Cys Trp Pro Glu Pro Ser Ala Pro Leu Gln Glu Leu Ile
                 245                 250                 255
Arg Val Pro Glu Arg Leu Leu Phe Ile Ile Asp Gly Phe Asp Glu Leu
             260                 265                 270
Lys Pro Ser Phe His Asp Pro Gln Gly Pro Trp Cys Leu Cys Trp Glu
         275                 280                 285
Glu Lys Arg Pro Thr Glu Leu Leu Asn Ser Leu Ile Arg Lys Lys
         290                 295                 300
Leu Leu Pro Glu Leu Ser Leu Leu Ile Thr Thr Arg Pro Thr Ala Leu
305                 310                 315                 320
Glu Lys Leu His Arg Leu Leu Glu His Pro Arg His Val Glu Ile Leu
                 325                 330                 335
Gly Phe Ser Glu Ala Glu Arg Lys Glu Tyr Phe Tyr Lys Tyr Phe His
             340                 345                 350
Asn Ala Glu Gln Ala Gly Gln Val Phe Asn Tyr Val Arg Asp Asn Glu
             355                 360                 365
Pro Leu Phe Thr Met Cys Phe Val Pro Leu Val Cys Trp Val Val Cys
         370                 375                 380
Thr Cys Leu Gln Gln Gln Leu Glu Gly Gly Leu Leu Arg Gln Thr
385                 390                 395                 400
Ser Arg Thr Thr Thr Ala Val Tyr Met Leu Tyr Leu Leu Ser Leu Met
                 405                 410                 415
Gln Pro Lys Pro Gly Ala Pro Arg Leu Gln Pro Pro Asn Gln Arg
             420                 425                 430
Gly Leu Cys Ser Leu Ala Ala Asp Gly Leu Trp Asn Gln Lys Ile Leu
         435                 440                 445
```

-continued

```
Phe Glu Glu Gln Asp Leu Arg Lys His Gly Leu Asp Gly Glu Asp Val
    450                 455                 460

Ser Ala Phe Leu Asn Met Asn Ile Phe Gln Lys Asp Ile Asn Cys Glu
465                 470                 475                 480

Arg Tyr Tyr Ser Phe Ile His Leu Ser Phe Gln Glu Phe Phe Ala Ala
                485                 490                 495

Met Tyr Tyr Ile Leu Asp Glu Gly Gly Ala Gly Pro Asp Gln
                500                 505                 510

Asp Val Thr Arg Leu Leu Thr Glu Tyr Ala Phe Ser Glu Arg Ser Phe
            515                 520                 525

Leu Ala Leu Thr Ser Arg Phe Leu Phe Gly Leu Leu Asn Glu Glu Thr
        530                 535                 540

Arg Ser His Leu Glu Lys Ser Leu Cys Trp Lys Val Ser Pro His Ile
545                 550                 555                 560

Lys Met Asp Leu Leu Gln Trp Ile Gln Ser Lys Ala Gln Ser Asp Gly
                565                 570                 575

Ser Thr Leu Gln Gln Gly Ser Leu Glu Phe Phe Ser Cys Leu Tyr Glu
                580                 585                 590

Ile Gln Glu Glu Phe Ile Gln Gln Ala Leu Ser His Phe Gln Val
            595                 600                 605

Ile Val Val Ser Asn Ile Ala Ser Lys Met Glu His Met Val Ser Ser
        610                 615                 620

Phe Cys Leu Lys Arg Cys Arg Ser Ala Gln Val Leu His Leu Tyr Gly
625                 630                 635                 640

Ala Thr Tyr Ser Ala Asp Gly Glu Asp Arg Ala Arg Cys Ser Ala Gly
                645                 650                 655

Ala His Thr Leu Leu Val Gln Leu Arg Pro Glu Arg Thr Val Leu Leu
                660                 665                 670

Asp Ala Tyr Ser Glu His Leu Ala Ala Leu Cys Thr Asn Pro Asn
            675                 680                 685

Leu Ile Glu Leu Ser Leu Tyr Arg Asn Ala Leu Gly Ser Arg Gly Val
        690                 695                 700

Lys Leu Leu Cys Gln Gly Leu Arg His Pro Asn Cys Lys Leu Gln Asn
705                 710                 715                 720

Leu Arg Leu Lys Arg Cys Arg Ile Ser Ser Ser Ala Cys Glu Asp Leu
                725                 730                 735

Ser Ala Ala Leu Ile Ala Asn Lys Asn Leu Thr Arg Met Asp Leu Ser
                740                 745                 750

Gly Asn Gly Val Gly Phe Pro Gly Met Met Leu Leu Cys Glu Gly Leu
            755                 760                 765

Arg His Pro Gln Cys Arg Leu Gln Met Ile Gln Leu Arg Lys Cys Gln
        770                 775                 780

Leu Glu Ser Gly Ala Cys Gln Glu Met Ala Ser Val Leu Gly Thr Asn
785                 790                 795                 800

Pro His Leu Val Glu Leu Asp Leu Thr Gly Asn Ala Leu Glu Asp Leu
                805                 810                 815

Gly Leu Arg Leu Leu Cys Gln Gly Leu Arg His Pro Val Cys Arg Leu
            820                 825                 830

Arg Thr Leu Trp Leu Lys Ile Cys Arg Leu Thr Ala Ala Cys Asp
        835                 840                 845

Glu Leu Ala Ser Thr Leu Ser Val Asn Gln Ser Leu Arg Glu Leu Asp
850                 855                 860
```

```
Leu Ser Leu Asn Glu Leu Gly Asp Leu Gly Val Leu Leu Cys Glu
865                 870                 875                 880

Gly Leu Arg His Pro Thr Cys Lys Leu Gln Thr Leu Arg Leu Gly Ile
                885                 890                 895

Cys Arg Leu Gly Ser Ala Ala Cys Glu Gly Leu Ser Val Val Leu Gln
            900                 905                 910

Ala Asn His Asn Leu Arg Glu Leu Asp Leu Ser Phe Asn Asp Leu Gly
        915                 920                 925

Asp Trp Gly Leu Trp Leu Leu Ala Glu Gly Leu Gln His Pro Ala Cys
    930                 935                 940

Arg Leu Gln Lys Leu Trp Leu Asp Ser Cys Gly Leu Thr Ala Lys Ala
945                 950                 955                 960

Cys Glu Asn Leu Tyr Phe Thr Leu Gly Ile Asn Gln Thr Leu Thr Asp
                965                 970                 975

Leu Tyr Leu Thr Asn Asn Ala Leu Gly Asp Thr Gly Val Arg Leu Leu
            980                 985                 990

Cys Lys Arg Leu Ser His Pro Gly Cys Lys Leu Arg Val Leu Trp Leu
        995                 1000                1005

Phe Gly Met Asp Leu Asn Lys Met Thr His Ser Arg Leu Ala Ala Leu
    1010                1015                1020

Arg Val Thr Lys Pro Tyr Leu Asp Ile Gly Cys
1025                1030                1035

<210> SEQ ID NO 25
<211> LENGTH: 243
<212> TYPE: DNA
<213> ORGANISM: Homo sapien
<220> FEATURE:
<221> NAME/KEY: CDS
<222> LOCATION: (1)...(243)

<400> SEQUENCE: 25 atg gca agc acc cgc tgc aag ctg gcc agg tac ctg gag gac ctg gag     48
Met Ala Ser Thr Arg Cys Lys Leu Ala Arg Tyr Leu Glu Asp Leu Glu
1               5                   10                  15 gat gtg gac ttg aag aaa ttt aag atg cac tta gag gac tat cct ccc     96
Asp Val Asp Leu Lys Lys Phe Lys Met His Leu Glu Asp Tyr Pro Pro
            20                  25                  30 cag aag ggc tgc atc ccc ctc ccg agg ggt cag aca gag aag gca gac    144
Gln Lys Gly Cys Ile Pro Leu Pro Arg Gly Gln Thr Glu Lys Ala Asp
        35                  40                  45 cat gtg gat cta gcc acg cta atg atc gac ttc aat ggg gag gag aag    192
His Val Asp Leu Ala Thr Leu Met Ile Asp Phe Asn Gly Glu Glu Lys
    50                  55                  60 gcg tgg gcc atg gtc gtg tgg atc ttc gct gcg atc aac agg aga gac    240
Ala Trp Ala Met Val Val Trp Ile Phe Ala Ala Ile Asn Arg Arg Asp
65                  70                  75                  80 ctt                                                                243
Leu

<210> SEQ ID NO 26
<211> LENGTH: 81
<212> TYPE: PRT
<213> ORGANISM: Homo sapien

<400> SEQUENCE: 26

Met Ala Ser Thr Arg Cys Lys Leu Ala Arg Tyr Leu Glu Asp Leu Glu
1               5                   10                  15
```

```
Asp Val Asp Leu Lys Lys Phe Lys Met His Leu Glu Asp Tyr Pro Pro
         20                  25                  30

Gln Lys Gly Cys Ile Pro Leu Pro Arg Gly Gln Thr Glu Lys Ala Asp
             35                  40                  45

His Val Asp Leu Ala Thr Leu Met Ile Asp Phe Asn Gly Glu Glu Lys
 50                      55                  60

Ala Trp Ala Met Val Val Trp Ile Phe Ala Ala Ile Asn Arg Arg Asp
 65                  70                  75                  80

Leu
```

<210> SEQ ID NO 27
<211> LENGTH: 270
<212> TYPE: DNA
<213> ORGANISM: Homo sapien
<220> FEATURE:
<221> NAME/KEY: CDS
<222> LOCATION: (1)...(267)

<400> SEQUENCE: 27

```
atg gga acg aag cgc gag gcc atc ctg aag gtg ctg gag aac ctg aca      48
Met Gly Thr Lys Arg Glu Ala Ile Leu Lys Val Leu Glu Asn Leu Thr
 1               5                  10                  15 ccg gag gag ctc aag aag ttc aag atg aag ctg ggg acg gtg ccg ctg      96
Pro Glu Glu Leu Lys Lys Phe Lys Met Lys Leu Gly Thr Val Pro Leu
                 20                  25                  30 cgc gag ggc ttt gag cgc atc ccg cgg ggc gcg ctc ggg cag cta gat     144
Arg Glu Gly Phe Glu Arg Ile Pro Arg Gly Ala Leu Gly Gln Leu Asp
             35                  40                  45 atc gtg gac ctc acc gac aag ctg gtc gcc tcc tac tac gag gac tac     192
Ile Val Asp Leu Thr Asp Lys Leu Val Ala Ser Tyr Tyr Glu Asp Tyr
 50                      55                  60 gca gcc gag ctc gtc gtg gcc gtg ctg cgc gac atg cgc atg ttg gag     240
Ala Ala Glu Leu Val Val Ala Val Leu Arg Asp Met Arg Met Leu Glu
 65                  70                  75                  80 gag gcc gca cgg ctg cag cgg gct gcg tga                             270
Glu Ala Ala Arg Leu Gln Arg Ala Ala
                 85
```

<210> SEQ ID NO 28
<211> LENGTH: 89
<212> TYPE: PRT
<213> ORGANISM: Homo sapien

<400> SEQUENCE: 28

```
Met Gly Thr Lys Arg Glu Ala Ile Leu Lys Val Leu Glu Asn Leu Thr
 1               5                  10                  15

Pro Glu Glu Leu Lys Lys Phe Lys Met Lys Leu Gly Thr Val Pro Leu
                 20                  25                  30

Arg Glu Gly Phe Glu Arg Ile Pro Arg Gly Ala Leu Gly Gln Leu Asp
             35                  40                  45

Ile Val Asp Leu Thr Asp Lys Leu Val Ala Ser Tyr Tyr Glu Asp Tyr
 50                      55                  60

Ala Ala Glu Leu Val Val Ala Val Leu Arg Asp Met Arg Met Leu Glu
 65                  70                  75                  80

Glu Ala Ala Arg Leu Gln Arg Ala Ala
                 85
```

```
<210> SEQ ID NO 29
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid
<220> FEATURE:
<221> NAME/KEY: VARIANT
<222> LOCATION: 4, 5
<223> OTHER INFORMATION: Xaa = Any Amino Acid

<400> SEQUENCE: 29

Lys Phe Lys Xaa Xaa Leu
 1               5

<210> SEQ ID NO 30
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid
<220> FEATURE:
<221> NAME/KEY: VARIANT
<222> LOCATION: 4, 5
<223> OTHER INFORMATION: Xaa = Any Amino Acid

<400> SEQUENCE: 30

Lys Leu Lys Xaa Xaa Leu
 1               5

<210> SEQ ID NO 31
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid
<220> FEATURE:
<221> NAME/KEY: VARIANT
<222> LOCATION: 4, 5
<223> OTHER INFORMATION: Xaa = Any Amino Acid

<400> SEQUENCE: 31

Arg Phe Arg Xaa Xaa Leu
 1               5

<210> SEQ ID NO 32
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid
<220> FEATURE:
<221> NAME/KEY: VARIANT
<222> LOCATION: 4, 5
<223> OTHER INFORMATION: Xaa = Any Amino Acid

<400> SEQUENCE: 32

Arg Phe Lys Xaa Xaa Leu
 1               5
```

```
<210> SEQ ID NO 33
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid
<220> FEATURE:
<221> NAME/KEY: VARIANT
<222> LOCATION: 4, 5
<223> OTHER INFORMATION: Xaa = Any Amino Acid

<400> SEQUENCE: 33

Lys Phe Arg Xaa Xaa Leu
 1               5

<210> SEQ ID NO 34
<211> LENGTH: 6
<212> TYPE: PRT
<213> ORGANISM: Homo sapien
<220> FEATURE:
<221> NAME/KEY: VARIANT
<222> LOCATION: (4)...(5)
<223> OTHER INFORMATION: Xaa=any amino acid
<220> FEATURE:
<221> NAME/KEY: VARIANT
<222> LOCATION: 4, 5
<223> OTHER INFORMATION: Xaa = Any Amino Acid

<400> SEQUENCE: 34

Lys Phe Lys Xaa Xaa Ile
 1               5

<210> SEQ ID NO 35
<211> LENGTH: 39
<212> TYPE: DNA
<213> ORGANISM: Artificial Sequence
<220> FEATURE:
<223> OTHER INFORMATION: synthetic primer

<400> SEQUENCE: 35
ccggaattca ccatggcagc ctctttcttc tctgatttt                    39

<210> SEQ ID NO 36
<211> LENGTH: 41
<212> TYPE: DNA
<213> ORGANISM: Artificial Sequence
<220> FEATURE:
<223> OTHER INFORMATION: synthetic primer

<400> SEQUENCE: 36
ccgctcgagt cacgtagagc tgtgttcatc ctctttctta a                 41

<210> SEQ ID NO 37
<211> LENGTH: 319
<212> TYPE: PRT
<213> ORGANISM: Homo sapiens

<400> SEQUENCE: 37

Gln Pro Arg Thr Val Ile Ile Gln Gly Pro Gln Gly Ile Gly Lys Thr
 1               5                  10                  15

Thr Leu Leu Met Lys Leu Met Met Ala Trp Ser Asp Asn Lys Ile Phe
             20                  25                  30

Arg Asp Arg Phe Leu Tyr Thr Phe Tyr Phe Cys Cys Arg Glu Leu Arg
         35                  40                  45
```

```
Glu Leu Pro Pro Thr Ser Leu Ala Asp Leu Ile Ser Arg Glu Trp Pro
    50                  55                  60

Asp Pro Ala Ala Pro Ile Thr Glu Ile Val Ser Gln Pro Glu Arg Leu
65                  70                  75                  80

Leu Phe Val Ile Asp Ser Phe Glu Glu Leu Gln Gly Gly Leu Asn Glu
                85                  90                  95

Pro Asp Ser Asp Leu Cys Gly Asp Leu Met Glu Lys Arg Pro Val Gln
            100                 105                 110

Val Leu Leu Ser Ser Leu Leu Arg Lys Lys Met Leu Pro Glu Ala Ser
        115                 120                 125

Leu Leu Ile Ala Ile Lys Pro Val Cys Pro Lys Glu Leu Arg Asp Gln
    130                 135                 140

Val Thr Ile Ser Glu Ile Tyr Gln Pro Arg Gly Phe Asn Glu Ser Asp
145                 150                 155                 160

Arg Leu Val Tyr Phe Cys Cys Phe Phe Lys Asp Pro Lys Arg Ala Met
                165                 170                 175

Glu Ala Phe Asn Leu Val Arg Glu Ser Glu Gln Leu Phe Ser Ile Cys
            180                 185                 190

Gln Ile Pro Leu Leu Cys Trp Ile Leu Cys Thr Ser Leu Lys Gln Glu
        195                 200                 205

Met Gln Lys Gly Lys Asp Leu Ala Leu Thr Cys Gln Ser Thr Thr Ser
    210                 215                 220

Val Tyr Ser Ser Phe Val Phe Asn Leu Phe Thr Pro Glu Gly Ala Glu
225                 230                 235                 240

Gly Pro Thr Pro Gln Thr Gln His Gln Leu Lys Ala Leu Cys Ser Leu
                245                 250                 255

Ala Ala Glu Gly Met Trp Thr Asp Thr Phe Glu Phe Cys Glu Asp Asp
            260                 265                 270

Leu Arg Arg Asn Gly Val Val Asp Ala Asp Ile Pro Ala Leu Leu Gly
        275                 280                 285

Thr Lys Ile Leu Leu Lys Tyr Gly Glu Arg Glu Ser Ser Tyr Val Phe
    290                 295                 300

Leu His Val Cys Ile Gln Glu Phe Cys Ala Ala Leu Phe Tyr Leu
305                 310                 315

<210> SEQ ID NO 38
<211> LENGTH: 270
<212> TYPE: PRT
<213> ORGANISM: Homo sapiens

<400> SEQUENCE: 38

Ser Ile Cys Gln Ile Pro Leu Leu Cys Trp Ile Leu Cys Thr Ser Leu
1               5                   10                  15

Lys Gln Glu Met Gln Lys Gly Lys Asp Leu Ala Leu Thr Cys Gln Ser
            20                  25                  30

Thr Thr Ser Val Tyr Ser Ser Phe Val Phe Asn Leu Phe Thr Pro Glu
        35                  40                  45

Gly Ala Glu Gly Pro Thr Pro Gln Thr Gln His Gln Leu Lys Ala Leu
    50                  55                  60

Cys Ser Leu Ala Ala Glu Gly Met Trp Thr Asp Thr Phe Glu Phe Cys
65                  70                  75                  80

Glu Asp Asp Leu Arg Arg Asn Gly Val Val Asp Ala Asp Ile Pro Ala
                85                  90                  95

Leu Leu Gly Thr Lys Ile Leu Leu Lys Tyr Gly Glu Arg Glu Ser Ser
            100                 105                 110
```

```
Tyr Val Phe Leu His Val Cys Ile Gln Glu Phe Cys Ala Ala Leu Phe
            115                 120                 125

Tyr Leu Leu Lys Ser His Leu Asp His Pro His Pro Ala Val Arg Cys
        130                 135                 140

Val Gln Glu Leu Val Ala Asn Phe Glu Lys Ala Arg Arg Ala His
145                 150                 155                 160

Trp Ile Phe Leu Gly Cys Phe Leu Thr Gly Leu Leu Asn Lys Lys Glu
                165                 170                 175

Gln Glu Lys Leu Asp Ala Phe Gly Phe Gln Leu Ser Gln Glu Ile
            180                 185                 190

Lys Gln Gln Ile His Gln Cys Leu Lys Ser Leu Gly Glu Arg Gly Asn
        195                 200                 205

Pro Gln Gly Gln Val Asp Ser Leu Ala Ile Phe Tyr Cys Leu Phe Glu
    210                 215                 220

Met Gln Asp Pro Ala Phe Val Lys Gln Ala Val Asn Leu Leu Gln Glu
225                 230                 235                 240

Ala Asn Phe His Ile Ile Asp Asn Val Asp Leu Val Val Ser Ala Tyr
                245                 250                 255

Cys Leu Lys Tyr Cys Ser Ser Leu Arg Lys Leu Cys Phe Ser
            260                 265                 270

<210> SEQ ID NO 39
<211> LENGTH: 375
<212> TYPE: PRT
<213> ORGANISM: Homo sapiens

<400> SEQUENCE: 39

Ser Asp Tyr Ser Leu Ile Cys Trp His His Ile Cys Ser Val Leu Thr
1               5                   10                  15

Thr Ser Gly His Leu Arg Glu Leu Gln Val Gln Asp Ser Thr Leu Ser
            20                  25                  30

Glu Ser Thr Phe Val Thr Trp Cys Asn Gln Leu Arg His Pro Ser Cys
        35                  40                  45

Arg Leu Gln Lys Leu Gly Ile Asn Asn Val Ser Phe Ser Gly Gln Ser
    50                  55                  60

Val Leu Leu Phe Glu Val Leu Phe Tyr Gln Pro Asp Leu Lys Tyr Leu
65                  70                  75                  80

Ser Phe Thr Leu Thr Lys Leu Ser Arg Asp Asp Ile Arg Ser Leu Cys
                85                  90                  95

Asp Ala Leu Asn Tyr Pro Ala Gly Asn Val Lys Glu Leu Ala Leu Val
            100                 105                 110

Asn Cys His Leu Ser Pro Ile Asp Cys Glu Val Leu Ala Gly Leu Leu
        115                 120                 125

Thr Asn Asn Lys Lys Leu Thr Tyr Leu Asn Val Ser Cys Asn Gln Leu
    130                 135                 140

Asp Thr Gly Val Pro Leu Leu Cys Glu Ala Leu Cys Ser Pro Asp Thr
145                 150                 155                 160

Val Leu Val Tyr Leu Met Leu Ala Phe Cys His Leu Ser Glu Gln Cys
                165                 170                 175

Cys Glu Tyr Ile Ser Glu Met Leu Leu Arg Asn Lys Ser Val Arg Tyr
            180                 185                 190

Leu Asp Leu Ser Ala Asn Val Leu Lys Asp Glu Gly Leu Lys Thr Leu
        195                 200                 205

Cys Glu Ala Leu Lys His Pro Asp Cys Cys Leu Asp Ser Leu Cys Leu
    210                 215                 220
```

```
Val Lys Cys Phe Ile Thr Ala Ala Gly Cys Glu Asp Leu Ala Ser Ala
225                 230                 235                 240

Leu Ile Ser Asn Gln Asn Leu Lys Ile Leu Gln Ile Gly Cys Asn Glu
            245                 250                 255

Ile Gly Asp Val Gly Val Gln Leu Leu Cys Arg Ala Leu Thr His Thr
        260                 265                 270

Asp Cys Arg Leu Glu Ile Leu Gly Leu Glu Glu Cys Gly Leu Thr Ser
        275                 280                 285

Thr Cys Cys Lys Asp Leu Ala Ser Val Leu Thr Cys Ser Lys Thr Leu
        290                 295                 300

Gln Gln Leu Asn Leu Thr Leu Asn Thr Leu Asp His Thr Gly Val Val
305                 310                 315                 320

Val Leu Cys Glu Ala Leu Arg His Pro Glu Cys Ala Leu Gln Val Leu
                325                 330                 335

Gly Leu Arg Lys Thr Asp Phe Asp Glu Thr Gln Ala Leu Leu Thr
                340                 345                 350

Ala Glu Glu Glu Arg Asn Pro Asn Leu Thr Ile Thr Asp Asp Cys Asp
            355                 360                 365

Thr Ile Thr Arg Val Glu Ile
        370                 375

<210> SEQ ID NO 40
<211> LENGTH: 38
<212> TYPE: DNA
<213> ORGANISM: Artificial Sequence
<220> FEATURE:
<223> OTHER INFORMATION: synthetic primer

<400> SEQUENCE: 40
cctctcgagt cagatctcta cccttgtgat tgtgtcac                              38

<210> SEQ ID NO 41
<211> LENGTH: 24
<212> TYPE: DNA
<213> ORGANISM: Artificial Sequence
<220> FEATURE:
<223> OTHER INFORMATION: synthetic primer

<400> SEQUENCE: 41
gaattcgatc ctggagccat gggg                                             24

<210> SEQ ID NO 42
<211> LENGTH: 24
<212> TYPE: DNA
<213> ORGANISM: Artificial Sequence
<220> FEATURE:
<223> OTHER INFORMATION: synthetic primer

<400> SEQUENCE: 42
ctcgagccgg agtgttgctg ggaa                                             24

<210> SEQ ID NO 43
<211> LENGTH: 24
<212> TYPE: DNA
<213> ORGANISM: Artificial Sequence
<220> FEATURE:
<223> OTHER INFORMATION: synthetic primer

<400> SEQUENCE: 43
gaattcgatc ctggagccat gggg                                             24
```

```
<210> SEQ ID NO 44
<211> LENGTH: 24
<212> TYPE: DNA
<213> ORGANISM: Artificial Sequence
<220> FEATURE:
<223> OTHER INFORMATION: synthetic primer

<400> SEQUENCE: 44
ctcgagtcag cttggctgcc gact                                        24

<210> SEQ ID NO 45
<211> LENGTH: 31
<212> TYPE: DNA
<213> ORGANISM: Artificial Sequence
<220> FEATURE:
<223> OTHER INFORMATION: synthetic primer

<400> SEQUENCE: 45 cccctcgag ggcctggctt ggctgccgac t                                 31

<210> SEQ ID NO 46
<211> LENGTH: 24
<212> TYPE: DNA
<213> ORGANISM: Artificial Sequence
<220> FEATURE:
<223> OTHER INFORMATION: synthetic primer

<400> SEQUENCE: 46
gaattccctc agtcggcagc caag                                        24

<210> SEQ ID NO 47
<211> LENGTH: 24
<212> TYPE: DNA
<213> ORGANISM: Artificial Sequence
<220> FEATURE:
<223> OTHER INFORMATION: synthetic primer

<400> SEQUENCE: 47
ctcgagccgg agtgttgctg ggaa                                        24

<210> SEQ ID NO 48
<211> LENGTH: 22
<212> TYPE: DNA
<213> ORGANISM: Artificial Sequence
<220> FEATURE:
<223> OTHER INFORMATION: synthetic primer

<400> SEQUENCE: 48
gaattcgagg cgcagggctg tg                                          22

<210> SEQ ID NO 49
<211> LENGTH: 24
<212> TYPE: DNA
<213> ORGANISM: Artificial Sequence
<220> FEATURE:
<223> OTHER INFORMATION: synthetic primer

<400> SEQUENCE: 49
ctcgaggctt cacaggcgtt gcat                                        24

<210> SEQ ID NO 50
<211> LENGTH: 24
<212> TYPE: DNA
<213> ORGANISM: Artificial Sequence
<220> FEATURE:
<223> OTHER INFORMATION: synthetic primer
```

<400> SEQUENCE: 50
ctcgaggcta cacaggcgtt gcat                                    24

<210> SEQ ID NO 51
<211> LENGTH: 30
<212> TYPE: DNA
<213> ORGANISM: Artificial Sequence
<220> FEATURE:
<223> OTHER INFORMATION: synthetic primer

<400> SEQUENCE: 51
gaattcctct gggccttgag tgaccttgag                              30

<210> SEQ ID NO 52
<211> LENGTH: 29
<212> TYPE: DNA
<213> ORGANISM: Artificial Sequence
<220> FEATURE:
<223> OTHER INFORMATION: synthetic primer

<400> SEQUENCE: 52
ccagccgacc tcgagcagtc aaatatggc                               29

<210> SEQ ID NO 53
<211> LENGTH: 21
<212> TYPE: DNA
<213> ORGANISM: Artificial Sequence
<220> FEATURE:
<223> OTHER INFORMATION: synthetic primer

<400> SEQUENCE: 53
ttgctcgagt catctgaata c                                       21

<210> SEQ ID NO 54
<211> LENGTH: 25
<212> TYPE: DNA
<213> ORGANISM: Artificial Sequence
<220> FEATURE:
<223> OTHER INFORMATION: synthetic primer

<400> SEQUENCE: 54
atggccatgg ccaaggccag aaagc                                   25

<210> SEQ ID NO 55
<211> LENGTH: 21
<212> TYPE: DNA
<213> ORGANISM: Artificial Sequence
<220> FEATURE:
<223> OTHER INFORMATION: synthetic primer

<400> SEQUENCE: 55
ttgctcgagt catctgaata c                                       21

<210> SEQ ID NO 56
<211> LENGTH: 31
<212> TYPE: DNA
<213> ORGANISM: Artificial Sequence
<220> FEATURE:
<223> OTHER INFORMATION: synthetic primer

<400> SEQUENCE: 56
gacggatcct gtggcatggc cacctacttg g                            31

-continued

<210> SEQ ID NO 57
<211> LENGTH: 29
<212> TYPE: DNA
<213> ORGANISM: Artificial Sequence
<220> FEATURE:
<223> OTHER INFORMATION: synthetic primer

<400> SEQUENCE: 57
atccctcacg aattcccctc actgtcctc                                    29

<210> SEQ ID NO 58
<211> LENGTH: 2524
<212> TYPE: DNA
<213> ORGANISM: Homo sapiens
<220> FEATURE:
<221> NAME/KEY: CDS
<222> LOCATION: (176)...(2332)
<220> FEATURE:
<221> NAME/KEY: misc_feature
<222> LOCATION: (306)...(458)
<223> OTHER INFORMATION: n = A,T,C or G

<400> SEQUENCE: 58
ttaaagattt tgacttgtta cagtcatgtg acattttttt ctttctgttt gctgagtttt    60
tgataattta tatctctcaa agtggagact ttaaaaaaga ctcatccgtg tgccgtgttc   120
actgcctggt atcttagtgt ggaccgaagc ctaaggaccc tgaaaacagc tgcag atg   178
                                                              Met
                                                               1 aag atg gca agc acc cgc tgc aag ctg gcc agg tac ctg gag gac ctg   226
Lys Met Ala Ser Thr Arg Cys Lys Leu Ala Arg Tyr Leu Glu Asp Leu
        5                  10                  15 gag gat gtg gac ttg aag aaa ttt aag atg cac tta gag gac tat cct   274
Glu Asp Val Asp Leu Lys Lys Phe Lys Met His Leu Glu Asp Tyr Pro
 20                  25                  30 ccc cag aag ggc tgc atc ccc ctc ccg agg gnn nnn nnn nnn nnn nnn   322
Pro Gln Lys Gly Cys Ile Pro Leu Pro Arg Xaa Xaa Xaa Xaa Xaa Xaa
 35                  40                  45 nnn nnn nnn nnn nnn nnn nnn nnn nnn nnn nnn nnn nnn nnn nnn nnn   370
Xaa Xaa Xaa Xaa Xaa Xaa Xaa Xaa Xaa Xaa Xaa Xaa Xaa Xaa Xaa Xaa
 50                  55                  60                  65 nnn nnn nnn nnn nnn nnn nnn nnn nnn nnn nnn nnn nnn nnn nnn nnn   418
Xaa Xaa Xaa Xaa Xaa Xaa Xaa Xaa Xaa Xaa Xaa Xaa Xaa Xaa Xaa Xaa
                 70                  75                  80 nnn nnn nnn nnn nnn nnn nnn nnn nnn nnn nnn ngt tca gat             466
Xaa Xaa Xaa Xaa Xaa Xaa Xaa Xaa Xaa Xaa Xaa Ser Asp
             85                  90                  95 aat gca cgt gtt tcg aat ccc act gtg ata tgc cag gaa gac agc att   514
Asn Ala Arg Val Ser Asn Pro Thr Val Ile Cys Gln Glu Asp Ser Ile
            100                 105                 110 gaa gag gag tgg atg ggt tta ctg gag tac ctt tcg aga atc tct att   562
Glu Glu Glu Trp Met Gly Leu Leu Glu Tyr Leu Ser Arg Ile Ser Ile
        115                 120                 125 tgt aaa atg aag aaa gat tac cgt aag aag tac aga aag tac gtg aga   610
Cys Lys Met Lys Lys Asp Tyr Arg Lys Lys Tyr Arg Lys Tyr Val Arg
130                 135                 140                 145 agc aga ttc cag tgc att gaa gac agg aat gcc cgt ctg ggt gag agt   658
Ser Arg Phe Gln Cys Ile Glu Asp Arg Asn Ala Arg Leu Gly Glu Ser
                150                 155                 160 gtg agc ctc aac aaa cgc tac aca cga ctg cgt ctc atc aag gag cac   706
Val Ser Leu Asn Lys Arg Tyr Thr Arg Leu Arg Leu Ile Lys Glu His
            165                 170                 175

-continued

| | |
|---|---|
| cgg agc cag cag gag agg gag cag gag ctt ctg gcc atc ggc aag acc<br>Arg Ser Gln Gln Glu Arg Glu Gln Glu Leu Leu Ala Ile Gly Lys Thr<br>        180                          185                            190 | 754 |
| aag acg tgt gag agc ccc gtg agt ccc att aag atg gag ttg ctg ttt<br>Lys Thr Cys Glu Ser Pro Val Ser Pro Ile Lys Met Glu Leu Leu Phe<br>195                          200                          205 | 802 |
| gac ccc gat gat gag cat tct gag cct gtg cac acc gtg gtg ttc cag<br>Asp Pro Asp Asp Glu His Ser Glu Pro Val His Thr Val Val Phe Gln<br>210                          215                          220              225 | 850 |
| ggg gcg gca ggg att ggg aaa aca atc ctg gcc agg aag atg atg ttg<br>Gly Ala Ala Gly Ile Gly Lys Thr Ile Leu Ala Arg Lys Met Met Leu<br>                          230                          235                        240 | 898 |
| gac tgg gcg tcg ggg aca ctc tac caa gac agg ttt gac tat ctg ttc<br>Asp Trp Ala Ser Gly Thr Leu Tyr Gln Asp Arg Phe Asp Tyr Leu Phe<br>                    245                          250                        255 | 946 |
| tat atc cac tgt cga gag gtg agc ctt gtg aca cag agg agc ctg ggg<br>Tyr Ile His Cys Arg Glu Val Ser Leu Val Thr Gln Arg Ser Leu Gly<br>                    260                          265                        270 | 994 |
| gac ctg atc atg agc tgc tgc ccc gac cca aac cca ccc atc cac aag<br>Asp Leu Ile Met Ser Cys Cys Pro Asp Pro Asn Pro Pro Ile His Lys<br>275                          280                          285 | 1042 |
| atc gtg aga aaa ccc tcc aga atc ctc ttc ctc atg gac ggc ttc gat<br>Ile Val Arg Lys Pro Ser Arg Ile Leu Phe Leu Met Asp Gly Phe Asp<br>290                          295                          300              305 | 1090 |
| gag ctg caa ggt gcc ttt gac gag cac ata gga ccg ctc tgc act gac<br>Glu Leu Gln Gly Ala Phe Asp Glu His Ile Gly Pro Leu Cys Thr Asp<br>                        310                          315                        320 | 1138 |
| tgg cag aag gcc gag cgg gga gac att ctc ctg agc agc ctc atc aga<br>Trp Gln Lys Ala Glu Arg Gly Asp Ile Leu Leu Ser Ser Leu Ile Arg<br>                  325                          330                        335 | 1186 |
| aag aag ctg ctt ccc gag gcc tct ctg ctc atc acc acg aga cct gtg<br>Lys Lys Leu Leu Pro Glu Ala Ser Leu Leu Ile Thr Thr Arg Pro Val<br>340                          345                          350 | 1234 |
| gcc ctg gag aaa ctg cag cac ttg ctg gac cat cct cgg cat gtg gag<br>Ala Leu Glu Lys Leu Gln His Leu Leu Asp His Pro Arg His Val Glu<br>355                          360                          365 | 1282 |
| atc ctg ggt ttc tcc gag gcc aaa agg aaa gag tac ttc ttc aag tac<br>Ile Leu Gly Phe Ser Glu Ala Lys Arg Lys Glu Tyr Phe Phe Lys Tyr<br>370                          375                          380              385 | 1330 |
| ttc tct gat gag gcc caa gcc agg gca gcc ttc agt ctg att cag gag<br>Phe Ser Asp Glu Ala Gln Ala Arg Ala Ala Phe Ser Leu Ile Gln Glu<br>                        390                          395                        400 | 1378 |
| aac gag gtc ctc ttc acc atg tgc ttc atc ccc ctg gtc tgc tgg atc<br>Asn Glu Val Leu Phe Thr Met Cys Phe Ile Pro Leu Val Cys Trp Ile<br>                  405                          410                        415 | 1426 |
| gtg tgc act gga ctg aaa cag cag atg gag agt ggc aag agc ctt gcc<br>Val Cys Thr Gly Leu Lys Gln Gln Met Glu Ser Gly Lys Ser Leu Ala<br>                        420                          425                        430 | 1474 |
| cag aca tcc aag acc acc acc gcg gtg tac gtc ttc ttc ctt tcc agt<br>Gln Thr Ser Lys Thr Thr Thr Ala Val Tyr Val Phe Phe Leu Ser Ser<br>435                          440                          445 | 1522 |
| ttg ctg cag ccc cgg gga ggg agc cag gag cac ggc ctc tgc gcc cac<br>Leu Leu Gln Pro Arg Gly Gly Ser Gln Glu His Gly Leu Cys Ala His<br>450                          455                          460              465 | 1570 |
| ctc tgg ggg ctc tgc tct ttg gct gca gat gga atc tgg aac cag aaa<br>Leu Trp Gly Leu Cys Ser Leu Ala Ala Asp Gly Ile Trp Asn Gln Lys<br>                        470                          475                        480 | 1618 |
| atc ctg ttt gag gag tcc gac ctc agg aat cat gga ctg cag aag gcg<br>Ile Leu Phe Glu Glu Ser Asp Leu Arg Asn His Gly Leu Gln Lys Ala<br>                  485                          490                        495 | 1666 |

```
gat gtg tct gct ttc ctg agg atg aac ctg ttc caa aag gaa gtg gac      1714
Asp Val Ser Ala Phe Leu Arg Met Asn Leu Phe Gln Lys Glu Val Asp
    500                 505                 510 tgc gag aag ttc tac agc ttc atc cac atg act ttc cag gag ttc ttt      1762
Cys Glu Lys Phe Tyr Ser Phe Ile His Met Thr Phe Gln Glu Phe Phe
515                 520                 525 gcc gcc atg tac tac ctg ctg gaa gag gaa aag gaa gga agg acg aac      1810
Ala Ala Met Tyr Tyr Leu Leu Glu Glu Glu Lys Glu Gly Arg Thr Asn
530                 535                 540                 545 gtt cca ggg agt cgt ttg aag ctt ccc agc cga gac gtg aca gtc ctt      1858
Val Pro Gly Ser Arg Leu Lys Leu Pro Ser Arg Asp Val Thr Val Leu
                550                 555                 560 ctg gaa aac tat ggc aaa ttc gaa aag ggg tat ttg att ttt gtt gta      1906
Leu Glu Asn Tyr Gly Lys Phe Glu Lys Gly Tyr Leu Ile Phe Val Val
                565                 570                 575 cgt ttc ctc ttt ggc ctg gta aac cag gag agg acc tcc tac ttg gag      1954
Arg Phe Leu Phe Gly Leu Val Asn Gln Glu Arg Thr Ser Tyr Leu Glu
                580                 585                 590 aag aaa tta agt tgc aag atc tct cag caa atc agg ctg gag ctg ctg      2002
Lys Lys Leu Ser Cys Lys Ile Ser Gln Gln Ile Arg Leu Glu Leu Leu
595                 600                 605 aaa tgg att gaa gtg aaa gcc aaa gct aaa aag ctg cag atc cag ccc      2050
Lys Trp Ile Glu Val Lys Ala Lys Ala Lys Lys Leu Gln Ile Gln Pro
610                 615                 620                 625 agc cag ctg gaa ttg ttc tac tgt ttg tac gag atg cag gag gag gac      2098
Ser Gln Leu Glu Leu Phe Tyr Cys Leu Tyr Glu Met Gln Glu Glu Asp
                630                 635                 640 ttc gtg caa agg gcc atg gac tat ttc ccc aag att gag atc aat ctc      2146
Phe Val Gln Arg Ala Met Asp Tyr Phe Pro Lys Ile Glu Ile Asn Leu
                645                 650                 655 tcc acc aga atg gac cac atg gtt tct tcc ttt tgc att gag aac tgt      2194
Ser Thr Arg Met Asp His Met Val Ser Ser Phe Cys Ile Glu Asn Cys
                660                 665                 670 cat cgg gtg gag tca ctg tcc ctg ggg ttt ctc cat aac atg ccc aag      2242
His Arg Val Glu Ser Leu Ser Leu Gly Phe Leu His Asn Met Pro Lys
675                 680                 685 gag gaa gag gag gag gaa aag gaa ggc cga cac ctt gat atg gtg cag      2290
Glu Glu Glu Glu Glu Glu Lys Glu Gly Arg His Leu Asp Met Val Gln
690                 695                 700                 705 tgt gtc ctc cca agc tcc tct cat gct gcc tgt tct cat ggg              2332
Cys Val Leu Pro Ser Ser Ser His Ala Ala Cys Ser His Gly
                710                 715 taaggaaact cggcttccag gtgcttcctc ctgcttcctc gccagcttct tcttggcgct    2392
tgcctcctct catctctttt caactatctt ccaaatactg ttgccacagc tacatcataa    2452
tgccaccact gtctgtttga gactccttca tgagcaaaga ttgatgtatg gtaggtggat    2512
aaatgggatg ag                                                        2524

<210> SEQ ID NO 59
<211> LENGTH: 719
<212> TYPE: PRT
<213> ORGANISM: Homo sapiens
<220> FEATURE:
<221> NAME/KEY: VARIANT
<222> LOCATION: 44, 45, 46, 47, 48, 49, 50, 51, 52, 53, 54, 55, 56, 57,
      58, 59, 60, 61, 62, 63, 64, 65, 66, 67, 68, 69, 70, 71
<223> OTHER INFORMATION: Xaa = Any Amino Acid
<220> FEATURE:
<221> NAME/KEY: VARIANT
<222> LOCATION: 72, 73, 74, 75, 76, 77, 78, 79, 80, 81, 82, 83, 84, 85,
      86, 87, 88, 89, 90, 91, 92, 93, 94, 95
<223> OTHER INFORMATION: Xaa = Any Amino Acid
```

```
<400> SEQUENCE: 59

Met Lys Met Ala Ser Thr Arg Cys Lys Leu Ala Arg Tyr Leu Glu Asp
 1               5                  10                  15

Leu Glu Asp Val Asp Leu Lys Lys Phe Lys Met His Leu Glu Asp Tyr
                20                  25                  30

Pro Pro Gln Lys Gly Cys Ile Pro Leu Pro Arg Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Ser
                    85                  90                  95

Asp Asn Ala Arg Val Ser Asn Pro Thr Val Ile Cys Gln Glu Asp Ser
                100                 105                 110

Ile Glu Glu Glu Trp Met Gly Leu Leu Glu Tyr Leu Ser Arg Ile Ser
                115                 120                 125

Ile Cys Lys Met Lys Lys Asp Tyr Arg Lys Lys Tyr Arg Lys Tyr Val
130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
                180                 185                 190

Thr Lys Thr Cys Glu Ser Pro Val Ser Pro Ile Lys Met Glu Leu Leu
                195                 200                 205

Phe Asp Pro Asp Asp Glu His Ser Glu Pro Val His Thr Val Val Phe
                210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
                260                 265                 270

Gly Asp Leu Ile Met Ser Cys Cys Pro Asp Pro Asn Pro Ile His
                275                 280                 285

Lys Ile Val Arg Lys Pro Ser Arg Ile Leu Phe Leu Met Asp Gly Phe
                290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
                340                 345                 350

Val Ala Leu Glu Lys Leu Gln His Leu Leu Asp His Pro Arg His Val
                355                 360                 365

Glu Ile Leu Gly Phe Ser Glu Ala Lys Arg Lys Glu Tyr Phe Phe Lys
                370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415
```

```
Ile Val Cys Thr Gly Leu Lys Gln Gln Met Glu Ser Gly Lys Ser Leu
            420                 425                 430

Ala Gln Thr Ser Lys Thr Thr Thr Ala Val Tyr Val Phe Phe Leu Ser
            435                 440                 445

Ser Leu Leu Gln Pro Arg Gly Ser Gln Glu His Gly Leu Cys Ala
    450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
            515                 520                 525

Phe Ala Ala Met Tyr Tyr Leu Leu Glu Glu Lys Glu Gly Arg Thr
    530                 535                 540

Asn Val Pro Gly Ser Arg Leu Lys Leu Pro Ser Arg Asp Val Thr Val
545                 550                 555                 560

Leu Leu Glu Asn Tyr Gly Lys Phe Glu Lys Gly Tyr Leu Ile Phe Val
                565                 570                 575

Val Arg Phe Leu Phe Gly Leu Val Asn Gln Glu Arg Thr Ser Tyr Leu
            580                 585                 590

Glu Lys Lys Leu Ser Cys Lys Ile Ser Gln Gln Ile Arg Leu Glu Leu
            595                 600                 605

Leu Lys Trp Ile Glu Val Lys Ala Lys Ala Lys Leu Gln Ile Gln
    610                 615                 620

Pro Ser Gln Leu Glu Leu Phe Tyr Cys Leu Tyr Glu Met Gln Glu Glu
625                 630                 635                 640

Asp Phe Val Gln Arg Ala Met Asp Tyr Phe Pro Lys Ile Glu Ile Asn
            645                 650                 655

Leu Ser Thr Arg Met Asp His Met Val Ser Ser Phe Cys Ile Glu Asn
            660                 665                 670

Cys His Arg Val Glu Ser Leu Ser Leu Gly Phe Leu His Asn Met Pro
    675                 680                 685

Lys Glu Glu Glu Glu Glu Lys Glu Gly Arg His Leu Asp Met Val
    690                 695                 700

Gln Cys Val Leu Pro Ser Ser His Ala Ala Cys Ser His Gly
705                 710                 715

<210> SEQ ID NO 60
<211> LENGTH: 317
<212> TYPE: PRT
<213> ORGANISM: Homo sapiens

<400> SEQUENCE: 60

Leu Thr Val Val Leu Gln Gly Pro Ala Gly Ile Gly Lys Thr Met Ala
1               5                   10                  15

Ala Lys Lys Ile Leu Tyr Asp Trp Ala Ala Gly Lys Leu Tyr Gln Gly
            20                  25                  30

Gln Val Asp Phe Ala Phe Phe Met Pro Cys Gly Glu Leu Leu Glu Arg
        35                  40                  45

Pro Gly Thr Arg Ser Leu Ala Asp Leu Ile Leu Asp Gln Cys Pro Asp
    50                  55                  60

Arg Gly Ala Pro Val Pro Gln Met Leu Ala Gln Pro Gln Arg Leu Leu
65                  70                  75                  80
```

```
Phe Ile Leu Asp Gly Ala Asp Glu Leu Pro Ala Leu Gly Gly Pro Glu
                85                  90                  95

Ala Ala Pro Cys Thr Asp Pro Phe Glu Ala Ser Gly Ala Arg Val
            100                 105                 110

Leu Gly Gly Leu Leu Ser Lys Ala Leu Leu Pro Thr Ala Leu Leu Leu
            115                 120                 125

Val Thr Thr Arg Ala Ala Pro Gly Arg Leu Gln Gly Arg Leu Cys
130                 135                 140

Ser Pro Gln Cys Ala Glu Val Arg Gly Phe Ser Asp Lys Asp Lys Lys
145                 150                 155                 160

Lys Tyr Phe Tyr Lys Phe Phe Arg Asp Glu Arg Ala Glu Arg Ala
                165                 170                 175

Tyr Arg Phe Val Lys Glu Asn Glu Thr Leu Phe Ala Leu Cys Phe Val
                180                 185                 190

Pro Phe Val Cys Trp Ile Val Cys Thr Val Leu Arg Gln Gln Leu Glu
                195                 200                 205

Leu Gly Arg Asp Leu Ser Arg Thr Ser Lys Thr Thr Thr Ser Val Tyr
            210                 215                 220

Leu Leu Phe Ile Thr Ser Val Leu Ser Ser Ala Pro Val Ala Asp Gly
225                 230                 235                 240

Pro Arg Leu Gln Gly Asp Leu Arg Asn Leu Cys Arg Leu Ala Arg Glu
                245                 250                 255

Gly Val Leu Gly Arg Arg Ala Gln Phe Ala Glu Lys Glu Leu Glu Gln
            260                 265                 270

Leu Glu Leu Arg Gly Ser Lys Val Gln Thr Leu Phe Leu Ser Lys Lys
            275                 280                 285

Glu Leu Pro Gly Val Leu Glu Thr Glu Val Thr Tyr Gln Phe Ile Asp
290                 295                 300

Gln Ser Phe Gln Glu Phe Leu Ala Ala Leu Ser Tyr Leu
305                 310                 315

<210> SEQ ID NO 61
<211> LENGTH: 290
<212> TYPE: PRT
<213> ORGANISM: Homo sapiens

<400> SEQUENCE: 61

Val Leu Ser Tyr Cys Val Arg Cys Cys Pro Ala Gly Gln Ala Leu Arg
1               5                   10                  15

Leu Ile Ser Cys Arg Leu Val Ala Ala Gln Glu Lys Lys Lys Lys Ser
                20                  25                  30

Leu Gly Lys Arg Leu Gln Ala Ser Leu Gly Gly Gly Ser Trp Leu Gly
            35                  40                  45

Thr Gln Leu Ala Pro Glu Val Pro Phe Arg Pro Pro Cys Cys Asp Ile
50                  55                  60

Cys Pro Thr Pro Pro Asp Pro Arg Leu Leu Gln Gly Lys Ala Phe
65                  70                  75                  80

Ala Arg Val Pro Leu Asn Ile Ala Pro Ile Gln Pro Leu Pro Arg Gly
                85                  90                  95

Leu Ala Ser Val Glu Arg Met Asn Val Thr Val Leu Ala Gly Ala Gly
            100                 105                 110

Pro Gly Asp Pro Lys Thr His Ala Met Thr Asp Pro Leu Cys His Leu
            115                 120                 125

Ser Ser Leu Thr Leu Ser His Cys Lys Leu Pro Asp Ala Val Cys Arg
130                 135                 140
```

```
Asp Leu Ser Glu Ala Leu Arg Ala Ala Pro Ala Leu Thr Glu Leu Gly
145                 150                 155                 160

Leu Leu His Asn Arg Leu Ser Glu Ala Gly Leu Arg Met Leu Ser Glu
                165                 170                 175

Gly Leu Ala Trp Pro Gln Cys Arg Val Gln Thr Val Arg Val Gln Leu
            180                 185                 190

Pro Asp Pro Gln Arg Gly Leu Gln Tyr Leu Val Gly Met Leu Arg Gln
        195                 200                 205

Ser Pro Ala Leu Thr Thr Leu Asp Leu Ser Gly Cys Gln Leu Pro Ala
    210                 215                 220

Pro Met Val Thr Tyr Leu Cys Ala Val Leu Gln His Gln Gly Cys Gly
225                 230                 235                 240

Leu Gln Thr Leu Ser Leu Ala Ser Val Glu Leu Ser Glu Gln Ser Leu
                245                 250                 255

Gln Glu Leu Gln Ala Val Lys Arg Ala Lys Pro Asp Leu Val Ile Thr
            260                 265                 270

His Pro Ala Leu Asp Gly His Pro Gln Pro Lys Glu Leu Ile Ser
        275                 280                 285

Thr Phe
    290

<210> SEQ ID NO 62
<211> LENGTH: 181
<212> TYPE: PRT
<213> ORGANISM: Homo sapiens

<400> SEQUENCE: 62

Ile Cys Leu His Gly Val Gly Trp His Trp Lys Asp Asn Ser Arg Gln
1               5                   10                  15

Lys Lys Val Leu Asp Trp Ala Thr Gly Thr Leu Tyr Pro Gly Arg Phe
            20                  25                  30

Asp Tyr Val Phe Tyr Val Ser Cys Lys Glu Val Val Leu Leu Leu Glu
        35                  40                  45

Ser Lys Leu Glu Gln Leu Leu Phe Trp Cys Cys Gly Asp Asn Gln Ala
    50                  55                  60

Pro Val Thr Glu Ile Leu Arg Gln Pro Glu Arg Leu Leu Phe Ile Leu
65                  70                  75                  80

Asp Gly Phe Asp Glu Leu Gln Arg Pro Phe Glu Lys Leu Lys Lys
            85                  90                  95

Arg Gly Leu Ser Pro Lys Glu Ser Leu Leu His Leu Leu Ile Arg Arg
            100                 105                 110

His Thr Leu Pro Thr Cys Ser Leu Leu Ile Thr Thr Arg Pro Leu Ala
        115                 120                 125

Leu Arg Asn Leu Glu Pro Leu Leu Lys Gln Ala Arg His Val His Ile
    130                 135                 140

Leu Gly Phe Ser Glu Glu Glu Arg Ala Arg Tyr Phe Ser Ser Tyr Phe
145                 150                 155                 160

Thr Asp Glu Lys Gln Ala Asp Arg Ala Phe Asp Ile Val Gln Lys Asn
                165                 170                 175

Asp Ile Leu Tyr Lys
            180

<210> SEQ ID NO 63
<211> LENGTH: 190
<212> TYPE: PRT
<213> ORGANISM: Homo sapiens
```

```
<400> SEQUENCE: 63

Pro Arg Thr Val Val Met Gln Gly Ala Ala Gly Ile Gly Lys Ser Met
1               5                   10                  15

Leu Ala His Lys Val Met Leu Asp Trp Ala Asp Gly Lys Leu Phe Gln
            20                  25                  30

Gly Arg Phe Asp Tyr Leu Phe Tyr Ile Asn Cys Arg Glu Met Asn Gln
        35                  40                  45

Ser Ala Thr Glu Cys Ser Met Gln Asp Leu Ile Phe Ser Cys Trp Pro
50                  55                  60

Glu Pro Ser Ala Pro Leu Gln Glu Leu Ile Arg Val Pro Glu Arg Leu
65                  70                  75                  80

Leu Phe Ile Ile Asp Gly Phe Asp Glu Leu Lys Pro Ser Phe His Asp
                85                  90                  95

Pro Gln Gly Pro Trp Cys Leu Cys Trp Glu Lys Arg Pro Thr Glu
            100                 105                 110

Leu Leu Leu Asn Ser Leu Ile Arg Lys Lys Leu Leu Pro Glu Leu Ser
            115                 120                 125

Leu Leu Ile Thr Thr Arg Pro Thr Ala Leu Glu Lys Leu His Arg Leu
130                 135                 140

Leu Glu His Pro Arg His Val Glu Ile Leu Gly Phe Ser Glu Ala Glu
145                 150                 155                 160

Arg Lys Glu Tyr Phe Tyr Lys Tyr Phe His Asn Ala Glu Gln Ala Gly
                165                 170                 175

Gln Val Phe Asn Tyr Val Arg Asp Asn Glu Pro Leu Phe Thr
            180                 185                 190

<210> SEQ ID NO 64
<211> LENGTH: 603
<212> TYPE: PRT
<213> ORGANISM: Homo sapiens

<400> SEQUENCE: 64

Pro Asn Gln Arg Gly Leu Cys Ser Leu Ala Ala Asp Gly Leu Trp Asn
1               5                   10                  15

Gln Lys Ile Leu Phe Glu Glu Gln Asp Leu Arg Lys His Gly Leu Asp
            20                  25                  30

Gly Glu Asp Val Ser Ala Phe Leu Asn Met Asn Ile Phe Gln Lys Asp
        35                  40                  45

Ile Asn Cys Glu Arg Tyr Tyr Ser Phe Ile His Leu Ser Phe Gln Glu
50                  55                  60

Phe Phe Ala Ala Met Tyr Tyr Ile Leu Asp Glu Gly Glu Gly Gly Ala
65                  70                  75                  80

Gly Pro Asp Gln Asp Val Thr Arg Leu Leu Thr Glu Tyr Ala Phe Ser
                85                  90                  95

Glu Arg Ser Phe Leu Ala Leu Thr Ser Arg Phe Leu Phe Gly Leu Leu
            100                 105                 110

Asn Glu Glu Thr Arg Ser His Leu Glu Lys Ser Leu Cys Trp Lys Val
            115                 120                 125

Ser Pro His Ile Lys Met Asp Leu Leu Gln Trp Ile Gln Ser Lys Ala
130                 135                 140

Gln Ser Asp Gly Ser Thr Leu Gln Gln Gly Ser Leu Glu Phe Phe Ser
145                 150                 155                 160

Cys Leu Tyr Glu Ile Gln Glu Glu Glu Phe Ile Gln Gln Ala Leu Ser
                165                 170                 175
```

-continued

```
His Phe Gln Val Ile Val Ser Asn Ile Ala Ser Lys Met Glu His
                180                 185                 190

Met Val Ser Ser Phe Cys Leu Lys Arg Cys Arg Ser Ala Gln Val Leu
            195                 200                 205

His Leu Tyr Gly Ala Thr Tyr Ser Ala Asp Gly Glu Asp Arg Ala Arg
            210                 215                 220

Cys Ser Ala Gly Ala His Thr Leu Leu Val Gln Leu Arg Pro Glu Arg
225                 230                 235                 240

Thr Val Leu Leu Asp Ala Tyr Ser Glu His Leu Ala Ala Leu Cys
                245                 250                 255

Thr Asn Pro Asn Leu Ile Glu Leu Ser Leu Tyr Arg Asn Ala Leu Gly
                260                 265                 270

Ser Arg Gly Val Lys Leu Leu Cys Gln Gly Leu Arg His Pro Asn Cys
            275                 280                 285

Lys Leu Gln Asn Leu Arg Leu Lys Arg Cys Arg Ile Ser Ser Ser Ala
            290                 295                 300

Cys Glu Asp Leu Ser Ala Ala Leu Ile Ala Asn Lys Asn Leu Thr Arg
305                 310                 315                 320

Met Asp Leu Ser Gly Asn Gly Val Gly Phe Pro Gly Met Met Leu Leu
                325                 330                 335

Cys Glu Gly Leu Arg His Pro Gln Cys Arg Leu Gln Met Ile Gln Leu
                340                 345                 350

Arg Lys Cys Gln Leu Glu Ser Gly Ala Cys Gln Glu Met Ala Ser Val
            355                 360                 365

Leu Gly Thr Asn Pro His Leu Val Glu Leu Asp Leu Thr Gly Asn Ala
370                 375                 380

Leu Glu Asp Leu Gly Leu Arg Leu Leu Cys Gln Gly Leu Arg His Pro
385                 390                 395                 400

Val Cys Arg Leu Arg Thr Leu Trp Leu Lys Ile Cys Arg Leu Thr Ala
                405                 410                 415

Ala Ala Cys Asp Glu Leu Ala Ser Thr Leu Ser Val Asn Gln Ser Leu
            420                 425                 430

Arg Glu Leu Asp Leu Ser Leu Asn Glu Leu Gly Asp Leu Gly Val Leu
            435                 440                 445

Leu Leu Cys Glu Gly Leu Arg His Pro Thr Cys Lys Leu Gln Thr Leu
450                 455                 460

Arg Leu Gly Ile Cys Arg Leu Gly Ser Ala Ala Cys Glu Gly Leu Ser
465                 470                 475                 480

Val Val Leu Gln Ala Asn His Asn Leu Arg Glu Leu Asp Leu Ser Phe
                485                 490                 495

Asn Asp Leu Gly Asp Trp Gly Leu Trp Leu Leu Ala Glu Gly Leu Gln
            500                 505                 510

His Pro Ala Cys Arg Leu Gln Lys Leu Trp Leu Asp Ser Cys Gly Leu
            515                 520                 525

Thr Ala Lys Ala Cys Glu Asn Leu Tyr Phe Thr Leu Gly Ile Asn Gln
            530                 535                 540

Thr Leu Thr Asp Leu Tyr Leu Thr Asn Asn Ala Leu Gly Asp Thr Gly
545                 550                 555                 560

Val Arg Leu Leu Cys Lys Arg Leu Ser His Pro Gly Cys Lys Leu Arg
                565                 570                 575
```

-continued

```
Val Leu Trp Leu Phe Gly Met Asp Leu Asn Lys Met Thr His Ser Arg
            580                 585                 590

Leu Ala Ala Leu Arg Val Thr Lys Pro Tyr Leu
        595                 600
```

NUCLEIC ACID MOLECULE ENCODING A PANG6 POLYPEPTIDE

This application is a continuation of U.S. Ser. No. 09/965,621, filed Sep. 25, 2001, now abandoned, which claims the benefit of U.S. Provisional Application No. 60/367,367, filed Sep. 26, 2000 now abandoned, which was converted from U.S. Ser. No. 09/671,760, and which is incorporated herein by reference in its entirety.

This invention was made in part with United States Government support under grant number NIH GM60049 and GM61694 awarded by the National Institutes of Health and NSF DBI-0078731 awarded by National Science Foundation. The U.S. Government has certain rights in this invention.

BACKGROUND OF THE INVENTION

1. Field of the Invention

This invention related generally to the fields of molecular biology and molecular medicine and more specifically to the identification of proteins involved in programmed cell death, cytokine processing and receptor signal transduction, and associations of these proteins.

2. Background Information

Programmed cell death is a physiologic process that ensures homeostasis is maintained between cell production and cell turnover in essentially all self-renewing tissues. In many cases, characteristic morphological changes, termed "apoptosis," occur in a dying cell. Since similar changes occur in different types of dying cells, cell death appears to proceed through a common pathway in different cell types.

In addition to maintaining tissue homeostasis, apoptosis also occurs in response to a variety of external stimuli, including growth factor deprivation, alterations in calcium levels, free-radicals, cytotoxic lymphokines, infection by some viruses, radiation and most chemotherapeutic agents. Thus, apoptosis is an inducible event that likely is subject to similar mechanisms of regulation as occur, for example, in a metabolic pathway. In this regard, dysregulation of apoptosis also can occur and is observed, for example, in some types of cancer cells, which survive for a longer time than corresponding normal cells, and in neurodegenerative diseases where neurons die prematurely. In viral infections, induction of apoptosis can figure prominently in the pathophysiology of the disease process, because immune-based eradication of viral infections depend on elimination of virus-producing host cells by immune cell attack resulting in apoptosis.

Some of the proteins involved in programmed cell death have been identified and associations among some of these proteins have been described. However, additional apoptosis regulating proteins remain to be found and the mechanisms by which these proteins mediate their activity remains to be elucidated. The identification of the proteins involved in cell death and an understanding of the associations between these proteins can provide a means for manipulating the process of apoptosis in a cell and, therefore, selectively regulating the relative lifespan of a cell or its relative resistance to cell death stimuli.

The identification of new proteins or new domains within known proteins, and the elucidation of the proteins with which they interact, therefore, can form the basis for strategies designed to alter apoptosis, cytokine production, cytokine receptor signaling, and other cellular processes. Thus, a need exists to identify novel apoptosis-related domains within both novel and known proteins. The present invention satisfies this need and provides additional advantages as well.

SUMMARY OF THE INVENTION

The invention provides isolated nucleic acid molecules encoding PAAD-domain containing polypeptides and functional fragments thereof, including fragments containing PAAD domains, NB-ARC domains and LRR domains. Also provided are vectors containing such nucleic acid molecules and host cells containing the vectors. Also provided are oligonucleotides therefrom and methods of identifying nucleic acid molecules encoding a PAAD-containing polypeptide in a sample using such oligonucleotides.

Also provided are isolated PAAD-domain containing polypeptides and functional fragments thereof, including fragments containing PAAD domains, NB-ARC domains and LRR domains, and peptides therefrom.

The invention further provides antibodies that can specifically bind to PAAD-domain containing polypeptides, and methods of detecting PAAD-domain containing polypeptides in a sample using such antibodies.

Also provided is a method of identifying a polypeptide that associates with a PAAD-domain containing polypeptide or fragment thereof, including fragments containing PAAD domains, NB-ARC domains and LRR domains. The method is practiced by contacting a PAAD domain-containing polypeptide or fragment with a candidate PAAD domain-containing polypeptide-associated polypeptide (PAP), and detecting association of the PAAD domain-containing polypeptide or fragment with the candidate PAP, wherein a candidate PAP that associates with the polypeptide is identified as a PAP.

The invention also provides a method of identifying an effective agent that alters the association of a PAAD domain-containing polypeptide or fragment with a PAP. The method is practiced by contacting a PAAD domain-containing polypeptide, or a PAAD, NB-ARC or LRR domain therefrom, and the PAP under conditions that allow the PAAD domain-containing polypeptide or fragment and the PAP to associate, with a candidate agent, and detecting the altered association of the PAAD domain-containing polypeptide or domain with the PAP, wherein an agent that alters the association is identified as a effective agent.

Further provided is a method for identifying an agent that associates with a PAAD domain-containing polypeptide or fragment therefrom, including a fragment containing a PAAD domain, NB-ARC domain or LRR domains. The method is practiced by contacting the PAAD domain-containing polypeptide or fragment with a candidate agent and detecting association of the PAAD domain-containing polypeptide with the agent.

Also provided is a method of identifying an agent that modulates PAAD domain-mediated inhibition of NFκB activity. The method is practiced by contacting a cell that recombinantly expresses a PAAD domain-containing polypeptide with a candidate agent and detecting NFκB activity in the cell. Increased or decreased NFκB activity in the cell compared to a control cell indicates that the candidate agent is an agent that modulates PAAD domain-mediated inhibition of NFκB activity.

Further provided is a method of identifying an agent that modulates an activity of a NB-ARC domain of a PAAD domain-containing polypeptide. The method is practiced by contacting an NB-ARC domain-containing polypeptide with a candidate agent and detecting an activity of the NB-ARC domain, wherein an increase or decrease of the activity identifies the agent as an agent that modulates the activity of the NB-ARC domain. The detected activity of the NB-ARC domain can be selected from homo-oligomerization, hetero-oligomerization, nucleotide hydrolysis, and nucleotide binding.

Further provided is a method of modulating NFκB transcriptional activity in a cell. The method is practiced by introducing a nucleic acid molecule encoding a PAAD domain-containing polypeptide into a cell and expressing the nucleic acid molecule in the cell, wherein the expression of the nucleic acid modulates NFκB transcriptional activity in the cell.

The invention also provides a method of decreasing expression of a PAAD domain-containing polypeptide in a cell, by introducing an antisense or dsRNA nucleic molecule into a cell, wherein the antisense or dsRNA nucleic molecule binds to a nucleic acid molecule encoding a PAAD domain-containing polypeptide.

BRIEF DESCRIPTION OF THE FIGURES

FIG. 1 shows that multiple alignment using the CLUSTAL W program (Higgins et al. *Nuc. Acid Res.* 22:4673–4680 (1995)) of the aligned part of selected members of the PAAD family from humans. NCBI gi accession numbers are included. The "sec_str" line shows secondary structure prediction made for pyrin using the PHD program (Rost et al., *Comput. Appl. Biosci.* 10:53–60 (1994)).

DETAILED DESCRIPTION OF THE INVENTION

Figure 4:
FIG. 4 shows a model of the PAAD domain built on the template of the Death Effector Domain from FADD protein (PDB code: 1alz), using the FFAS alignment and the Modeller program (Sali et al, *J. Mol. Biol.* 234:779–815 (1993)). Some motifs identified in the sequence analyses of the PAAD family stand out as surface features that may be responsible for biological activity of these domains. A notable feature is the conserved Lys-Phe-Lys motif, that according to this model, is found on the protein surface, in helix 2. Positively charged residues from this motif, together with other charged residues from another, less conserved motif in helix 5, form a positively charged surface of the predicted protein that may be important for inter-molecule interaction. These residues are shown in the ball-and-stick representation.

In accordance with the present invention, there are provided PAAD domain-containing polypeptides and functional fragments thereof, encoding nucleic acid molecules, and related compositions and methods. The "PAAD domain" is an 80–100 residue domain named after the protein families in which it was first identified: pyrin, AIM (Absent-in-melanoma), ASC (apoptosis-associated speck-like protein containing a caspase recruitment domain), and death domain (DD)-like. The terms "PAAD" and "PACS" (for identified in Pyrin, AIM, Caspase, and Speck-like protein) are synonymous. Secondary structural predictions identify the PAAD domain as mostly helical (see FIG. 1). The PAAD domain has the predicted tertiary structure shown in FIG. 4, identifying PAAD as a member of the Death Domain (DD), Death Effector Domain (DED), Caspase Recruitment Domain (CARD) family. PAAD domains have been identified at the N-terminus of several different proteins involved in apoptosis, cancer, inflammation and immune responses, as described herein (see FIG. 1).

Protein-protein interactions influence the activity of various proteins involved in apoptosis. Several protein interaction domains have been implicated in interactions among some apoptosis-regulating proteins. In accordance with the present invention, the PAAD domain has been identified at the N-terminus of the recently identified caspase-homologous gene from zebrafish (Inohara et al., *Cell Death Differ*, 7:509–510 (2000), suggesting the involvement of the PAAD domain in apoptosis. In this protein, the PAAD domain occupies a position corresponding to the prodomain, which in other caspase genes is occupied by a CARD (caspase recruitment domain) or a DED (death effector domain) domain. Thus, it is contemplated herein that the PAAD domain functions as a death domain in apoptosis. Accordingly, methods are provided herein for identifying PAAD domain binding agents that modulate apoptotic activity.

As disclosed herein, PAAD domain-containing polypeptides bind proteins through their PAAD domains, including other PAAD domain-containing polypeptide, IKAP, Nod1, Cardiak, NIK and IKK-i.

Accordingly, methods are provided herein for identifying PAAD domain-associating proteins, and for identifying compounds that disrupt the interaction between the PAAD domain and PAAD domain-associating proteins.

As disclosed herein, expression of the PAAD domain of PAAD domain-containing polypeptide is able to specifically modulate the induction of NFκB activity by various stimuli. NFκB is the collective name for inducible dimeric transcription factors composed of members of the Rel family of DNA-binding proteins that recognize a common sequence motif. NFκB is sequestered in the cytoplasm of resting cells through its association with an inhibitory protein called IκB. When stimulated by a variety of extracellular modulators, including the proinflammatory cytokines TNFα and IL-1, T- and B-cell mitogens, bacteria, bacterial lipopolysaccharide (LPS), viruses, viral proteins, double stranded RNA, and physical and chemical stresses, a cascade of adaptor proteins and protein kinases is activated, leading to phosphorylation of IκB by the IκB kinases α and β (IKKα/β). IκB phosphorylation leads to its ubiquitination, which targets the protein for rapid degradation by the 26S proteasome. The degradation if IκB exposes the nuclear localization signal (NLS) of NFκB, resulting in NFκB translocation to the nucleus and activation.

Active NFκB regulates the transcription of a large number of genes, including those involved in immune and inflammatory responses such as immunoreceptors, cell adhesion molecules, cytokines and chemokines. NFκB also plays an important role in the antiviral response through interferon gene induction. Through adaptation, many viruses that do not cause interferon induction exploit NFκB to activate their own genes and to stimulate the survival and proliferation of lymphoid cells in which they replicate.

NFκB can have either positive and negative effects on cellular apoptosis depending on the cell type, apoptotic stimulus, and timing of NFκB activation. NFκB regulates the transcription of a variety of genes involved in blocking apoptosis, including cellular inhibitor of apopotosis (cIAP)-1, cIAP-2, TRAF1, TRAF2, superoxide dismutase (SOD), A20, and the Bcl-2 homolog Bfl-1/A1.

Inappropriate regulation of NFκB is involved in a wide range of human disorders, including cancers, neurodegenerative disorders, ataxia-telangiectasia, arthritis, asthma, inflammatory bowel disease and numerous other inflammatory conditions (see Karin et al., *Ann. Rev. Immunol.* 18:621–663 (2000), and references therein). Activation of NFκB also correlates with resistance to apoptosis induced by cancer therapeutic agents.

Accordingly, methods are provided herein to identify agents that modulate, either positively or negatively, the PAAD domain-mediated modulation of NFκB activation. Such agents can thus be used to regulate inflammatory responses, immune responses (including autoimmune responses), apoptosis, and other processes mediated at least in part by NF κB activity.

Further, PAAD domain-containing polypeptide are contemplated herein as influencing a variety of cellular and biochemical processes beyond apoptosis, including cell adhesion, inflammation and cytokine receptor signaling, and responses to viruses and infectious agents.

Figure 3:
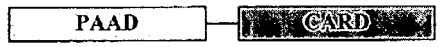
FIG. 3 shows a schematic (not to scale) representation of domain arrangement in proteins containing a PAAD domain.
Figure 3:
Figure 3:
Figure 3:
Figure 3:
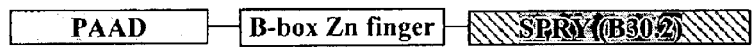
Figure 3:
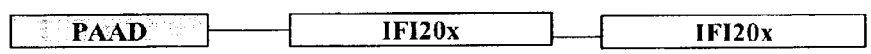
Figure 3:
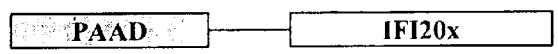
Figure 3:

Exemplary invention PAAD domain-containing polypeptides include a family of proteins that in addition to a PAAD domain, contain a domain similar to the recently identified NB-ARC (NACHT) NTP-ase family (Koonin et al., *Trends Biochem Sci,* 25:223–224 (2000)) (see FIG. 3). The NACHT domain has been implicated in nucleotide binding, oligomerization, and nucleotide (e.g. ATP and/or GTP) hydrolysis. This family of proteins is referred to herein as PAAD and Nucleotide-binding ("PAN") proteins. The amino acid sequence of the PAAD domains of PAN1 through PAN6 are set forth in FIG. 1 and as SEQ ID NOS:1–6, respectively.

The sequences of PAN2–6 cDNAs and encoded polypeptides are set forth as follows: PAN2: SEQ ID NOS:15 and 16; PAN3: SEQ ID NOS: 17 and 18; PAN4: SEQ ID NOS:19 and 20; PAN5: SEQ ID NOS:21 and 22; PAN6: SEQ ID NOS:23 and 24.

Figure 1:
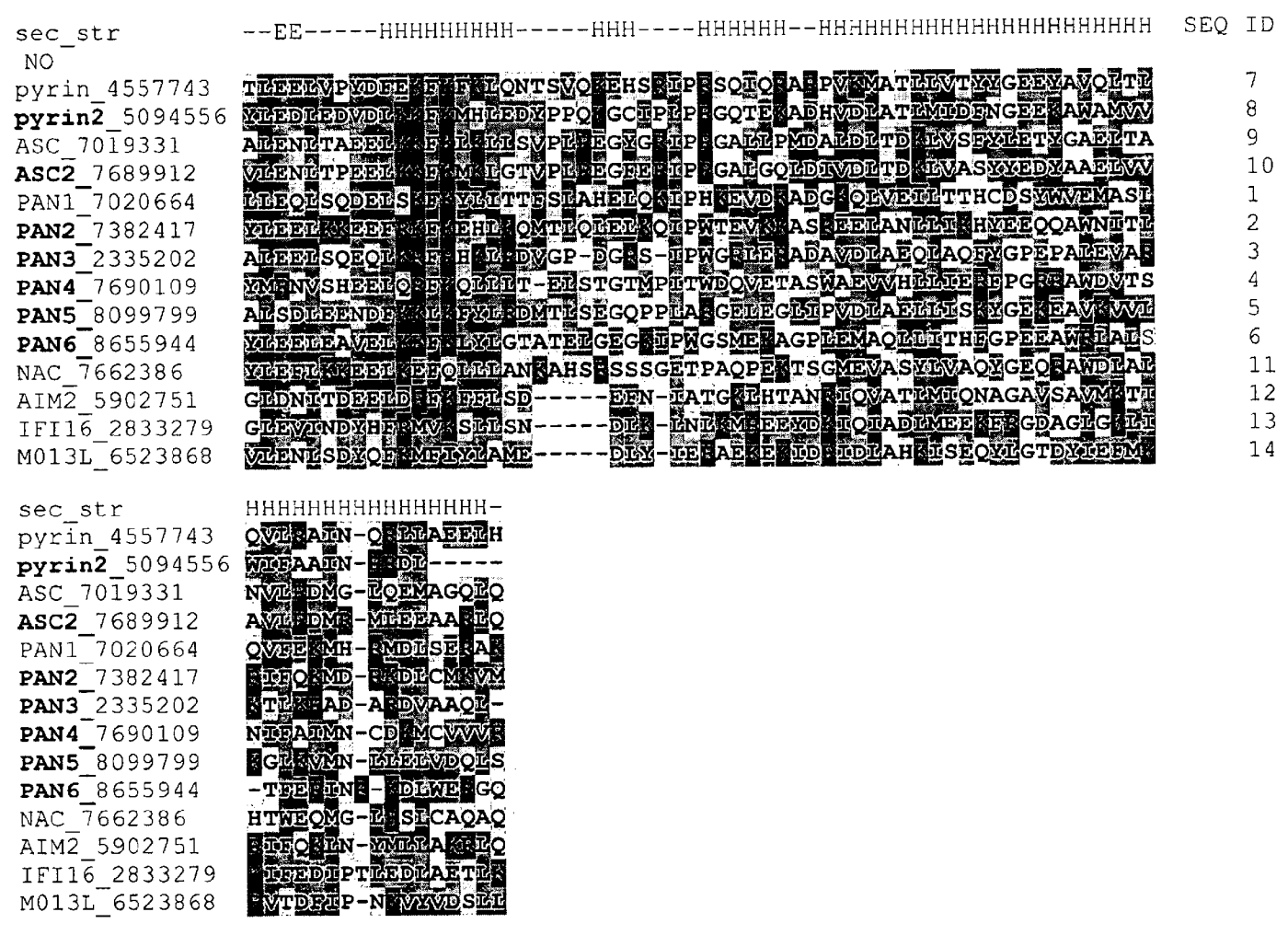

Other invention PAAD domain-containing polypeptides include pyrin2 and human ASC2, whose PAAD domain sequences are set forth in FIG. 1 and as SEQ ID NOS:8 and 10, respectively. The sequences or pyrin2 cDNA and encoded polypeptide are set forth as SEQ ID NOS:25 and 26. A 719 residue open reading frame from chromosome 1, which is identical over the N-terminal 41 amino acids with SEQ ID NO:26, has been identified and deposited as gi:14731966 (SEQ ID NOS:58 and 59). Accordingly, a PAAD domain-containing polypeptide can contain the first 41 amino acids of SEQ ID NO:26, and can optionally further comprise the amino acid sequence designated SEQ ID NO:59.

The sequences of ASC2 cDNA and encoded polypeptide are set forth as SEQ ID NOS:27 and 28. ASC2 is an 89-residue protein containing only the PAAD domain.

In accordance with the present invention, the PAAD domain has also been identified in the N-terminal part of "Absent in Melanoma-2" (AIM2) and several closely homologous human and murine proteins, such as interferon-inducible genes IFI16 and MNDA (DeYoung et al., *Oncogene,* 15:453–457 (1997) (see FIG. 1; SEQ ID NOS:12 and 13). Proteins from this family were characterized as containing one or more copies of a conserved 200-residue domain, implicated in transcription repression (Johnstone et al., *J Biol. Chem.* 273:17172–17177 (1998). The N-terminal part of AIM2 and related homoloogous proteins, containing the invention PAAD domain was not functionally analyzed, with two exceptions. In MNDA protein, it was shown that the N-terminal domain is partly responsible for homodimerization (Xie et al., *FEBS Lett.* 408:151–155 (1997). In IFI16, DNA-binding was attributed to a 159-residue long N-terminal segment (Dawson et al. *Biochem Biophys Res Commun,* 214:152–162 (1995)). There are also two viral proteins homologous to the interferon-inducible MNDA/IFI16 family, (M013L from myxoma virus and gp013L from rabbit fibroma virus), that contain an invention PAAD domain. The PAAD domain of M013L is shown in FIG. 1 (SEQ ID NO:14).

In accordance with the present invention, a PAAD domain has also been identified in the N-teminus of the ASC protein (apoptosis-associated speck-like protein containing a CARD) (Masumoto et al., *J Biol Chem,* 274:33835–33838 (1999)) (see FIG. 1; SEQ ID NO:9). The ASC protein was identified by characteristic dot-like aggregates (specks) which were present in cells during apoptosis triggered by retinolic acid and other anti-cancer drugs (Masumoto et al., supra (1999)). The C-terminal half of the speck protein contains an easily recognizable CARD domain, while the N-terminal half has now been found to be occupied by an invention PAAD domain.

One of the PAAD domain-containing polypeptides, PAN6 (SEQ ID NO:24), allowed an independent and unambigous connection between the pyrin/ASC/caspase and AIM2/IFI16 branches of the family. Three iterations of a standard PSI-BLAST search against the NCBI nr database starting from this putative domain pulled out, among others, pyrin and AIM2, with E-values of 1e-23 and 1e-18, respectively.

The average sequence similarity between different branches of the PAAD domain protein family is approximately 25% of sequence identity (see FIG. 1). However, clear amino acid regions of strong sequence similarity are conserved throughout the PAAD domain family of proteins.

Accordingly, in one embodiment, invention PAAD domains comprise the following amino acid consensus sequence motif -KFKX$_1$X$_2$L- (SEQ ID NO:29), where X$_1$ and $X_2$ can be any amino acid. Preferably $X_1$ is selected from amino acids F, M, L, Y, E, H, Q and S, and $X_2$ is preferably selected from amino acids K, H, L, Y and F. This motif has been found to be a present in the N-terminal half of the majority of invention PAAD domains (see e.g., FIG. 1).

In another embodiment, invention PAAD domains are also contemplated herein comprising the following amino acid consensus sequence motif -KLKX$_1$X$_2$L- (SEQ ID NO:30), where $X_1$ and $X_2$ can be any amino acid. Preferably, $X_1$ is selected from amino acids F, M, L, Y, E, H, Q and S, and $X_2$ is preferably selected from amino acids K, H, L, Y and F.

In yet another embodiment, invention PAAD domains are also contemplated herein comprising the following amino acid consensus sequence motif -RFRX$_1$X$_2$L- (SEQ ID NO:31), where $X_1$ and $X_2$ can be any amino acid. Preferably $X_1$ is selected from amino acids F, M, L, Y, E, H, Q and S, and $X_2$ is preferably selected from amino acids K, H, L, Y and F.

In yet another embodiment, invention PAAD domains are also contemplated herein comprising the following amino acid consensus sequence motif -RFKX$_1$X$_2$L- (SEQ ID NO:32), where $X_1$ and $X_2$ can be any amino acid. Preferably, $X_1$ is selected from amino acids F, M, L, Y, E, H, Q and S, and $X_2$ is preferably selected from amino acids K, H, L, Y and F.

In yet another embodiment, invention PAAD domains are also contemplated herein comprising the following amino acid consensus sequence motif -KFRX$_1$X$_2$L- (SEQ ID NO:33), where $X_1$ and $X_2$ can be any amino acid. Preferably, $X_1$ is selected from amino acids F, M, L, Y, E, H, Q and S, and $X_2$ is preferably selected from amino acids K, H, L, Y and F.

In still another embodiment, invention PAAD domains are also contemplated herein comprising the following amino acid consensus sequence motif -KFKX$_1$X$_2$I- (SEQ ID NO:34), where $X_1$ and $X_2$ can be any amino acid. Preferably, $X_1$ is selected from amino acids F, M, L, Y, E, H, Q and S, and $X_2$ is preferably selected from amino acids K, H, L, Y and F.

Accordingly, there are provided PAAD domain-containing polypeptides comprising an amino acid consensus sequence selected from the group consisting of:

-KFKX$_1$X$_2$L- (SEQ ID NO:29);
-KLKX$_1$X$_2$L- (SEQ ID NO:30);
-RFRX$_1$X$_2$L- (SEQ ID NO:31);
-RFKX$_1$X$_2$L- (SEQ ID NO:32);
-KFRX$_1$X$_2$L- (SEQ ID NO:33); and
-KFKX$_1$X$_2$I- (SEQ ID NO:34)

where $X_1$ and $X_2$ can be any amino acid. Preferably, $X_1$ is selected from amino acids F, M, L, Y, E, H, Q and S, and $X_2$ is preferably selected from amino acids K, H, L, Y and F.

PAAD domains can be present in an invention polypeptide fragment or chimeric protein in conjunction with other types of functional domains, thus providing a mechanism for bringing one or more functional domains into close proximity or contact with a target protein via PAAD:PAAD associations involving two PAAD-containing polypeptides. For example, the PAAD domains of invention PAN proteins (e.g., PAN-1 through PAN6) allows invention PAN proteins to self-associated forming homo- or hetero-oiligomers, thereby forming an oligomeric complex which brings proteins associated with PAN proteins into close proximity to each other. Because some PAAD domain-containing proteins also contain a CARD domain, exemplary proteins that are contemplated for association with invention PAN proteins are pro-caspases. Because most pro-caspases possess at least a small amount of protease activity even in their unprocessed form, the assembly of a complex that brings the proforms of caspase into juxtaposition can result in trans-processing of zymogens, producing the proteolytically processed and active caspase. Thus, invention PAN proteins can employ a PAAD domain for self-oligomerization and a CARD domain for binding a pro-caspase, resulting in caspase clustering, proteolytic processing and activation. In addition to the ability to activate caspases, PAAD domains are contemplated herein as being able to inhibit caspases.

In addition to their role in regulation of cell death and cell proliferation, PAAD domains can regulate other cellular processes. A PAAD domain-containing polypeptide can, for example, induce activation of the transcription factor NF-κB. Though caspase activation resulting from PAAD domain interactions can be involved in inducing apoptosis, other caspases can be primarily involved in proteolytic processing and activation of inflammatory cytokines (such as pro-IL-1b and pro-IL-18). Thus, PAAD domain-containing polypeptides can also be involved in cytokines receptor signaling, cytokine production and cJun N-terminal kinase activation, and, therefore, can be involved in regulation of immune and inflammatory responses.

In view of the function of the PAAD domain within the invention PAAD domain-containing polypeptides or functional fragments thereof, polypeptides of the invention are contemplated herein for use in methods to alter cellular and biochemical processes such as apoptosis, NF-κB induction, cytokine processing, cytokine receptor signaling, caspase-mediated proteolysis, or cJun N-terminal kinase activation, thus having modulating effects on cell life and death (i.e., apoptosis), inflammation, cell adhesion, or other cellular or biochemical processes.

Invention PAAD domain-containing polypeptides or functional fragments thereof are also contemplated in methods to identify PAAD domain binding agents and PAAD-associated polypeptides (PAPs) that alter apoptosis, NF-κB induction, cytokine processing, cytokine receptor signaling, caspase-mediated proteolysis, or cJun N-terminal kinase activation, thus having modulating effects on cell life and death (i.e., apoptosis), inflammation, cell adhesion, or other cellular or biochemical processes.

It is also contemplated herein that invention PAAD domain-containing polypeptides can associate with other PAAD domain-containing polypeptides to form invention hetero-oligomers or homo-oligomers, such as heterodimers or homodimers. In particular, the association of the PAAD domain of invention polypeptides with another PAAD domain-containing polypeptide, such as those identified herein, including homo-oligomerization, is sufficiently specific such that the bound complex can form in vivo in a cell or in vitro under suitable conditions. Similarly therefore, an invention PAAD domain-containing polypeptide can associate with another PAAD domain-containing polypeptide by PAAD:PAAD interaction to form invention hetero-oligomers or homo-oligomers, such as heterodimers of homodimers.

In addition to PAAD domains, an invention PAAD domain-containing polypeptide can contain a variety of additional domains including a CARD domain, a NB-ARC domain, a LRR domain, a caspase protease domain, or other recognized domains (see FIG. 3). Accordingly, PAAD domain-containing polypeptides can exhibit one or more of the biological activities characteristic of known CARD domain-, NB-ARC domain-, LRR domain-, or caspase domain-containing polypeptides.

A PAAD domain-containing polypeptide that contains a caspase recruitment domain, or CARD domain (e.g. ASC; FIG. 3), can associate with pro-caspases, caspases or with caspase-associated proteins, thereby altering caspase proteolytic activity.

A PAAD domain-containing polypeptide that contains a caspase protease domain (e.g. zebrafish caspase; FIG. 3) can hydrolyze amide bonds, particularly the amide bond of a peptide or polypeptide backbone. Typically, a caspase protease domain contains a P20/P10 domain in the active site region of the caspase protease domain. Thus, a caspase protease domain has proteolytic activity.

Caspase proteolytic activity is associated with apoptosis of cells, and additionally with cytokine production. As used herein a "caspase" is any member of the cysteine aspartyl proteases. A "pro-caspase" is an inactive or less-active precursor form of a caspase, which is typically converted to the more active caspase form by a proteolytic event, often a preceded by a protein:protein interaction, such as an interaction with a PAAD domain-containing polypeptide.

A PAAD domain-containing polypeptide that contains a NB-ARC domain (such as a PAN, or NAC; FIG. 3) can associate with other polypeptides, particularly with polypeptides comprising NB-ARC domains. Thus, an NB-ARC domain of an invention PAN associates with NB-ARC domain-containing polypeptides by way of NB-ARC:NB-ARC association. Further, a NB-ARC domain demonstrates both nucleotide-binding (e.g., ATP-binding) and hydrolytic activities, which is typically required for its ability to associate with NB-ARC domain-containing polypeptides. Thus, an NB-ARC domain of an invention PAN protein comprises one or more nucleotide binding sites. As used herein, a nucleotide binding site is a portion of a polypeptide that specifically binds a nucleotide such as e.g., ADP, ATP, and the like. Typically, the nucleotide binding site of NB-ARC will comprise a P-loop, a kinase 2 motif, or a kinase 3a motif of the invention PAAD domain-containing polypeptide (these motifs are defined, for example, in van der Biezen and Jones, *Curr. Biol.* 8:R226–R227 (1998)). Preferably, the nucleotide binding site of the NB-ARC of an invention PAN protein comprises a P-loop. The NB-ARC domain of the an invention PAN, therefore, is capable of associating with other NB-ARC domains in homo- or hetero-oligomerization. Additionally, the NB-ARC domain is characterized by nucleotide hydrolysis activity, which can influence the ability of an NB-ARC domain to associate with another NB-ARC domain. In accordance with the present invention, functional fragments of PAN proteins comprising NB-ARC domains are provided.

The amino acid sequences of NB-ARC domains of PAN2, 3, 5 and 6 are set forth as follows: PAN2, SEQ ID NO:37, corresponding to amino acids 147–465 of SEQ ID NO:16; PAN3, SEQ ID NO:60, corresponding to amino acids 196–512 of SEQ ID NO:18;3PAN5, SEQ ID NO:62, corresponding to amino acids 93–273 of SEQ ID NO:22; and PAN6, SEQ ID NO:63, corresponding to amino acids 183–372 of SEQ ID NO:24. The skilled person can readily determine the NB-ARC domain amino acid sequences from other invention PAN polypeptides.

An invention PAAD domain-containing polypeptide, such as a PAN, therefore, is capable of PAAD:PAAD association and/or NB-ARC:NB-ARC association, resulting in a multi-functional polypeptide capable of one or more specific associations with other polypeptides.

As used herein, the term "associate" or "association" refers to binding that is sufficiently specific such that a bound complex can form in vivo in a cell or in vitro under suitable conditions.

A PAAD domain-containing polypeptide can also contain a Leucine-Rich Repeat (LRR) domain (e.g. PAN2, PAN3, PAN6, NAC; see FIG. 3). Leucine-rich repeats (LRRs) are 22–28 amino acid-long leucine rich sequence motifs found in cytoplasmic, membrane and extracellular proteins, including the mammalian Ced4 proteins Nod1 (Inohara et al., *J. Biol. Chem.* 274:14560–14567 (1999)) and DEFCAP, Hlaing et al., *J. Biol. Chem.* 276:9230–9238 (2001), NAC (Chu et al., *J. Biol. Chem.* 276:9239–9245 (2001), and Toll-like receptors (Takeuchi at al., *Gene* 231:59–65 (1999)). The biological activities of LRR domains can include, for example, protein-protein interactions that regulate signal transduction, and cell adhesion; assisting in formation of large, multiprotein complexes; and binding molecules produced by pathogens (e.g. lipids, RNA, proteins, DNA). For example, other LRR-containing proteins are known to bind bacterial lipopolysaccharide (e.g. TLR4 and Nod1/2), CpG DNA (e.g. TLR9), the bacterial protein flagellin (e.g. TLR5), and steroids (e.g. plant LRRs) (see, for example, Fumitaka et al., *Nature* 410:1099–1103 (2001); Aderem et al., *Nature* 406:782–787 (2000); and Beutler, *Immunity* 15;5–14 (2001)). In accordance with the present invention, functional fragments of PAN proteins comprising LRR domains are provided.

The amino acid sequences of the LRR domains of PAN2, 3 and 6 are set forth as follows: PAN2, SEQ ID NO:39, corresponding to amino acids 620–995 of SEQ ID NO:16; PAN3, SEQ ID NO:61, corresponding to amino acids 658 through the C-terminus of SEQ ID NO:18; and PAN6, SEQ ID NO:64, corresponding to amino acids 429–1031 of SEQ ID NO:24. The skilled person can readily determine the LRR domain amino acid sequences from other invention PAN polypeptides.

A PAAD domain-containing polypeptide can also contain an "ANGIO-R" domain. An ANGIO-R domain is a region of a polypeptide chain that bears substantial similarity (e.g. 25, 30, 40% or higher sequence identity) to a portion of the 514-residue long protein "angiotensin II/vasopressin receptor" (described in Ruiz-Opazo et al., *Nature Med.* 1:1074–1081 (1995)).

The amino acid sequence of the ANGIO-R domain PAN2 is set forth as SEQ ID NO:38, corresponding to amino acids 336–605 of SEQ ID NO:16.

An invention PAAD domain-containing polypeptide can alter cell processes such as apoptosis. For example, it is contemplated herein that an invention PAAD domain-containing polypeptide can increase apoptosis in a cell. It is also contemplated herein that an invention PAAD domain-containing polypeptide can decrease the level of apoptosis in a cell. For example, PAAD domain-containing polypeptide which does not induce apoptosis may form hetero-oligomers with a PAAD domain-containing polypeptide which is apoptotic, thus interfering with its apoptosis-inducing activity.

In one embodiment, the invention provides PAAD domain-containing polypeptide comprising substantially the same, or the same, amino acid sequence as set forth in any of SEQ ID NOS:16, 18, 20, 22, 24, 26 and 28, and fragments therefrom, including PAAD, NB-ARC and LRR domain-containing fragments.

As employed herein, the term "substantially the same amino acid sequence" refers to amino acid sequences having at least about 70% or 75% identity with respect to the reference amino acid sequence and retaining comparable functional and biological activity characteristic of the polypeptide defined by the reference amino acid sequence. Preferably, polypeptides having "substantially the same amino acid sequence" will have at least about 80%, 82% 84%, 86% or 88%, more preferably 90%, 91%, 92%, 93% or 94% amino acid identity with respect to the reference amino acid sequence; with greater than about 95%, 96%, 97%, 98% or 99% amino acid sequence identity being especially preferred. It is recognized, however, that polypeptides containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention PAAD domain-containing polypeptide, functional fragments thereof, or chimeric proteins, refers to a polypeptide that exhibits functional characteristics similar to at least a portion of a naturally occurring PAAD domain-containing protein. Biological activities of a naturally occurring PAAD domain-containing protein include, for example, the ability to bind, preferably in vivo, to a nucleotide, to PAAD domain-containing polypeptide, to a CARD-containing polypeptide, to a NB-ARC-containing polypeptide, to a LRR-containing polypeptide or to homo-oligomerize, or to alter protease activation, particularly caspase activation, or to catalyze reactions such as proteolysis or nucleotide hydrolysis, or to alter NF-κB activity, or to alter cJun N-terminal kinase activity, or to alter apoptosis, cytokine processing, cytokine receptor signaling, inflammation, immune response, or other biological activities described herein. Another biological activity of a PAAD domain-containing polypeptide is the ability to act as an immunogen for the production of polyclonal and monoclonal antibodies that bind specifically to an invention PAAD domain-containing polypeptide.

A further biological activity of a PAAD domain-containing polypeptide is the ability to modulate the NFκB transcriptional activity induced by a variety of stimuli, including activators of the TNFα and IL-1β signaling pathways (see Examples). The PAAD domain is sufficiently for this activity.

The ability of a PAAD domain-containing polypeptide to bind another polypeptide such as PAAD-associated polypeptide can be assayed using in vitro or in vivo methods. For example, methods well known in the art such as yeast two-hybrid assays, co-immunoprecipitation, GST fusion co-purification, GST pull-down assays, and other methods provided in standard technique manuals such as Sambrook et al., *Molecular Cloning: A Laboratory Manual*, 2nd ed., Cold Spring Harbor Press, Plainview, N.Y. (1989) and, Ausubel et al., *Current Protocols in Molecular Biology*, John Wiley & Sons, New York (2000) can be used.

As used herein, the term "substantially purified" means a polypeptide that is in a form that is relatively free from contaminating lipids, polypeptides, nucleic acids or other cellular material normally associated with the polypeptide. A substantially purified PAAD domain-containing polypeptide can be obtained by a variety of methods well-known in the art, e.g., recombinant expression systems described herein, precipitation, gel filtration, ion-exchange, reverse-phase and affinity chromatography, and the like. Other well-known methods are described in Deutscher et al., "Guide to Protein Purification" *Methods in Enzymology* Vol. 182, (Academic Press, (1990)). The methods and conditions for biochemical purification of a polypeptide of the invention can be chosen by those skilled in the art, and purification monitored, for example, by an immunological assay, binding assay, or a functional assay.

In addition to the ability of invention PAAD domain-containing polypeptides, or functional fragments thereof, to interact with other, heterologous proteins (e.g. other PAAD domain-, LRR domain- or NB-ARC domain-containing polypeptides), invention PAAD-containing polypeptides have the ability to self-associate to form invention homo-oligomers such as homodimers. This self-association is possible through interactions between PAAD domains, and also through interactions between CARD domains or NB-ARC domains. Further, self-association can take place as a result of interactions between LRR domains.

In accordance with the invention, there are also provided mutations of PAAD domain-containing polypeptides which have activity different than a predominant naturally occurring PAAD domain-containing polypeptide activity. As used herein, "mutation" can be any deletion, insertion, or change of one or more amino acids within the predominant naturally occurring protein sequence (e.g., wild-type), and a "fragment" is any truncated form, either carboxy-terminal, amino-terminal, or both, of the predominant naturally occurring protein. Preferably, the different activity of the mutation or fragment is a result of the mutant polypeptide or fragment maintaining some but not all of the activities of the respective predominant naturally occurring PAAD domain-containing polypeptide.

For example, a functional fragment of an invention protein can contain one or more of the following: a PAAD domain, an NB-ARC domain, a LRR domain or an ANGIO-R domain. In a specific example, a functional fragment of a PAAD domain-containing polypeptide such as a PAN can contain a PAAD domain and LRR domain, but lack a functional NB-ARC domain. Such a fragment will maintain a portion of the predominant naturally occurring PAN activity (e.g., PAAD domain functionality), but not all such activities (e.g., lacking an active NB-ARC domain). The resultant fragment will therefore have an activity different than the predominant naturally occurring PAN activity. In another example, a functional fragment of a PAN protein might have only the NB-ARC domain, allowing it to interact with other NB-ARC domain proteins in forming homo-oligomers or hetero-oligimers. Thus, a functional fragment of a PAAD domain-containing protein or polypeptide is not required to contain a functional PAAD domain, but only to contain a functional domain from a naturally occurring PAAD domain-containing protein. In one embodiment, the activity of the fragment will be "dominant-negative." A dominant-negative activity will allow the fragment to reduce or inactivate the activity of one or more isoforms of a predominant naturally occurring PAAD domain-containing polypeptide.

Methods to identify additional invention PAAD domain-containing polypeptides and functional fragments thereof are well known in the art and are disclosed herein. For example, genomic or cDNA libraries, including universal cDNA libraries can be probed according to methods disclosed herein or other methods known in the art. Full-length polypeptide-encoding nucleic acids such as full-length cDNAs can be obtained by a variety of methods well-known in the art. For example, 5' and 3' RACE, methodology is well known in the art and described in Ausubel et al., supra, and the like.

In another embodiment of the invention, chimeric proteins are provided comprising a PAAD domain-containing polypeptide, or a functional fragment thereof, fused with another protein or functional fragment thereof. Functional fragments of a PAAD domain-containing polypeptide include, for example, NB-ARC, LRR, and ANGIO-R domains or other fragments that retain a biological activity of an invention containing polypeptide. Polypeptides with which the PAAD domain-containing polypeptide or functional fragment thereof are fused can include, for example, glutathione-S-transferase, an antibody, or other proteins or functional fragments thereof which facilitate recovery of the chimera. Further polypeptides with which a PAAD domain-containing polypeptide or functional fragment thereof are fused can include, for example, luciferase, green fluorescent protein, an antibody, or other proteins or functional fragments thereof which facilitate identification of the chimera. Still further polypeptides with which a PAAD domain-containing polypeptide or functional fragment thereof are fused will include, for example, the LexA DNA binding domain, ricin, α-sarcin, an antibody or fragment thereof, or other polypeptides which have therapeutic properties or other biological activity.

Further invention chimeric proteins contemplated herein are chimeric proteins wherein a functional fragment of a PAAD domain-containing polypeptide is fused with a catalytic domain or a protein interaction domain from a heterologous polypeptide. For example, chimeric proteins can contain a functional fragment of a PAAD domain-containing polypeptide of the invention fused with a domain of a protein known in the art, such as CED-4, Apaf-1, caspase-1, and the like. For example, the NB-ARC domain of an invention PAN can be replaced by the NB-ARC domain of CED-4 and the like. Another example of such a chimera is a polypeptide wherein the CARD domain of an invention PAN is replaced by the CARD domain from CED-4, and the like. In a further example, an NB-ARC domain can be fused with a P20/P10 domain to form a novel chimera with caspase activity. In another embodiment, a chimeric protein can be formed which contains functional domains of 2 or more PAAD domain-containing polypeptides of the invention.

As used herein, the term "polypeptide" when used in reference to a PAAD domain-containing polypeptide is intended to refer to a peptide or polypeptide of two or more amino acids. The term "polypeptide analog" includes any polypeptide having an amino acid residue sequence substantially the same as a sequence specifically described herein in which one or more residues have been conservatively substituted with a functionally similar residue and which displays the ability to functionally mimic a PAAD domain-containing polypeptide as described herein. A "modification" of an invention polypeptide also encompasses conservative substitutions of an invention polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu; (4) polar basic amino acids (Lys, Arg and His); and (5) aromatic amino acids (Phe, Trp, Tyr, and His. Other groupings of amino acids can be found, for example in Taylor, *J. Theor. Biol.* 119:205–218 (1986), which is incorporated herein by reference. Other minor modifications are included within invention polypeptides so long as the polypeptide retains some or all of its function as described herein.

The amino acid length of functional fragments of polypeptide analogs of the present invention can range from about 5 amino acids up to the full-length protein sequence of an invention PAAD domain-containing polypeptide. In certain embodiments, the amino acid lengths include, for example, at least about 10 amino acids, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 125, at least about 150, at least about 175, at least about 200, at least about 250 or more amino acids in length up to no more than 1 residue less than a full-length naturally occurring PAAD domain-containing protein. In particular embodiment of the invention, PAAD domain-containing functional fragments comprise an amino acid consensus sequence selected from the group consisting of:

-KFKX$_1$X$_2$L- (SEQ ID NO:29);
-KLKX$_1$X$_2$L- (SEQ ID NO:30);
-RFRX$_1$X$_2$L- (SEQ ID NO:31);
-RFKX$_1$X$_2$L- (SEQ ID NO:32);
-KFRX$_1$X$_2$L- (SEQ ID NO:33); and
-KFKX$_1$X$_2$I- (SEQ ID NO:34);

where X$_1$ and X$_2$ can be any amino acid. Preferably, PAAD domain-containing functional fragments comprise 15 or more contiguous amino acids selected from the group consisting of SEQ ID NOS:1–14.

A modification of a polypeptide can also include derivatives, analogues and functional mimetics thereof, provided that such polypeptide displays a PAAD domain-containing polypeptide biological activity. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptides having one or more additions and/or deletions of residues, relative to the sequence of a polypeptide whose sequence is shown herein, so long as PAAD domain-containing polypeptide activity is maintained.

A modification of an invention polypeptide includes functional mimetics thereof. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide a function of a PAAD domain-containing polypeptide, are included within the meaning of a PAAD domain-containing polypeptide derivative. All of these modifications are included with the term "polypeptide" so long as the invention polypeptide or functional fragment retains its function. Exemplary mimetics are peptidomimetics, peptoids, or other peptide-like polymers such as poly(b- amino acids), and also non-polymeric compounds upon which functional groups that mimic a peptide are positioned.

Another embodiment of the invention provides a PAAD domain-containing polypeptide, or a functional fragment thereof, fused with a moiety to form a conjugate. As used herein, a "moiety" can be a physical, chemical or biological entity which contributes functionality to a PAAD domain-containing polypeptide or a functional fragment thereof. Functionalities contributed by a moiety include therapeutic or other biological activity, or the ability to facilitate identification or recovery of PAAD domain-containing polypeptide. Therefore, a moiety will include molecules known in the art to be useful for detection of the conjugate by, for example, by fluorescence, magnetic imaging, detection of radioactive emission. A moiety may also be useful for recovery of the conjugate, for example a His tag or other known tags used for protein isolation and/or purification, or a physical substance such as a bead. A moiety can be a therapeutic compound, for example, a cytotoxic drug which can be useful to effect a biological charge on cells to which the conjugate localizes.

An example of the methods for preparing the invention polypeptide(s) is to express nucleic acids encoding a PAAD domain-containing polypeptide in a suitable host cell, such as a bacterial cell, a yeast cell, an amphibian cell such as an oocyte, or a mammalian cell, using methods well known in the art, and recovering the expressed polypeptide, again using well-known purification methods. Invention polypeptides can be isolated directly from cells that have been transformed with expression vectors as known in the art. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by in vitro transcription/translation methods known in the art, such as using reticulocyte lysates, as used for example, in the TNT system (Promega). The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

The present invention also provides compositions containing an acceptable carrier and any of an isolated, purified PAAD domain-containing mature protein, such as an invention PAN protein, or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

The invention thus provides a therapeutic composition comprising a pharmaceutically acceptable carrier and a compound selected from the group consisting of a PAAD domain-containing fragment polypeptide, a PAAD domain-containing chimeric protein, a PAAD domain-containing polypeptide modulating compound, and an anti-PAAD antibody. The invention additionally provides a method of treating a pathologies characterized by abnormal cell proliferation, abnormal cell death, or inflammation by administering an effective amount of the composition containing a pharmaceutically acceptable carrier and a compound selected from the group consisting of a PAAD domain-containing polypeptide, a functional fragment thereof, a PAAD domain-containing polypeptide modulating compound, and an anti-PAAD antibody.

PAAD domain-containing polypeptide can be administered to an individual to increase an activity associated with a PAAD domain-containing polypeptide, including induction of apoptosis, functioning as a tumor suppressor, modulation of inflammation or cell adhesion, and the like. For example, PAAD domain-containing polypeptide can be administered therapeutically to an individual using expression vectors containing nucleic acids encoding PAAD domain-containing polypeptides, as described below. In addition, PAAD domain-containing polypeptide, or a functional portion thereof, can be directly administered to an individual. Methods of administering therapeutic polypeptides are well known to those skilled in the art, for example, in the form or a pharmaceutical composition.

In accordance with another embodiment of the invention, there are provided isolated nucleic acids encoding a PAAD domain-containing polypeptide fragment or chimeric protein comprising a PAAD domain-containing polypeptide. The isolated nucleic acids can be selected from:
(a) DNA encoding a polypeptide containing the amino acid sequence set forth in SEQ ID NOs: 16, 18, 20, 22, 24, 26 or 28, or
(b) DNA that hybridizes to the DNA of (a) under moderately stringent conditions, where the DNA encodes a biologically active PAAD domain-containing polypeptide.

The nucleic acid molecules described herein are useful for producing invention polypeptides, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention PAAD domain encoding gene or mRNA transcript in a given sample. The nucleic acid molecules described herein, and fragments thereof, are also useful as primers and/or templates in a PCR reaction for amplifying genes encoding invention polypeptides described herein.

The term "nucleic acid" or "nucleic acid molecule" (also referred to as polynucleotides) encompasses ribonucleic acid (RNA) or deoxyribonucleic acid (DNA), probes, oligonucleotides, and primers and can be single stranded or double stranded. DNA can be either complementary DNA (cDNA) or genomic DNA, e.g. a PAAD domain encoding gene, and can represent the sense strand, the anti-sense strand, or both. Examples of nucleic acids are RNA, cDNA, or isolated genomic DNA encoding a PAAD domain-containing polypeptide. One means of isolating a PAAD domain encoding nucleic acid polypeptide is to probe a mammalian genomic or cDNA library with a natural or artificially designed DNA probe using methods well known in the art. DNA probes derived from the PAAD domain encoding gene are particularly useful for this purpose. DNA and cDNA molecules that encode PAAD domain-containing polypeptide can be used to obtain complementary genomic DNA, cDNA or RNA from mammalian (e.g., human, mouse, rat, rabbit, pig, and the like), or other animal sources, or to isolate related cDNA or genomic clones by screening cDNA or genomic libraries, using methods described in more detail below.

In one embodiment, invention nucleic acids comprise substantially the same or the same nucleotide sequence as set forth in SEQ ID NOs:15 (PAN2), 17 (PAN3), 19 (PAN4), 21 (PAN5), 23 (PAN6), 25 (pyrin2), or 27 (ASC2).

Thus a PAAD domain encoding nucleic acid as used herein refers to a nucleic acid encoding a polypeptide containing a PAAD domain-containing polypeptide fragment of the invention, or a PAAD domain-containing chimeric protein.

Use of the terms "isolated" and/or "purified" and/or "substantially purified" in the present specification and claims as a modifier of DNA, RNA, polypeptides or proteins means that the DNA, RNA, polypeptides or proteins so designated have been produced in such form by the hand of man, and thus are separated from their native in vivo cellular environment, and are substantially free of any other species of nucleic acid or protein. As a result of this human intervention, the recombinant DNAs, RNAs, polypeptides and proteins of the invention are useful in ways described herein that the DNAs, RNAs, polypeptides or proteins as they naturally occur are not.

Invention nucleic acids encoding PAAD domain-containing polypeptides and invention PAAD domain-containing polypeptides can be obtained from any species of organism, such as prokaryotes, eukaryotes, plants, fungi, vertebrates, invertebrates, and the like. A particular species can be mammalian, e.g., human, rat, mouse, rabbit, monkey, baboon, bovine, porcine, ovine, canine, feline, and the like. A preferred PAAD domain encoding nucleic acid herein, is human PAAD domain encoding nucleic acid.

As employed herein, the term "substantially the same nucleotide sequence" refers to DNA having sufficient identity to the reference polynucleotide, such that it will hybridize to the reference nucleotide under moderately or highly stringent hybridization conditions. In one embodiment, DNA having substantially the same nucleotide sequence as the reference nucleotide sequence encodes substantially the same amino acid sequence as that set forth in any of SEQ ID NOs:16, 18, 20, 22, 24, 26 or 28. In another embodiment, DNA having "substantially the same nucleotide sequence" as the reference nucleotide sequence has at least 60%, or at least 65% identity with respect to the reference nucleotide sequence. DNA having at least 70%, 72%, 74%, 76%, 78%, 80%, 82%, 84%, 86% or 88%, more preferably at least 90%, 91%, 92%, 93% or 94% yet more preferably at least 95%, 96%, 97%, 98% or 99% identity to the reference nucleotide sequence is preferred.

As used herein, a "modification" of a nucleic acid can also include one or several nucleotide additions, deletions, or substitutions with respect to a reference sequence. A modification of a nucleic acid can include substitutions that do not change the encoded amino acid sequence due to the degeneracy or the genetic code. Such modifications can correspond to variations that are made deliberately, or which occur as mutations during nucleic acid replication.

Exemplary modifications of the recited nucleotide sequences include sequences that correspond to homologs of other species, including mammalian species such as mouse, primates, including monkey and baboon, rat, rabbit, bovine, porcine, ovine, canine, feline, or other animal species. The corresponding nucleotide sequences of non-human species can be determined by methods know in the art, such as by PCR or by screening genomic, cDNA or expression libraries.

Another exemplary modification of the invention PAAD domain encoding nucleic acid or PAAD domain-containing polypeptide can correspond to mutant or splice variant forms of the PAAD domain encoding nucleotide sequence.

Additionally, a modification of a nucleotide sequence can include one or more non-native nucleotides, having, for example, modifications to the base, the sugar, or the phosphate portion, or having a modified phosphodiester linkage. Such modifications can be advantageous in increasingly the stability of the nucleic acid molecule.

Furthermore, a modification of a nucleotide sequence can include, for example, a detectable moiety, such as a radiolabel, a fluorochrome, a ferromagnetic substance, a luminescent tag or a detectable binding agent such as biotin. Such modifications can be advantageous in applications where detection of a PAAD domain encoding nucleic acid molecule is desired.

This invention also encompasses nucleic acids which differ from the nucleic acids shown in SEQ ID NOs:15, 17, 19, 21, 23, 25 and 27, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same polypeptide product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding invention PAAD domain-containing polypeptides that, by virtue of the degeneracy of the genetic code, do not necessarily hybridize to the invention nucleic acids under specified hybridization conditions. Preferred nucleic acids encoding the invention PAAD domain-containing polypeptides are comprised of nucleotides that encode substantially the same amino acid sequence as set forth in SEQ ID NOs:16, 18, 20, 22, 24, 26 or 28.

hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature (Tm) of the hybrids. In general, the stability of a hybrid is a function of sodium ion concentration and temperature. Typically, the hybridization reaction is performed under conditions or lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, at least about 75% identity, more at least about 85% identity; or at least about 90% identity.

Moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C.

The phrase "high stringency hybridization " refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., supra (1989); and Ausubel et al., supra (2000).

Nucleic acids encoding polypeptides hybridize under moderately stringent or high stringency conditions to substantially the entire sequence, or substantial portions, for example, typically at least 15, 17, 21, 25, 30, 40, 50 or more nucleotides of the nucleic acid sequence set forth in SEQ ID NOs:15, 17, 19, 21, 23, 25 or 27.

As used herein, the term "degenerate" refers to codons that differ in at least one nucleotide from a reference nucleic acid, e.g., SEQ ID NOs:15, 17, 19, 21, 23, 25 and 27 but encode the same amino acids as the reference nucleic acid. For example, codons specified by the triplets "UCU", "UCC", "UCA", and "UCG" are degenerate with respect to each other since all four of these codons encode the amino acid serine.

The invention also provides a modification of a nucleotide sequence that hybridizes to a PAAD domain encoding nucleic acid molecule, for example, a nucleic acid molecule referenced as SEQ ID NOs:15, 17, 19, 21, 23, 25 or 27, under moderately stringent conditions. Modifications of nucleotide sequences, where the modification has at least 60% identity to PAAD domain encoding nucleotide sequence, are also provided. The invention also provides modification of a PAAD domain encoding nucleotide sequence having at least 65% identity, at least 70% identity, at least 72% identity, at least 74% identity, at least 76% identity, at least 78% identity, at least 80% identity, at least 82% identity, at least 84% identity, at least 86% identity, at least 88% identity, at least 90% identity, at least 91% identity, at least 92% identity, at least 93% identity, at least 94% identity, at least 95% identity, at least 96% identity, at least 97% identity, at least 98% identity or at least 99% identity.

Identity of any two nucleic acid or amino acid sequences can be determined by those skilled in the art based, for example, on known computer alignments such as BLAST 2.0, ClustalW and the like, which can be adjusted manually, if appropriate, to insert gaps to optimize the alignment according to standard practice in the art.

One means of isolating a nucleic acid encoding a PAAD domain-containing polypeptide is to probe a cDNA library or genomic library with a natural or artificially designed nucleic acid probe using methods well known in the art. Nucleic acid probes derived from a PAAD domain encoding gene are particularly useful for this purpose. DNA and cDNA molecules that encode PAAD domain-containing polypeptides can be used to obtain complementary genomic DNA, cDNA or RNA from mammals, for example, human, mouse, rat, rabbit, pig, and the like, or other animal sources, or to isolate related cDNA or genomic clones by the screening of cDNA or genomic libraries, by methods well known in the art (see, for example, Sambrook et al., supra (1989); Ausubel et al., supra (2000)).

The invention additionally provides a nucleic acid that hybridizes under high stringency conditions to the PAAD domain coding portion of any of SEQ ID NOs:15, 17, 19, 21, 23, 25 or 27. The invention also provides a nucleic acid having a nucleotide sequence substantially the same as set that forth in any of SEQ ID NOs:15, 17, 19, 21, 23, 25 or 27.

The invention also provides a method for identifying nucleic acids encoding a mammalian PAAD domain-containing polypeptide by contacting a sample containing nucleic acids with one or more invention oligonucleotides, wherein the contacting is effected under high stringency hybridization conditions, and identifying a nucleic acid that hybridizes to the oligonucleotide. The invention additionally provides a method of detecting a PAAD domain encoding nucleic acid molecule in a sample by contacting the sample with two or more invention oligonucleotides, amplifying a nucleic acid molecule, and detecting the amplification. The amplification can be performed, for example, using PCR. The invention further provides oligonucleotides that function as single stranded nucleic acid primers for amplification of a PAAD domain encoding nucleic acid, wherein the primers comprise a nucleic acid sequence derived from the nucleic acid sequences set forth as SEQ ID NOS:SEQ ID NOs:15, 17, 19, 21, 23, 25 or 27.

In accordance with a further embodiment of the present invention, optionally labeled PAAD-encoding cDNAs, or fragments thereof, can be employed to probe library(ies) such as cDNA, genomic, BAC, and the like for predominant nucleic acid sequences or additional nucleic acid sequences encoding novel PAAD domain-containing polypeptides. Construction and screening of suitable mammalian cDNA libraries, including human cDNA libraries, is well-known in the art, as demonstrated, for example, in Ausubel et al., supra. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Hybridization conditions are selected which allow the identification of sequences having at least 70% homology with the probe, while discriminating against sequences which have a lower degree of homology with the probe. As a result, nucleic acids having substantially the same nucleotide sequence as SEQ ID NOs:15, 17, 19, 21, 23, 25 or 27, are obtained.

As used herein, a nucleic acid "probe" is single-stranded nucleic acid, or analog thereof, that has a sequence or nucleotides that includes at least 15, at least at least 17, at least 20, at least 22, at least 25, at least 30, at least 40, at least 50, at least 75, at least 100, at least 200, at least 300, at least 400, or at least 500 contiguous bases that are substantially the same as, or the complement of, any contiguous bases set forth in any of SEQ ID NOs:15, 17, 19, 21, 23, 25 or 27.

Preferred regions from which to construct probes include 5' and/or 3' coding regions of SEQ ID NOs:15, 17, 19, 21, 23, 25 or 27. In addition, the entire cDNA encoding region of an invention PAAD domain-containing polypeptide, or an entire sequence substantially the same as SEQ ID NOs:15, 17, 19, 21, 23, 25 or 27, may be used as a probe. Probes can be labeled by methods well-known in the art, as described hereinafter, and used in various diagnostic kits.

The invention additionally provides an oligonucleotide comprising at least 15 contiguous nucleotides of SEQ ID NOs:15, 17, 19, 21, 23, 25 or 27, or the anti-sense strand thereof. As used herein, the term "oligonucleotide" refers to a nucleic acid molecule that includes at least 15 contiguous nucleotides from a reference nucleotide sequence, can include at least 16, 17, 18, 19, 20 21, 22, or at least 25 contiguous nucleotides, and often includes at least 30, 40, 50, 60, 70, 80, 90, 100, 125, 150, 175, 200, 225, 250, 275, 300, 325, 350, 400, 500, 600, 700 or more contiguous nucleotides from the reference nucleotide sequence. The reference nucleotide sequence can be the sense strand or the anti-sense strand.

The oligonucleotides of the invention that contain at least 15 contiguous nucleotides of a reference PAAD domain encoding nucleotide sequence are able to hybridize to PAAD domain encoding nucleotide sequences under moderately stringent hybridization conditions and thus can be advantageously used, for example, as probes to detect PAAD domain encoding DNA or RNA in a sample, and to detect splice variants thereof; as sequencing or PCR primers; as antisense reagents to block transcription of PAAD domain encoding RNA in cells; or in other applications known to those skilled in the art in which hybridization to a PAAD domain encoding nucleic acid molecule is desirable.

In accordance with another embodiment of the invention, a method is provided for identifying nucleic acids encoding a PAAD-domain-containing polypeptide, comprising:

contacting a sample containing nucleic acids with an invention probe or an invention oligonucleotide, wherein said contacting is effected under high stringency hybridization conditions, and identifying nucleic acids which hybridize thereto. Methods for identification of nucleic acids encoding a PAAD domain-containing polypeptide are disclosed herein.

Also provided in accordance with present invention is a method for identifying a PAAD domain encoding nucleotide sequence comprising the steps of using a PAAD domain encoding nucleotide sequence selected from SEQ ID NOS:15, 17, 19, 21, 23, 25 or 27, to identify a candidate PAAD domain encoding nucleotide sequence and verifying the candidate PAAD domain encoding nucleotide sequence by aligning the candidate sequence with known PAAD domain encoding nucleotide sequences, where a conserved PAAD domain sequence or a predicted three dimensional polypeptide structure similar to known PAAD domain three dimensional structure confirms the candidate sequence as a PAAD domain encoding sequence. Methods for identifying PAAD-encoding sequences are provided herein (See Examples 1.0, 2.0, 3.0 and 4.0).

It is understood that a PAAD domain encoding nucleic acid molecule of the invention, as used herein, specifically excludes previously known nucleic acid molecules consisting of nucleotide sequences having exact sequence identity with the PAAD domain encoding nucleotide sequence (SEQ ID NOS:15, 17, 19, 21, 23, 25 or 27), such as Expressed Sequence Tags (ESTs), Sequence Tagged Sites (STSs) and genomic fragments, deposited in public databases such as the nr, dbest, dbsts, gss and htgs databases, which are available for searching at http://www.ncbi.nlm.nih.gov/blast/.

In particular, invention PAAD domain encoding nucleic acid molecules, and PAAD domain-containing polypeptide, excludes the exact, specific and complete nucleic acid and/or amino acid sequences corresponding to any of the nucleotide and/or amino acid sequences having the Genbank (gb), NCBI, EMBL (emb) OR DDBJ (dbj) accession numbers described below. Accession numbers specifically excluded include NCBI Accession Nos: GI 4557743, 5094556, 7019331, 7689912, 7020664, 7382417, 2335202, 7690109, 8099799, 8655944, 7662386, 5902751, 2833279, 6523868, 3483677, 10440263, 14731965, 2335202, 15488764, 202805, 9211204, 3483677, 15488878, 14779455, 14779445, 14488058, 11096298, 9802275, 9863861, 9863863, 10835255, 10801601, 7020146, 14779447, 13325315, 15215377, 11230601, 9937751, 14758026, 15193291, 13182796, 14731965, 14731967, 4757727, 3341995, 10440263, 14253110, 9153913, and 1383656.

Since one of skill in the art will realize that the above-recited excluded sequences may be revised at a later date, the skilled artisan will recognize that the above-recited sequences are excluded as they stand on the priority date of this application.

The isolated nucleic acid molecules of the invention can be used in a variety of diagnostic and therapeutic applications. For example, the isolated nucleic acid molecules of the invention can be used as probes, as described above; as templates for the recombinant expression of PAAD domain-containing polypeptide; or in screening assays such as two-hybrid assays to identify cellular molecules that bind PAAD domain-containing polypeptide.

Another useful method for producing a PAAD domain encoding nucleic acid molecule of the invention involves amplification of the nucleic acid molecule using PCR and invention oligonucleotides and, optionally, purification of the resulting product by gel electrophoresis. Either PCR or RT-PCR can be used to produce a PAAD domain encoding nucleic acid molecule having any desired nucleotide boundaries. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention thus provides methods for detecting a PAAD domain encoding nucleic acid in a sample. The methods of detecting a PAAD domain encoding nucleic acid in a sample can be either qualitative or quantitative, as desired. For example, the presence, abundance, integrity or structure of a PAAD domain encoding nucleic acid can be determined, as desired, depending on the assay format and the probe used for hybridization or primer pair chosen for application.

Useful assays for detecting a PAAD domain-containing nucleic acid based on specific hybridization with an isolated invention oligonucleotide are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A hybridization probe can be labeled with any suitable detectable moiety, such as a radioisotope, fluorochrome, chemiluminescent marker, biotin, or other detectable moiety known in the art that is detectable by analytical methods.

Useful assays for detecting PAAD domain encoding nucleic acid in a sample based on amplifying a PAAD domain encoding nucleic acid with two or more invention oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified PAAD domain encoding nucleic acid can be sequenced to detect mutations and mutational hot-spots, and specific assays for large-scale screening of samples to identify such mutations can be developed.

In a particular embodiment, a PAAD domain-containing polypeptide, or functional fragment thereof, can be administered to an individual so that the PAAD domain-containing polypeptide or functional fragment is targeted to a tumor to induce apoptosis, inhibit cell proliferation, or otherwise function as a tumor suppressor. One method or delivering PAAD domain-containing polypeptide to an intracellular target is to fuse a PAAD domain-containing polypeptide or functional fragment to an intracellular-targeting peptide that can penetrate the cell membrane or otherwise deliver a polypeptide to the intracellular environment such as via internalization, thereby causing the fused PAAD domain-containing polypeptide to enter the cell. One example of such an intracellular-targeting peptides is a fusion to the transduction domain of HIV TAT, which allows transduction of up to 100% of cells (Schwarze et al., *Science* 285:1569–1572 (1999); Vocero-Akbani et al., *Nature Med.* 5:29–33 (1999)).

Another example of such an intracellular-targeting peptide is the Antennapeida homeoprotein internalization domain (Holinger et al., *J. Biol. Chem.* 274:13298–13304 (1999)). Still another intracellular-targeting peptide is a peptide that is specific for a cell surface receptor, which allows binding and internalization of a fusion polypeptide via receptor-mediated endocytosis (Ellerby et al., *Nature Med.* 5:1032–1038 (1999)). Such intracellular-targeting peptides that mediate specific receptor interactions can be advantageously used to target a tumor (see Ellerby et al., supra, 1999). Alternatively, a PAAD domain-containing polypeptide of the invention can be incorporated, if desired, into Liposomes, microspheres or other polymer matrices (Gregoriadis, *Lioosome Technology,* Vols. I to III, 2nd ed., CRC Press, Boca Raton, Fla. (1993)).

Also provided are antisense-nucleic acids having a sequence capable of binding specifically with full-length of any portion of an mRNA that encodes PAAD domain-containing polypeptides so as to prevent translation of the mRNA. The antisense-nucleic acid can have a sequence capable of binding specifically with any portion of the sequence of the cDNA encoding PAAD domain-containing polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

Also provided are double-stranded RNA molecules for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end (Elbashir et al., *Nature* 411:494–498 (2001); Bass, *Nature* 411:428–429 (2001); Zamore *Nat. Struct. Biol.* 8:746–750 (2001)). dsRNAs of about 25–30 nucleotides have also been used successfully for RNAi (Karabinos et al., *Proc. Natl. Acad. Sci.* 98:7863–7868 (2001). dsRNA can be synthesized in vitro and introduced into a cell by methods known in the art. By such methods, translation of the target polypeptide can be decreased.

The present invention provides a method of reducing levels of expression of PAAD domain-containing polypeptides by introducing into a cell anti-sense nucleic acids that inhibit translation or degrade mRNA encoding these polypeptides. Such nucleic acid molecules are designed to recognize and selectively bind to mRNA, such as to mRNA comprising SEQ ID NOs:15, 17, 19, 21, 23, 25 or 27, and are complementary to portions thereof.

The present invention also provides a method of reducing levels of expression of PAAD domain-containing polypeptide by introducing into a cell dsRNA that degrades mRNA encoding such polypeptides. Such dsRNA contains short contiguous sequences or about 21–30 nucleotides or SEQ ID NOs:15, 17, 19, 21, 23, 25 or 27, and about 21–30 nucleotides complementary thereto, designed such that there is about a 2 base overhang at each 3' end of the double-stranded sequence.

Compositions comprising an amount or the antisense-nucleic acid or dsRNA effective to reduce expression or PAAD domain-containing polypeptides can further contain an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. For example, the structure can be part of a protein known to bind to a cell-type specific receptor.

The invention also provides a method for expression of a PAAD domain-containing polypeptide by culturing cells containing a PAAD domain encoding nucleic acid under conditions suitable for expression of a PAAD domain-containing polypeptide. Thus, there is provided a method for the recombinant production of a PAAD domain-containing polypeptide of the invention by expressing the PAAD domain encoding nucleic acid sequences in suitable host cells. Recombinant DNA expression systems that are suitable to produce a PAAD domain-containing polypeptide described herein are well-known in the art (see, for example, Ausubel et al., supra (2000)). For example, the above-described nucleotide sequences can be incorporated into vectors for further manipulation. As used herein, a vector refers to a recombinant DNA or RNA plasmid or virus containing discrete elements that are used to introduce heterologous DNA into cells for either expression or replication thereof.

The invention also provides vectors containing the PAAD domain encoding nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra (2000)). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors or the invention are useful for subcloning and amplifying a PAAD domain encoding nucleic acid molecule and for recombinantly expressing a PAAD domain-containing polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing PAAD domain encoding nucleic acids of the invention. The recombinant cells are generated by introducing into a host cell a vector containing a PAAD domain encoding nucleic acid molecule. The recombinant cells are transducted, transfected or otherwise genetically modified. Exemplary host cells that can be used to express recombinant PAAD molecules include mammalian primary cells; established mammalian cell lines, such as COS, CHO, HeLa, NIH3T3, HEK 293 and PC12 cells; amphibian cells, such as Xenopus embryos and oocytes and other vertebrate cells. Exemplary host cells also include insect cells such as Drosophila, yeast cells such as Saccharomyces cerevisiae, Saccharomyces pombe, or Pichia pastoris, and prokaryotic cells such as Escherichia coli. Additional host cells can be obtained, for example from ATCC (Manassas, Va.)

In one embodiment, PAAD domain encoding nucleic acids can be delivered into mammalian cells, either in vivo or in vitro using suitable vectors well-known in the art. Suitable vectors for delivering a PAAD domain-containing polypeptide, or a functional fragment thereof to a mammalian cell, include viral vectors such as retroviral vectors, adenovirus, adeno-associated virus, lentivirus, herpesvirus, as well as non-viral vectors such as plasmid vectors. Such vectors are useful for providing therapeutic amounts of a PAAD domain-containing polypeptide (see, for example, U.S. Pat. No. 5,399,346, issued Mar. 21, 1995). Delivery or PAAD polypeptides or nucleic acids therapeutically can be particularly useful when targeted to a tumor cell, thereby inducing apoptosis in tumor cells. In addition, where it is desirable to limit or reduce the in vivo expression of a PAAD domain-containing polypeptide, the introduction of the antisense strand of the invention nucleic acid is contemplated.

The invention additionally provides an isolated anti-PAAD domain antibody (also referred to herein as an anti-PAAD antibody) having specific reactivity with a invention PAAD domain-containing polypeptide. The anti-PAAD antibody can be a monoclonal antibody or a polyclonal antibody. The invention further provides cell lines producing monoclonal antibodies having specific reactivity with an invention PAAD domain-containing protien.

The invention thus provides antibodies that specifically bind a PAAD domain-containing polypeptide. As used herein, the term "antibody" is used in its broadest sense to include polyclonal and monoclonal antibodies, as well as antigen binding fragments of such antibodies. With regard to an anti-PAAD antibody of the invention, the term "antigen" means a native or synthesized PAAD domain-containing polypeptide or fragment thereof. An anti-PAAD antibody, or antigen binding fragment of such an antibody, is characterized by having specific binding activity for a PAAD polypeptide or a peptide portion thereof of at least about $1 \times 10^5$ $M^{-1}$. Thus, Fab, F(ab')$_2$, Fd and Fv fragments of an anti-PAAD antibody, which retain specific binding activity for a PAAD domain-containing polypeptide, are included within the definition of an antibody. Specific binding activity of a PAAD domain-containing polypeptide can be readily determined by one skilled in the art, for example, by comparing the binding activity of an anti-PAAD antibody to a PAAD domain-containing polypeptide versus a reference polypeptide that is not a PAAD domain-containing polypeptide. Methods of preparing polyclonal or monoclonal antibodies are well known to those skill in the art (see, for example, Harlow and Lane, *Antibodies: A Laboratory Manual,* Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting or variable heavy chains and variable light chains as described by Huse et al., *Science* 246:1275–1281 (1989)). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, supra, 1988); Hilyard et al., *Protein Engineering: A practical approach* (IRL Press 1992); Borrabeck, *Antibody Engineering,* 2d ed. (Oxford University Press 1995)).

Anti-PAAD antibodies can be raised using a PAAD immunogen such as isolated PAAD domain-containing functional fragment comprising an amino acid consensus sequence selected from the group consisting of:

-KFKX$_1$X$_2$L- (SEQ ID NO:29);
-KLKX$_1$X$_2$L- (SEQ ID NO:30);
-RFRX$_1$X$_2$L- (SEQ ID NO:31);
-RFKX$_1$X$_2$L- (SEQ ID NO:32);
-KFRX$_1$X$_2$L- (SEQ ID NO:33); and
-KFKX$_1$X$_2$I- (SEQ ID NO:34);

where X$_1$ and X$_2$ can be any amino acid; or PAAD domain-containing protein having substantially the same amino acid sequence as SEQ ID NOS:16, 18, 20, 22, 24, 26 or 28, or a portion thereof, which can be prepared from natural sources or produced recombinantly. Such a portion of a PAAD domain-containing polypeptide is a functional antigen portion if the antigenic peptides can be used to generate a PAAD domain-containing polypeptide-specific antibody.

The invention further provides a method for detecting the presence of a human PAAD domain-containing polypeptide in a sample by contacting a sample with a PAAD domain specific antibody, and detecting the presence of specific binding of the antibody to the sample, thereby detecting the presence of a human PAAD domain-containing polypeptide in the sample. PAAD domain specific antibodies can be used in diagnostic methods and systems to detect the level of PAAD domain-containing polypeptide present in a sample. As used herein, the term "sample" is intended to mean any biological fluid, cell, tissue, organ or portion thereof, that includes or potentially includes PAAD domain encoding nucleic acids or PAAD domain-containing polypeptides. The term includes samples present in an individual as well as samples obtained or derived from the individual. For example, a sample can be a histologic section or a specimen obtained by biopsy, or cells that are placed in or adapted to tissue culture. A sample further can be a subcellular fraction or extract, or a crude or substantially pure nucleic acid or polypeptide preparation.

PAAD domain specific antibodies can also be used for the immunoaffinity or affinity chromatography purification of an invention PAAD domain-containing polypeptide. In addition, methods are contemplated herein for detecting the presence of an invention PAAD domain-containing polypeptide in a cell, comprising contracting the cell with an antibody that specifically binds to PAAD domain-containing polypeptides under conditions permitting binding of the antibody to the PAAD domain-containing polypeptides, detecting the presence of the antibody bound to the PAAD domain-containing polypeptide, and thereby detecting the presence of invention polypeptides in a cell. With respect to the detection or such polypeptides, the antibodies can be used for in vitro diagnostic or in vivo imaging methods.

Immunological procedures useful for in vitro detection of target PAAD domain-containing polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra (1988); Harlow and Lane, *Using Antibodies: A Laboratory Manual,* Cold Spring Harbor Press (1999)).

An antibody can be made detectable by various means well known in the art. For example, a detectable marker can be directly attached to the antibody or indirectly attached using, for example, a secondary agent that recognizes the PAAD specific antibody. Useful markers include, for example, radionucleotides, enzymes, binding proteins such as blotin, fluorogens, chromogens, fluorescent labels and chemiluminescent labels. A description of immunofluorescent analytic techniques is found in DeLuca, "Immunofluorescence Analysis", in *Antibody As a Tool,* Marchalonis et al., eds., John Wiley & Sons, Ltd., pp. 189–231 (1982), which is incorporated herein by reference.

In addition to detecting the presence of a PAAD domain-containing polypeptide, invention anti-PAAD antibodies are contemplated for use herein to alter the activity of the PAAD domain-containing polypeptide in living animals, in humans, or in biological tissues or fluids isolated therefrom. The term "alter" refers to the ability of a compound such as a PAAD domain-containing polypeptide, a PAAD domain encoding nucleic acid, an agent or other compound to increase or decrease biological activity which is modulated by the compound, by functioning as an agonist or antagonist of the compound. Accordingly, compositions comprising a carrier and an amount of an antibody having specificity for PAAD domain-containing polypeptides effective to block naturally occurring ligands or other PAAD-associated polypeptides from binding to invention PAAD domain-containing polypeptides are contemplated herein. For example, a monoclonal antibody directed to an epitope of an invention PAAD domain-containing polypeptide, including an amino acid sequence substantially the same as SEQ ID NOS:16, 18, 20, 22, 24, 26 or 28, can be useful for this purpose.

The present invention further provides transgenic non-human mammals that are capable of expressing exogenous nucleic acids encoding PAAD domain-containing polypeptides. As employed herein, the phrase "exogenous nucleic acid" refers to nucleic acid sequence which is not native to the host, or which is present in the host in other than its native environment, for example, as part of a genetically engineered DNA construct. In addition to naturally occurring PAAD domain-containing polypeptide levels, a PAAD domain-containing polypeptide of the invention can either be overexpressed or underexpressed in transgenic mammals, for example, underexpressed in a knock-out animal.

Animal model systems useful for elucidating the physiological and behavioral roles of PAAD domain-containing polypeptides are also provided, and are produced by creating transgenic animals in which the expression of the PAAD domain-containing polypeptide is altered using a variety of techniques. Examples of such techniques include the insertion of normal or mutant versions of nucleic acids encoding a PAAD domain-containing polypeptide by microinjection, retroviral infection or other means well known to those skilled in the art, into appropriate fertilized embryos to produce a transgenic animal, see, for example, Hogan et al., *Manipulating the Mouse Embryo: A Laboratory Manual* (Cold Spring Harbor Laboratory, (1986)). Transgenic animal model systems are useful for in vivo screening of compounds for identification of specific ligands, such as agonists or antagonists, which activate or inhibit a biological activity.

In accordance with another embodiment of the invention, a method is provided for identifying PAAD-associated polypeptide (PAP). The method is carried out by contacting an invention PAAD domain-containing polypeptide with a candidate PAP and detecting association of the PAAD domain-containing polypeptide with the PAP.

As used herein, the term "PAAD-associated polypeptide" or "PAP" means a polypeptide that can specifically bind to the PAAD domain-containing polypeptides of the invention, or to any functional fragment of a PAAD domain-containing polypeptides of the invention. Because PAAD domain-containing polypeptides of the invention contain domains which can self-associate, PAAD domain-containing polypeptides are encompassed by the term PAP. An exemplary PAP is a protein or a polypeptide portion of a protein that can bind a PAAD, NB-ARC, LRR or ANGIO-R domain of an invention PAAD domain-containing polypeptide. A PAP can be identified, for example, using in vitro or in vivo protein-interaction assays and methods known in the art, including yeast two-hybrid assays, co-immunoprecipitation, GST fusion co-purification, GST pull-down assays and the like (see, for example, Ausubel et al., supra (2000)). Additional methods include, for example, scintillation proximity assay (SPA) (Alouani, Methods Mol. Biol. 138:135–41 (2000)), UV or chemical cross-linking (Fancy, *Curr. Opin. Chem: Biol.* 4:28–33 (2000)), competition binding assays (Yamamura et al., *Methods in Neurotransmitter Receptor*

*Analysis,* Raven Press, New York, 1990), biomolecular interaction analysis (BIA) such as surface plasmon resonance (SPR) (Weinberger et al., *Pharmacogenomics* 1:395–416 (2000)), mass spectrometry (MS) (McLafferty et al., *Science* 284:1289–1290 (1999) and Degterev, at al., *Nature Cell Biology* 3:173–182 (2001)), nuclear magnetic resonance (NMR) (Shuker etal., *Science* 274:1531–1534 (1996), Hajduk et al., *J. Med. Chem.* 42:2315–2317 (1999), and Chen and Shapiro, *Anal Chem.* 71:669A–675A (1999)), and fluorescence polarization assays (FPA) (Degterev et al., supra, 2001).

Exemplary PAPs contemplated herein can include a protein involved in regulating apoptosis, caspase activation or NFκB induction, and other PAAD domain-containing polypeptides, selected from Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP kinase, NIK, IKKα, IKKβ, IκB, p65, p50, IKAP, pyrin, pyrin2, PAN1, PAN2, PAN3, PAN4, PAN5, PAN6, ASC, ASC2, NAC, AIM2, IFI16, MO13L, p52, p100, p105, ParaCaspase (MALT1) and all members of the NFκB/IκB families. The naturally occurring sequences of these molecules from a variety of species, including human and rodent, are well known in the art. The skilled person can readily determine fragments and modifications of naturally occurring PAP sequences that retain their ability to associate with a PAAD domain-containing polypeptide, or domain therefrom, in the assays described herein.

As disclosed herein, exemplary PAPs that associate with ASC include ASC, ASC2, Caspase-1, Card10, Nod1, Cardiak, NIK and IKK-i. An exemplary PAP that associates with PAN2 is IκBα. An exemplary PAP that associates with PAN6 is IKAP.

The normal association between a PAAD domain-containing polypeptide and a PAP polypeptide in a cell can be altered due, for example, to the expression in the cell of variant PAP or PAAD domain-containing polypeptide, respectively, either of which can compete with the normal binding function of a PAAD domain-containing polypeptide and, therefore, can decrease the association of PAP and PAAD domain-containing polypeptides in a cell. The term "varient" is used generally herein to mean a polypeptide that is different from the PAP or PAAD domain-containing polypeptide that normally is found in a particular cell type. Thus, a variant can include a mutated protein or a naturally occurring protein, such as an isoform, that is not normally found in a particular cell type.

PAAD domain-containing polypeptides and PAAD-associated polypeptides of the invention can be characterized, for example, using in vitro binding assays or the yeast two hybrid system. An in vivo transcription activation assay such as the yeast two hybrid system is particularly useful for identifying and manipulating the association of proteins. In addition, the results observed in such an assay likely mirror the events that naturally occur in a cell. Thus, the results obtained in such an in vivo assay can be predictive of results that can occur in a cell in a subject such as a human subject.

A transcription activation assay such as the yeast two hybrid system is based on the modular nature of transcription factors, which consist of functionally separable DNA-binding and trans-activation domains. When expressed as separate proteins, these two domains fail to mediate gene transcription. However, transcription activation activity can be restored if the DNA-binding domain and the trans-activation domain are bridged together due, for example, to the association of two proteins. The DNA-binding domain and trans-activation domain can be bridged, for example, by expressing the DNA-binding domain and trans-activation domain as fusion proteins (hybrids), provided that the proteins that are fused to the domains can associate with each other. The non-covalent bridging of the two hybrids brings the DNA-binding and trans-activation domains together and creates a transcriptionally competent complex. The association of the proteins is determined by observing transcriptional activation of a reporter gene.

The yeast two hybrid systems exemplified herein use various strains of *S. cerevisiae* as host cells for vectors that express the hybrid proteins. A transcription activation assay also can be performed using, for example, mammalian cells. However, the yeast two hybrid system is particularly useful due to the ease or working with yeast and the speed with which the assay can be performed. For example, yeast host cells containing a lacZ reporter gene linked to a LexA operator sequence can be used to demonstrate that a PAAD domain of an invention PAAD domain-containing polypeptide can interact with itself or other PAAD domain-containing polypeptides. For example, the DNA-binding domain can consist of the LexA DNA-binding domain, which binds the LexA promoter, fused to the PAAD domain of a PAAD domain-containing polypeptide of the invention and the trans-activation domain can consist of the B42 acidic region separately fused to several cDNA sequences which encode known PAAD domain-containing polypeptides. When the LexA domain is non-covalently bridged to a trans-activation domain fused to a PAAD domain-containing polypeptide, the association can activate transcription of the reporter gene.

A PAP, for example, a PAAD domain-containing polypeptide, a CARD-containing polypeptide, an NB-ARC-containing polypeptide or a LRR-containing polypeptide, also can be identified using well known in vitro assays, for example, an assay utilizing a glutathione-S-transferase (GST) fusion protein. Such an in vitro assay provides a simple, rapid and inexpensive method for identifying and isolating a PAP. Such an in vitro assay is particularly useful in confirming results obtained in vivo and can be used to characterize specific binding domains of a PAP. For example, a GST can be fused to a PAAD domain-containing polypeptide of the invention, and expressed and purified by binding to an affinity matrix containing immobilized glutathione. If desired, a sample that can contain a PAP or active fragments of a PAP can be passed over an affinity column containing bound GST/PAAD and a PAP that binds to a PAAD domain-containing polypeptide can be obtained. In addition, GST/PAAD can be used to screen a cDNA expression library, wherein binding of the GST/PAAD fusion protein to a clone indicates that the clone contains a cDNA encoding a PAP.

Thus, one of skill in the art will recognize that using the PAAD domain-containing polypeptides described herein, a variety of methods, such as protein purification, protein interaction cloning, or protein mass-spectrometry, can be used to identify, a PAP.

Although the term "PAP" is used generally, it should be recognized that a PAP that is identified using the novel polypeptide described herein can be a fragment of a protein. Thus, as used herein, a PAP also includes a polypeptide that specifically associates to a portion of an invention PAAD domain-containing polypeptide that does not include a PAAD domain. For example, a PAP can associate with the NB-ARC domain of an invention PAN. As used herein, a "candidate PAP" refers to a polypeptide containing a polypeptide sequence know or suspected of binding one or more PAAD domain-containing polypeptides of the invention. Thus, a PAP can represent a full-length protein or a PAAD-associating fragment thereof. Since a PAP polypeptide can be a full-length protein or a PAAD-associating fragment thereof, one of skill in the art will recognize that a PAP-encoding nucleic acid, such as the genomic sequence, an mRNA sequence or a cDNA sequence need not encode the full-length protein. Thus, a cDNA can encode a polypeptide that is a fragment of a full-length PAP which, nevertheless, binds one or more invention PAAD domain-containing polypeptides. It is also within the scope of the invention that a full-length PAP can assume a conformation that does not, absent some post-translational modification, bind a PAAD domain-containing polypeptide of the invention, due, for example, to steric blocking of the binding site. Thus, a PAP can be a protein or a polypeptide portion of a protein that can bind one of the PAAD domain-containing polypeptides of the invention. Also, it should be recognized that a PAP can be identified by using a minimal polypeptide derived from the sequences of the PAAD domain-containing polypeptides of the invention, and does not necessarily require that the full-length molecules be employed for identifying such PAPs.

Since PAAD domain-containing polypeptides can be involved in apoptosis, the association of a PAP with a PAAD domain-containing polypeptide can affect the sensitivity of resistance of a cell to apoptosis or can induce or block apoptosis induced by external or internal stimuli. The identification of various PAPs by use of known methods can be used to determine the function of these PAPs in cell death or signal transduction pathways controlled by PAAD domain-containing polypeptides, allowing for the development of assays that are useful for identifying agents that effectively alter the association of a PAP with a PAAD domain-containing polypeptide. Such agents can be useful for providing effective therapy for conditions caused, at least in part, by insufficient apoptosis, such as cancer, autoimmune disease or certain viral infections. Such agents can also be useful for providing an effective therapy for diseases where excessive apoptosis is known to occur, such as stroke, heart failure, or AIDS; as well as inflammatory diseases, such as inflammatory bowel diseases (e.g. Crohn's disease and ulcerative colitus); rheumatoid arthritis, sepsis, trauma, allograft rejection and graft-versus-host disease.

Since PAAD domain-containing polypeptides are also involved in regulating NFκB activity, the association of a PAP with a PAAD domain-containing polypeptide can also affect responses of cells to stimuli that activate NFκB transcription, including TNFα and IL-1 and other proinflammatory cytokines, T- and B-cell mitogens, bacteria, bacterial lipopolysaccharide (LPS), viruses, viral proteins, double stranded RNA, and physical and chemical stresses. The identification of various PAPs as described herein and agents that effectively alter the association of a PAP with a PAAD domain-containing polypeptide can be used to provide effective therapy for conditions mediated, at least in part, by NFκB, including, for example, inflammatory conditions, infections, cancers, neurodegenerative disorders, arthritis and asthma.

Assays of the invention can be used for identification of agents that alter the self-association of the PAAD domain-containing polypeptides of the invention. Thus, the methods of the invention can be used to identify agents that alter the self-association of invention PAAD domains, such as SEQ ID NOS:1–14 and PAAD domain-containing proteins, such as SEQ ID NOs:16, 18, 20, 22, 24, 26 and 28, via their PAAD domains, NB-ARC domains, LRR domains, ANGIO-R domains or other domains within these polypeptides.

The ATP-binding and hydrolysis of the NB-ARC domains can be critical for function of a PAAD domain-containing polypeptide, for example, by altering the oligomerization of the PAAD domain-containing polypeptide. Thus, agents that interfere with or enhance ATP or nucleotide binding and/or hydrolysis by the NB-ARC domain of a PAAD domain-containing polypeptide of the invention, such as invention PAN proteins, can also be useful for altering the activity of these polypeptides in cells.

A further embodiment of the invention provides a method to identify agents that can effectively alter PAAD domain-containing polypeptide activity, for example the ability of PAAD domain-containing polypeptides to associate with one or more heterologous proteins. Thus, the present invention provides a screening assay useful for identifying an effective agent, which can alter the association of a PAAD domain-containing polypeptide, such as a PAN, with a PAAD-associated polypeptide (PAP), such as a heterologous PAAD domain-containing polypeptide.

Effective agents can be useful to alter a biochemical process modulated by a PAAD domain-containing polypeptide of the invention. Additional biochemical processes (also referred to herein as "cell activities") example, apoptosis, regulation of NFκB induction, cytokine processing, cytokine receptor signaling, cJUN N-terminal kinase induction, caspase-mediated proteolytic activation/inhibition, transcription, inflammation and cell adhesion.

As used herein, the term "agent" means a chemical or biological molecule such as a simple or complex organic molecule, a peptide, a peptido-mimetic, a polypeptide, a protein or an oligonucleotide that has the potential for altering the association of a PAAD domain-containing polypeptide with a heterologous protein or altering the ability of a PAAD domain-containing polypeptide to self-associate or altering the ligand binding or biological activity of a PAAD domain-containing polypeptide. An exemplary ligand binding activity is nucleotide binding activity, such as ADP or ATP binding activity; and exemplary catalytic activities are nucleotide hydrolytic activity and proteolytic activity. In addition, the term "effective agent" is used herein to mean an agent that is confirmed as capable of altering the association of a PAAD domain-containing polypeptide with a heterologous protein or altering the ability of a PAAD domain-containing polypeptide to self-associate or altering the ligand binding or catalytic activity of a PAAD domain-containing polypeptide. For example, an effective agent may be an anti-PAAD antibody, a PAAD-associated polypeptide and the like.

As used herein, the term "alter the association" means that the association between two specifically interacting polypeptides either is increased or decreased due to the presence of an effective agent. As a result of an altered association of PAAD domain-containing polypeptide with another polypeptide in a cell, the activity of the PAAD domain-containing polypeptide or the PAP can be increased or decreased, thereby altering a biochemical process, for example, the level of apoptosis or NFκB transcriptional activity in the cell. As used herein, the term "alter the activity" means that the agent can increase or decrease the activity of a PAAD domain-containing polypeptide in a cell, thereby modulating a biochemical process in a cell, for example, the level or apoptosis or NFκB transcriptional activity in the cell. Similarly, the term "alter the level" of a biological process modulated by a PAAD domain-containing polypeptide refers to an increase or decrease a biochemical process which occurs upon altering the activity of a PAAD domain-containing polypeptide. For example, an effective agent can increase or decrease the PAAD:PAAD-associating activity of a PAAD domain-containing polypeptide, which can result in altered apoptosis or increased or decreased NFκB transcriptional activity. In another example, alteration of the ATP hydrolysis activity can modulate the ability of the NB-ARC domain of a PAAD domain-containing polypeptide to associate with other NB-ARC-containing polypeptides, such as Apaf-1, thereby altering any process effected by such association between a PAAD domain-containing polypeptide and an NB-ARC-containing polypeptide.

An effective agent can act by interfering with the ability of a PAAD domain-containing polypeptide to associate with another polypeptide, or can act by causing the dissociation of a PAAD domain-containing polypeptide from a complex with a PAAD-associated polypeptide, wherein the ratio of bound PAAD domain-containing polypeptide to free PAAD domain-containing polypeptide is related to the level of a biochemical process, such as apoptosis or NFκB transcriptional activity, in a cell. For example, binding of a ligand to a PAP can allow the PAP, in turn, to bind a specific PAAD domain-containing polypeptide such that all of the specific PAAD domain-containing polypeptide is bound to a PAP.

An effective agent can be useful, for example, to increase the level of apoptosis in a cell such as a cancer cell, which is characterized by having a decreased level of apoptosis as compared to its normal cell counterpart. An effective agent also can be useful, for example, to decrease the level of apoptosis in a cell such as a T lymphocyte in a subject having a viral disease such as acquired immunodeficiency syndrome, which is characterized by an increased level of apoptosis in an infected T cell as compared to a normal T cell. Thus, an effective agent can be useful as a medicament for altering the level of apoptosis in a subject having a pathology characterized by increased or decreased apoptosis in addition, an effective agent can be used, for example, to decrease the level of apoptosis and, therefore, increase the survival time of a cell such as a hybridoma cell in culture. The use of an effective agent to prolong the survival of a cell in vitro can significantly improve bioproduction yields in industrial tissue culture applications.

An effective agent can also be useful to increase or decrease NFκB transcriptional activity, and thus can be used to provide effective therapy for conditions mediated, at least in part, by NFκB, including for example, inflammatory conditions (e.g. inflammatory bowel diseases, such as Crohn's disease and ulcerative colitus), infections, cancers, neurodegenerative disorders, arthritis, asthma, stroke, heart failure, AIDS, sepsis, trauma, allograft rejection and graft-versus-host disease.

A PAAD domain-containing polypeptide that lacks the ability to bind the CARD domain, NB-ARC domain or LRR domain of another polypeptide but retains the ability to self-associate via its PAAD domain or to bind to other PAAD domain-containing polypeptides is an example of an effective agent, since the expression of a non-NB-ARC-associating or non-catalytically active PAAD domain-containing polypeptide in a cell can alter the association of a the endogenous PAAD domain-containing polypeptide with itself or with PAPs.

Thus, it should be recognized that a mutation of a PAAD domain-containing polypeptide can be an effective agent, depending, for example, on the normal levels of PAAD domain-containing polypeptide and PAAD-associated polypeptide that occur in a particular cell type. In addition, an active fragment of a PAAD domain-containing polypeptide can be an effective agent, provided the active fragment can alter the association of a PAAD domain-containing polypeptide and another polypeptide in a cell. Such active fragments, which can be peptides as small as about five amino acids, can be identified, for example, by screening a peptide library (see, for example, Ladner et al., U.S. Pat. No.: 5,223,409, which is incorporated herein by reference) to identify peptides that can bind a PAAD-associated polypeptide.

Similarly, a peptide or polypeptide portion of a PAAD-associated polypeptide also can be an effective agent. A peptide of PAAD-associated polypeptide can be useful, for example, for decreasing the association of a PAAD domain-containing polypeptide with a PAP in a cell by competing for binding to the PAAD domain-containing polypeptide. A non-naturally occurring peptido-mimetic also can be useful as an effective agent. Such a peptido-mimetic can include, for example, a peptoid, which is peptide-like sequence containing N-substituted glycines, or an oligocarbamate. A peptido-mimetic can be particularly useful as an effective agent due, for example, to having an increased stability to enzymatic degradation in vivo.

In accordance with another embodiment of the present invention, there is provided a method of identifying an effective agent that alters the association of an invention PAAD domain-containing polypeptide with a PAAD-associated polypeptide (PAP), by the steps of:

contacting the PAAD domain-containing polypeptide and PAP polypeptides, under conditions that allow the PAAD domain-containing polypeptide and PAP polypeptides to associate, with an agent suspected of being able to alter the association of the PAAD domain-containing polypeptide and PAP polypeptides; and (b) detecting the altered association of the PAAD domain-containing polypeptide and PAP polypeptides, where the altered association identifies an effective agent.

Methods well-known in the art for detecting the altered association of the PAAD domain-containing polypeptide and PAP polypeptides, for example, measuring protein:protein binding, protein degradation or apoptotic activity can be employed in bioassays described herein to identify agents as agonists or antagonists of PAAD domain-containing polypeptides. As described herein, PAAD domain-containing polypeptides have the ability to self-associate. Thus, methods for identifying effective agents that alter the association of a PAAD domain-containing polypeptide with a PAP are useful for identifying effective agents that alter the ability of a PAAD domain-containing polypeptide to self-associate.

As used herein, "conditions that allow said PAAD domain-containing polypeptide and PAP polypeptides to associate" refers to environmental conditions in which a PAAD domain-containing polypeptide and PAP specifically associate. Such conditions will typically be aqueous conditions, with pH between 3.0 and 11.0, and temperature below 100° C. Preferably, the conditions will be aqueous conditions with salt concentrations below the equivalent of 1 M NaCl, and pH between 5.0 and 9.0, and temperatures between 0° C. and 50° C. Most preferably, the conditions will range from physiological conditions of normal yeast or mammalian cells, or conditions favorable for carrying out in vitro assays such as immunoprecipitation and GST protein: protein association assays, and the like.

In another embodiment of the invention, a method is provided for identifying agents that modulate a biological activity of an invention PAAD domain-containing polypeptide, such as ligand interaction or catalytic activity. The method contains the steps of contacting an invention PAAD domain-containing polypeptide with an agent suspected of modulating a ligand binding or biological activity of the PAAD domain-containing polypeptide and measuring a biological activity of the PAAD domain-containing polypeptide, where modulated biological activity identifies the agent as an agent that alters the biological activity of a PAAD domain-containing polypeptide.

As used herein in regard to biological activity, "modulate" refers to an increase or decrease in the measured biological activity. Thus, modulation encompasses inhibition of biological activity as well as activation or enhancement of biological activity. Exemplary biological activities include nucleotide binding, nucleotide hydrolysis and modulation of NFκB activation.

Methods for measuring ligand binding and other biological activities are well known in the art, as disclosed herein. For example, an agent known or suspected of modulating a biological activity can be contacted with an invention PAAD domain-containing polypeptide in vivo or in vitro, and the activity can be measured using know methods. Exemplary agents that can modulate a biological activity include peptides, peptidomimetics and other peptide analogs, non-peptide organic molecules such as naturally occurring protease inhibitors and derivatives thereof, nucleotides and nucleotide analogs, and the like. Such inhibitors can be either reversible or irreversible, as is well known in the art.

Agents that modulate a biological activity of a PAAD domain-containing polypeptide identified using the invention methods can be used to modulate the activity of a PAAD domain-containing polypeptide. For example, an agent can modulate the nucleotide binding or nucleotide hydrolytic activity of an NB-ARC domain of a PAAD domain-containing polypeptide. In another example, an agent can modulate the NFκB regulatory activity of the PAAD domain. Methods of modulating a biological activity of invention PAAD domain-containing proteins can be used in methods of altering biochemical processes modulated by PAAD domain-containing proteins, such as the biochemical processes disclosed herein.

In yet another embodiment of the present invention, there are provided methods for altering a biological activity of a PAAD domain-containing polypeptide of the invention, the method comprising:

contacting an PAAD domain-containing polypeptide With an effective amount of an agent identified by the herein-described bioassays.

The present invention also provides in vitro screening assays. Such screening assays are particularly useful in that they can be automated, which allows for high through-put screening, for example, of randomly or rationally designed agents such as drugs, peptidomimetics or peptides in order to identify those agents that effectively alter the association of a PAAD domain-containing polypeptide and a PAP or the catalytic or ligand binding activity of a PAAD domain-containing polypeptide and, thereby, alter a biochemical process modulated by a PAAD domain-containing polypeptide such as apoptosis. An in vitro screening assay can utilize, for example, a PAAD domain-containing polypeptide including a PAAD domain-containing fusion protein such as a PAAD-glutathione-S-transferase fusion protein.

For use in the in vitro screening assay, the PAAD domain-containing polypeptide should have an affinity or a solid substrate as well as the ability to associate with a PAAD-associated polypeptide. For example, when a PAAD domain-containing polypeptide is used in the assay, the solid substrate can contain a covalently attached anti-PAAD antibody.

Alternatively, a GST/PAAD fusion protein can be used in the assay and the solid substrate can contain covalently attached glutathione, which is bound by the GST component of the GST/PAAD fusion protein. Similarly, a PAAD-associated polypeptide can be used in any of a variety of in vitro enzymatic or in vitro binding assays known in the art and described in texts such as Ausubel et al., supra, 2000.

An in vitro screening assay can be performed by allowing a PAAD domain-containing polypeptide or fragment thereof to bind to the solid support, then adding PAAD-associated polypeptide and an agent to be tested. Reference reactions, which do not contain an agent, can be performed in parallel. Following incubation under suitable conditions, which include, for example, an appropriate buffer concentration and pH and time and temperature that permit binding of the particular PAAD domain-containing polypeptide and PAAD-associated polypeptide, the amount of protein that has associated in the absence of an agent and in the presence of an agent can be determined. The association of a PAAD-associated polypeptide, with a PAAD domain-containing polypeptide can be detected, for example, by attaching a detectable moiety such as a radionuclide or a fluorescent label to a PAAD-associated polypeptide and measuring the amount of label that is associated with the solid support, wherein the amount of label detected indicates the amount of association of the PAAD-associated polypeptide with a PAAD domain-containing polypeptide. An effective agent is determined by comparing the amount of specific binding in the presence of an agent as compared to a reference level of binding, wherein an effective agent alters the association of PAAD domain-containing polypeptide with the PAAD-associated polypeptide. Such an assay is particularly useful for screening a panel of agents such as a peptide library in order to detect an effective agent.

Additionally, a PAAD domain-containing polypeptide or domain thereof, such as a PAAD domain or NB-ARC domain, can be contacted with a candidate agent and association between the polypeptide and the candidate agent determined. Agents that bind in such assays can further be tested for their ability to alter a biological activity of a PAAD domain-containing polypeptide or for their ability to alter associations between a PAAD domain-containing polypeptide and a PAP.

Various binding assays described above, such as the two hybrid assay, co-immunoprecipitation assay, co-localization assay, scintillation proximity assay (SPA), UV or chemical cross-linking, biomolecular interaction analysis (BIA), mass spectrometry (MS), nuclear magnetic resonance (NMR), and fluorescence polarization assays (FPA) can be used to identify an effective agent.

Another assay for screening of agents that alter the activity of a PAAD domain-containing polypeptide is based on altering the phenotype of yeast by expressing a PAAD domain-containing polypeptide. In one embodiment, expression of a PAAD domain-containing polypeptide can be inducible (Tao et al., J. Biol. Chem. 273:23704–23708 (1998), and the compounds can be screened when PAAD domain-containing polypeptide expression is induced. PAAD domain-containing polypeptides of the invention can also be co-expressed in yeast with PAP polypeptides used to screen for compounds that antagonize the activity of the PAAD domain-containing polypeptide.

A biological activity that can potentially be altered by an agent is PAAD domain-mediated modulation of NFκB activity. An agent that increases or decreases PAAD domain-mediated inhibition of NFκB activity with correspondingly decrease or increase NFκB activity. Such agents can be useful for treating conditions associated with decreased or increased NFκB activity as described herein, including, for example, inflammation, autoimmune diseases, neurodegenerative diseases, cancer and infectious disorders.

The invention thus provides methods of identifying agents that modulate PAAD domain-mediated inhibition or stimulation of NFκB activity. In one embodiment, a cell that recombinantly expresses a PAAD domain-containing polypeptide is contacted with a candidate agent and altered NFκB activity, such as increased or decreased activity, is detected in the cell. As NFκB activity in an unstimulated cell is normally low, such methods can be practiced by contacting the cell with an NFκB inducer, such as TNFα or IL1β, or recombinantly expressing within the cell an NFκB inducer, such as Bcl10, TRAF2, TRAF6, NIK, RIP2, p65, IRAK2, IRAK3, MyD88, RIP, IL-1R, Nod1, IKKα, IKKβ, TNFR1, and the like, such that the PAAD domain-containing polypeptide inhibits the induced level of NFκB activity.

The skilled person can employ appropriate controls to confirm that the effect of the candidate agent is specific for the PAAD domain-containing polypeptide. For example, the effect on NFκB activation of the candidate agent can be compared to the effect in a control cell that does not express nucleic acid molecule encoding a PAAD domain-containing polypeptide. Additionally, the effect of the candidate agent on NFκB activation can be compared with the effect of a vehicle control not containing the agent.

Various methods of determining the amount of NFκB activity in a cell are well known in the art. For example, binding assays have been developed that take advantage of the observation that active NFκB, but not inactive NFκB, binds to DNA. Therefore, the binding of a test cell extract to a labeled oligonucleotide containing an NFκB consensus binding site can be assayed. Active NFκB in the cell extract is evidenced by retardation of the mobility of the oligonucleotide band on a gel (Schreck et al, *Nucleic Acids Res.* 18:6497–6502 (1990); Rusher et al., *J. Biotech.* 78:163–170 (2000)). An alternative method is to attach an oligonucleotide containing a NFκB consensus binding site to a multiwell plate and detect bound, active NFκB in an ELISA-type assay using NFκB antibodies (Renard et al., *Nucleic Acids Res.* 29:E21 (2001)).

An alternative assay for determining the amount of NFκB activity in a cell monitors the cleavage of the NFκB precursors p100 or p105 to the active p50 or p55 subunits (see, for example, Lin et al., *Mol. Cell. Biol.* 16:2248–2254 (1996); Morgan et al., *Cancer Res.* 59:6205–6213 (1999); Uren et al., *Mol. Cell* 6:961–967 (2000)).

Activity assays can also be used to determine the amount of NFκB activity in a cell. For example, a reporter gene such as the luciferase, β-galactosidase or secretory alkaline phosphatase gene can be placed under the control of a promoter containing the NFκB consensus site. NFκB activity in cells transfected with the reporter construct is evidenced by expression of the product of the reporter gene (Moon et al., *Anal. Biochem.* 292:17–21 (2001); see Examples).

Additional methods of monitoring NFκB activation include, for example, monitoring cytoplasmic IκB degradation using antibodies directed against IκB (Sun et al., *Proc. Natl. Acad. Sci. USA* 91:1346–1350 (1994), and monitoring exposure of the nuclear localization signal (NLS) of active NFκB using NLS-specific antibodies (Zabel et al., *EMBO J.* 12:201–211 (1993)).

Also provided with the present invention are assays to identify agents that alter PAAD domain-containing polypeptide expression. Methods to determine PAAD domain-containing polypeptide expression can involve detecting a change in PAAD domain-containing polypeptide abundance in response to contacting the cell with an agent that modulates PAAD domain-containing polypeptide expression. Assays for detecting changes in polypeptide expression include, for example, immunoassays with PAAD domain specific antibodies, such as immunoblotting, immunofluorescence, immunohistochemistry and immunoprecipitation assays, as described herein.

As understood by those of skill in the art, assay methods for identifying agents that alter PAAD domain-containing polypeptide activity generally require comparison to a reference. One type of a "reference" is a cell or culture that is treated substantially the same as the test cell or test culture exposed to the agent, with the distinction that the "reference" cell or culture is not exposed to the agent. Another type of "reference" cell or culture can be a cell or culture that is identical to the test cells, with the exception that the "reference" cells or culture do not express a PAAD domain-containing polypeptide. Accordingly, the response of the transfected cell to an agent is compared to the response, or lack thereof, of the "reference" cell or culture to the same agent under the same reaction conditions.

Methods for producing pluralities or agents to use in screening for compounds that alter the activity of a PAAD domain-containing polypeptide, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.,* 2:363–371 (1998); Sofia, *Mol. Divers.* 3:75–94 (1998); Eichler et al., *Med. Res. Rev.* 15:481–496 (1995); and the like. Libraries containing large numbers of natural and synthetic agents also can be obtained from commercial sources. Combinatorial libraries of molecules can be prepared using well known combinatorial chemistry methods (Gordon et al., *J. Med. Chem.* 37:1233–1251 (1994); Gordon et al., *J. Med. Chem.* 37:1385–1401 (1994); Gordon et al., *Acc. Chem. Res.* 29:144–154 (1996); Wilson and Czarnik, eds., *Combinatorial Chemistry: Synthesis and Application,* John Wiley & Sons, New York (1997)).

The invention further provides a method of diagnosing or predicting clinical prognosis of a pathology characterized by an increased or decreased level or a PAAD domain-containing polypeptide in a subject. The method includes the steps of (a) obtaining a test sample from the subject; (b) contacting the sample with an agent that can bind a PAAD domain-containing polypeptide of the invention under suitable conditions, wherein the conditions allow specific binding of the agent to the PAAD domain-containing polypeptide; and (c) comparing the amount of the specific binding in the test sample with the amount or specific binding in a reference sample, wherein an increased or decreased amount of the specific binding in the test sample as compared to the reference sample is diagnostic of, or predictive of the clinical prognosis of, a pathology. The agent can be, for example, an anti-PAAD antibody, a PAAD-associated-polypeptide (PAP), or a PAAD domain encoding nucleic acid.

Exemplary pathologies for diagnosis or the prediction or clinical prognosis include any of the pathologies described herein, such as neoplastic pathologies (e.g. cancer), autoimmune diseases, and other pathologies related to abnormal cell proliferation or abnormal cell death (e.g. apoptosis), as disclosed herein.

The invention also provides a method of diagnosing cancer or monitoring cancer therapy by contacting a test sample from a patient with a PAAD domain specific antibody. The invention additionally provides a method of assessing prognosis (e.g., predicting the clinical prognosis) of patients with cancer comprising contacting a test sample from a patient with a PAAD domain specific antibody.

The invention additionally provides a method of diagnosing cancer or monitoring cancer therapy by contacting a test sample from a patient with a oligonucleotide that selectively hybridizes to a PAAD domain encoding nucleic acid molecule. The invention further provides a method of assessing prognosis (e.g., predicting the clinical prognosis) of patients with cancer by contacting a test sample from a patient with a oligonucleotide that selectively hybridizes to a PAAD domain encoding nucleic acid molecule.

The methods of the invention for diagnosing cancer or monitoring cancer therapy using a PAAD domain specific antibody or oligonucleotide or nucleic acid that selectively hybridizes to a PAAD domain encoding nucleic acid molecule can be used, for example, to segregate patients into a high risk group or a low risk group for diagnosing cancer or predicting risk of metastasis or risk of failure to respond to therapy. Therefore, the methods of the invention can be advantageously used to determine, for example, the risk of metastasis in a cancer patient, or the risk of an autoimmune disease of a patient, or as a prognostic indicator of survival or disease progression in a cancer patient or patient with an autoimmune disease. One of ordinary skill in the art would appreciate that the prognostic indicators of survival for cancer patients suffering from stage I cancer can be different from those for cancer patients suffering from stage IV cancer. For example, prognosis for stage I cancer patients can be oriented toward the likelihood of continued growth and/or metastasis of the cancer, whereas prognosis for stage IV cancer patients can be oriented toward the likely effectiveness of therapeutic methods for treating the cancer. Accordingly, the methods of the invention directed to measuring the level of or determining the presence of a PAAD domain-containing polypeptide or PAAD domain encoding nucleic acid can be used advantageously as a prognostic indicator for the presence or progression of a cancer or response to therapy.

The invention further provides methods for introducing a PAAD domain encoding nucleic acid into a cell in a subject, for example, for gene therapy. Viruses are specialized infectious agents that can elude host defense mechanisms and can infect and propagate in specific cell types. Viral based systems provide the advantage of being able to introduce relatively high levels of the heterologous nucleic acid into a variety of cells. Suitable viral vectors for introducing an invention PAAD domain encoding nucleic acid into mammalian cells (e.g., vascular tissue segments) are well known in the art.

The present invention also provides therapeutic compositions useful for practicing the therapeutic methods described herein. Therapeutic compositions of the present invention, such as pharmaceutical compositions, contain a physiologically compatible carrier together with an invention PAAD domain-containing polypeptide (or functional fragment thereof), an invention PAAD domain encoding nucleic acid, an agent that alters PAAD activity or expression identified by the methods described herein, or an anti-PAAD antibody, as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically compatible" and grammatical variations thereof, as they refer to compositions, carriers, diluents and reagents, are used interchangeably and represent that the materials are capable or administration to a mammal without the production of undesirable physiological effects such as nausea, dizziness, gastric upset, and the like.

The preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient in amounts suitable for use in the therapeutic methods described herein. Suitable excipients are, for example, water, saline, dextrose, glycerol, ethanol, or the like, as well as combinations of any two or more thereof. In addition, if desired, the composition can contain minor amounts of auxiliary substances such as wetting or emulsifying agents, pH buffering agents, and the like, which enhance the effectiveness of the active ingredient.

Physiologically tolerable carriers are well known in the art. Exemplary liquid carriers are sterile aqueous solutions that contain no materials in addition to the active ingredients and water, or contain a buffer such as sodium phosphate at physiological pH, physiological saline or both, such as phosphate-buffered saline. Still further, aqueous carriers can contain more than one buffer salt, as well as salts such as sodium and potassium chlorides, dextrose, polyethylene glycol and other solutes.

As described herein, an "effective amount" is a predetermined amount calculated to achieve the desired therapeutic effect, i.e., to alter the protein binding activity of a PAAD domain-containing polypeptide or the catalytic activity of PAAD domain-containing polypeptide, resulting in altered biochemical process modulated by a PAAD domain-containing polypeptide. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such agents in depot or long-lasting form as discussed herein. A therapeutically effective amount is typically an amount of an agent identified herein that, when administered in a physiologically acceptable composition, is sufficient to achieve a plasma concentration of from about 0.1 $\mu$g/ml to about 100 $\mu$g/ml, preferably from about 1.0 $\mu$g/ml to about 50 $\mu$g/ml, more preferably at least about 2 $\mu$g/ml and usually 5 to 10 $\mu$g/ml. Therapeutic invention anti-PAAD antibodies can be administered in proportionately appropriate amounts in accordance with known practices in this art.

Also provided herein are methods of treating pathologies characterized by abnormal cell proliferation, abnormal cell death, or inflammation said method comprising administering an effective amount of an invention therapeutic composition. Such compositions are typically administered in a physiologically compatible composition.

Exemplary abnormal cell proliferation diseases associated with PAAD domain-containing polypeptides contemplated herein for treatment according to the present invention include cancer pathologies, keratinocyte hyperplasia, neoplasia, keloid, benign prostatic hypertrophy, inflammatory hyperplasia, fibrosis, smooth muscle cell proliferation in arteries following balloon angioplasty (restenosis), and the like. Exemplary cancer pathologies contemplated herein for treatment include, gliomas, carcinomas, adenocarcinomas, sarcomas, melanomas, hamartomas, leukemias, lymphomas, and the like. Further diseases associated with PAAD domain-containing polypeptides contemplated herein for treatment according to the present invention include inflammatory diseases and diseases of cell loss. Such diseases include allergies, inflammatory diseases including arthritis, lupus, Schrogen's syndrome, Crohn's disease, ulcerative colitis, as well as allograft rejection, such as graft-versus-host disease, and the like. PAAD domain-containing polypeptides can also be useful in design of strategies for preventing diseases related to abnormal cell death in conditions such as stroke, myopyrinial infarction, heart failure, neurodegenerative diseases such as Parkinson's and Alzheimer's diseases, and for immunodeficiency associated diseases such as HIV infection, HIV-related disease, and the like.

Methods of treating pathologies can include methods or modulating the activity of one or more oncogenic proteins, wherein the oncogenic proteins specifically interact with a PAAD domain-containing polypeptide of the invention. Methods of modulating the activity of such oncogenic proteins will include contacting the oncogenic protein with a substantially pure PAAD domain-containing polypeptide or an active fragment (i.e., oncogenic protein-binding fragment) thereof. This contacting will alter the activity of the oncogenic protein, thereby providing a method of treating a pathology caused by the oncogenic protein. Further methods of modulating the activity of oncogenic proteins will include contacting the oncogenic protein with an agent, wherein the agent alters interaction between a PAAD domain-containing polypeptide and an oncogenic protein.

Also contemplated herein, are therapeutic methods using invention pharmaceutical compositions for the treatment of pathological disorders in which there is too little cell division, such as, for example, bone marrow aplasias, immunodeficiencies due to a decreased number of lymphocytes, and the like. Methods of treating a variety of inflammatory diseases with invention therapeutic compositions are also contemplated herein, such as treatment of sepsis, fibrosis (e.g., scarring), arthritis, graft versus host disease, and the like.

The present invention also provides methods for diagnosing a pathology that is characterized by an increased or decreased level of a biochemical process to determine whether the increased or decreased level of the biochemical process is due, for example, to increased or decreased expression of a PAAD domain-containing polypeptide or to expression of a variant PAAD domain-containing polypeptide. As disclosed herein, such biochemical processes include apoptosis, NFκB induction, cytokine processing, caspase-mediated proteolysis, transcription, inflammation, cell adhesion, and the like. The identification of such a pathology, which can be due to altered association of a PAAD domain-containing polypeptide with a PAAD-associated polypeptide in a cell, or altered ligand binding or catalytic activity of a PAAD domain-containing polypeptide, can allow for intervention therapy using an effective agent or a nucleic acid molecule or an antisense or dsRNA nucleotide sequence as described herein. In general, a test sample can be obtained from a subject having a pathology characterized by having or suspected of having increased or decreased apoptosis and can be compared to a reference sample from a normal subject to determine whether a cell in the test sample has, for example, increased or decreased expression of a PAAD domain encoding gene. The level of a PAAD domain-containing polypeptide in a cell can be determined by contacting a sample with a reagent such as an anti-PAAD antibody or a PAAD-associated polypeptide, either of which can specifically bind a PAAD domain-containing polypeptide. For example, the level of a PAAD domain-containing polypeptide in a cell can determined by well known immunoassay or immunohistochemical methods using an anti-PAAD antibody (see, for example, Peed and Godzik et al., Anal. Biochem. 205:70–76 (1992); see, also, Harlow and Lane, supra, (1988)). As used herein, the term "reagent" means a chemical or biological molecule that can specifically bind to a PAAD domain-containing polypeptide or to a bound PAAD/PAAD-associated polypeptide complex. For example, either an anti-PAAD antibody or a PAAD-associated polypeptide can be a reagent for a PAAD domain-containing polypeptide, whereas either an anti-PAAD antibody or an anti-PAAD-associated polypeptide antibody can be a reagent for a PAAD:PAAD-associated polypeptide complex.

As used herein, the term "test sample" means a cell or tissue specimen that is obtained from a subject and is to be examined for expression of a PAAD domain encoding gene in a cell in the sample. A test sample can be obtained, for example, during surgery or by needle biopsy and can be examined using the methods described herein to diagnose a pathology characterized by increased or decreased apoptosis. Increased or decreased expression of a PAAD domain encoding gene in a cell in a test sample can be determined, for example, by comparison to an expected normal level of PAAD domain-containing polypeptide or PAAD domain encoding mRNA in a particular cell type. A normal range of PAAD domain-containing polypeptide or PAAD domain encoding mRNA levels in various cell types can be determined by sampling a statistically significant number of normal subjects. In addition, a reference sample can be evaluated in parallel with a test sample in order to determine whether a pathology characterized by increased or decreased apoptosis is due to increased or decreased expression of a PAAD domain encoding gene. The test sample can be examined using, for example, immunohistochemical methods as described above or the sample can be further processed and examined. For example, an extract of a test sample can be prepared and examined to determine whether a PAAD domain-containing polypeptide in the sample can associate with a PAAD-associated polypeptide in the same manner as a PAAD domaincontaining polypeptide from a reference cell or whether, instead, a variant PAAD domain-containing polypeptide is expressed in the cell.

In accordance with another embodiment of he present invention, there are provided diagnostic systems, preferably in kit form, comprising at least one invention PAAD domain encoding nucleic acid, PAAD domain-containing polypeptide, and/or anti-PAAD antibody described herein, in a suitable packaging material. In one embodiment, for example, the diagnostic nucleic acids are derived from any of SEQ ID NOs:15, 17, 19, 21, 23, 25 or 27. Invention diagnostic systems are useful for assaying for the presence or absence of PAAD domain encoding nucleic acid in either genomic DNA or in transcribed PAAD domain encoding nucleic acid, such as mRNA or cDNA.

A suitable diagnostic system includes at least one invention PAAD domain encoding nucleic acid, PAAD domain-containing polypeptide, and/or anti-PAAD antibody, preferably two or more invention nucleic acids, proteins and/or antibodies, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular PAAD domain encoding sequence including the nucleotide sequences set forth in SEQ ID NOs:15, 17, 19, 21, 23, 25 or 27 or mutations or deletions therein, thereby diagnosing the presence of, or a predisposition for a pathology such as cancer or an autoimmune disease. In addition, the packaging material contains instructions indicating how the materials within the kit are employed both to detect a particular sequence and diagnose the presence of, or a predisposition for a pathology such as cancer or an autoimmune disease.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

A diagnostic assay should include a simple method for detecting the amount of a PAAD domain-containing polypeptide or PAAD domain encoding nucleic acid in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a labeled reagent with a test sample and, if desired, a control sample, specifically bound reagent can be identified by detecting the particular moiety.

A labeled antibody that can specifically bind the reagent also can be used to identify specific binding of an unlabeled reagent. For example, if the reagent is an anti-PAAD antibody, a second antibody can be used to detect specific binding of the anti-PAAD antibody. A second antibody generally will be specific for the particular class of the first antibody. For example, if an anti-PAAD antibody if of the IgG class, a second antibody will be an anti-IgG antibody. Such second antibodies are readily available from commercial sources. The second antibody can be labeled using a detectable moiety as described above. When a sample is labeled using a second antibody the sample is first contacted with a first antibody, then the sample iscontacted with the labeled second antibody, which specifically binds to the first antibody and results in a labeled sample.

All patents, publications and database sequences mentioned herein are incorporated in their entirety by reference thereto. The invention will now be described in greater detail by reference to the following non-limiting examples.

EXAMPLES 1.0 Identification of PAAD Domain-containing Polypeptides

Figure 2:
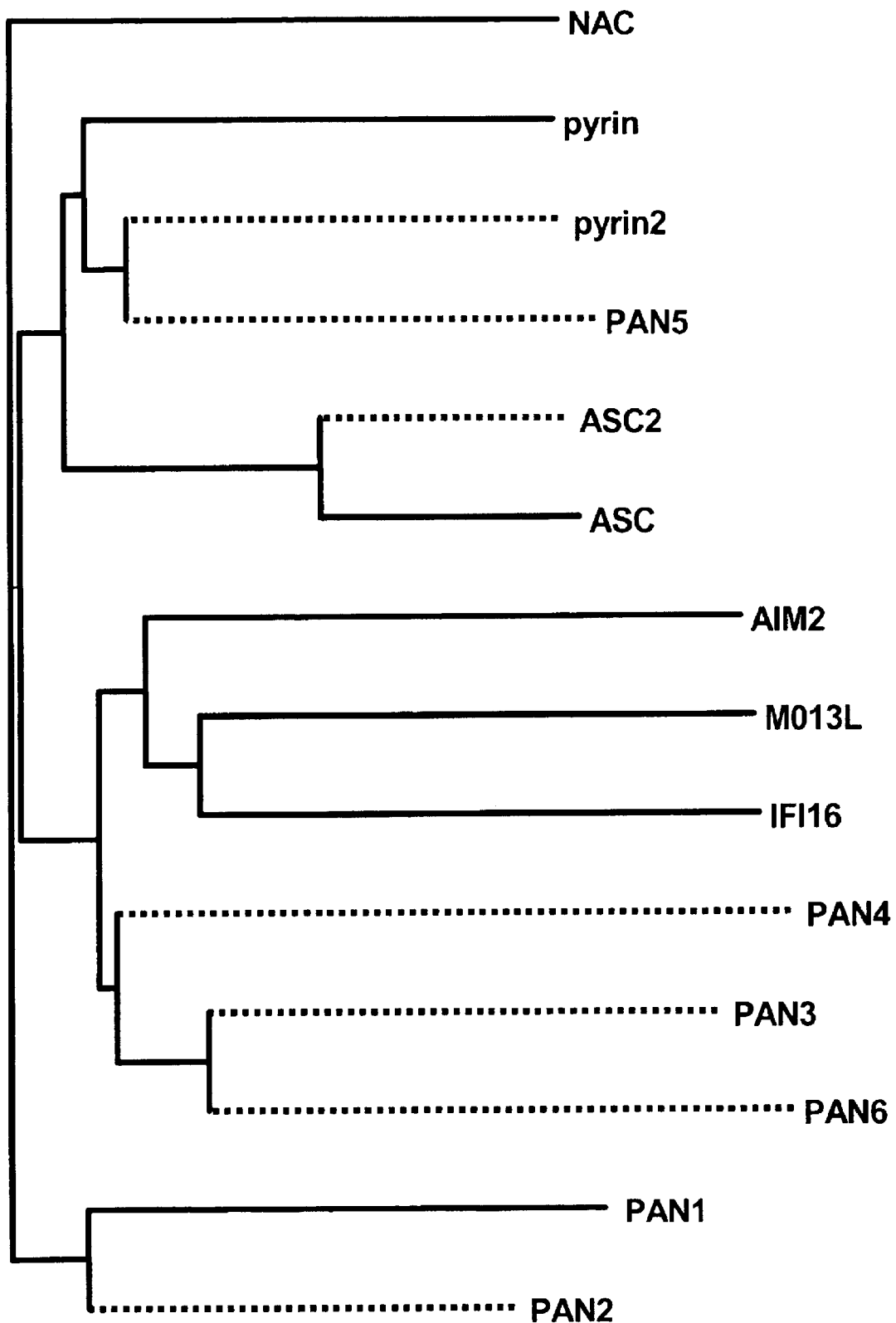
FIG. 2 shows the evolutionary tree showing the relationship between selected members of the PAAD family of proteins from humans and viruses. The tree was built using the CLUSTALW program. Proteins containing NB-ARC (NACHT) NTP-ase domains as well as PAAD domains (NAC and PAN1–6) are shown in grey.

The sequence of the N-terminal 100 amino acid fragment of the pyrin protein (Genbank Accession # NP00234; Pras, 1998, Scand. J. Rheumatol., 27:92–97) was used to perform a cascade of PSI-BLAST searches until no new hits were found. Lower significance hits from this procedure (called Saturated BLAST) were confirmed using the profile-to-profile alignment algorithm FFAS (Rychlewski et al., 2000, Protein Science 9:232–241) against a library of apoptosis-related domains. Proteins suspected of having a PAAD domain were added to the Saturated BLAST and FFAS databases and the FFAS similarity score was used to accept or reject the putative PAAD domains. Most of the proteins identified in FIGS. 1 and 2 could be connected with each other with PSI-BLAST significance better than 0.001 and/or the FFAS Z-score better than 10. The weakest link in the chain is the connection between the AIM2/IFI16 branch and the rest of the family (pyrin/ASC/caspase/NAC), with 0.05 PSI-BLAST E-value and FFAS Z-score of 8. The latter value was independently verified on a protein structure benchmark to give a correct match in more than 99% of cases (Rychlewski et al. supra). The same link was also confirmed by independent application of the Gibbs sampling algorithm (Lawrence, C. et al. (1993) Science 262:208–14), where sequence patterns identified in the pyrin/ASC/caspase branch of the family could be consistently used to find the AIM2/IFI16 group, albeit with low significance. In accordance with the present invention, this Saturated BLAST procedure resulted in the identification of several putative PAAD homologues in the unfinished nucleotide databases.

The process of gene identification and assembling include the following steps:

A) Identification or new candidate PAAD containing polypeptides. A iterative database search was performed using the TBLASTN program with PAAD domain of pyrin and all other identified PAAD domains as the query in the following NCBI databases: high throughput genome sequence (HTGS), genomic survey sequence (GSS) and expressed sequence tag (EST) databases.

B) Verification that the new candidate PAAD domain-containing polypeptide is novel. Using PSI-BLAST, each new candidate PAAD domain gene was queried in the annotated non-redundant (NR) database at NCBI. When the new candidate gene showed significant but not identical homology with other known PAAD domain-containing polypeptides during this search, the PAAD domain-containing polypeptide candidate was kept for further analysis.

C) 3-D-Model Building of new candidate PAAD domain polypeptide: When the sequence homology was low (<25% identity), three-dimensional criteria was added to characterization of new PAAD domain-containing polypeptides. The candidate PAAD domain fragment was analyzed by a profile-profile sequence comparison method which aligns the candidate PAAD domain with a database of sequences of known three-dimensional structure. From this analysis, a sequence alignment was produced and a model three-dimensional structure was built using DD, DED and CARD domains as templates. In most cases, the best score was produced using PAAD domain sequences having known three-dimensional structures. The quality of the three-dimensional model obtained from the alignments confirmed that novel PAAD domain-containing polypeptides had been identified.

D) Identification of additional domains in the full length protein. Full length protein sequences were obtained using the new PAAD domain identified in step B as query. TBLASTN searches of the sequences containing the newly identified PAAD domains were performed. Longer aligned fragments or multiple aligned fragments in the accession number corresponding to the newly identified PAAD domain-containing polypeptides indicated a longer PAAD domain-containing protein.

E) These additional domains were assembled using the following gene building procedure:

Genomic DNA fragments identified by T-BLAST-N analysis were extended and identified using exon prediction programs, such as Genescan, GRAIL, ORF-find, and the like; searching in both directions until start and stop codons were identified.

2.0 Identification of PAAD Domain-containing Polypeptides PAN2–6, Pyrin2 and ASC2.

Nucleic acids encoding PAAD domain-containing proteins corresponding to PAN2, PAN3, PAN4, PAN5, PAN6, Pyrin2 and ASC2 were identified from different PAAD domain queries using tblastn and systematically scanning gss, htgs, and all EST databases at NCBI. Further analysis using translated genomic fragments containing PAAD domains, which fragments were larger than the PAAD domain itself as query, were performed to identify additional domains. Genomic DNA were translated in all reading frames and examined for additional domains using psi-blast and nr database. Using this strategy, additional domains of PAAD domain-containing polypeptides, including a NB-ARC domain, LRR repeat and ANGIO-R domain, were identified.

3.0 Cloning and Sequencing of Large cDNA

For cDNA larger than 1500 bp, cloning is accomplished by amplification of multiple fragments of the cDNA. Jurkat total RNA is reverse-transcribed to complementary DNAs using MMLV reverse transcriptase (Stratagene) and random hexanucleotide primers. Overlapping cDNA fragments of a PAAD domain-containing polypeptide are amplified from the Jurkat complementary DNAs with Turbo Pfu DNA polymerase (Stratagene) using an oligonucleotide primer set for every 1500 bp of cDNA, where the amplified cDNA fragment contains a unique restriction site near the end that is to be ligated with an adjacent amplified cDNA fragment.

The resultant cDNA fragments are ligated into mammalian expression vector pcDNA-myc (Invitrogen, modified as described in Roy et al., *EMBO J.* 16:6914–6925 (1997)) and assembled to full-length cDNA by consecutively ligating adjacent fragments at the unique endonuclease sites form the full-length cDNA. Sequencing analysis of the assembled full-length cDNA is carried out, and splice isoforms of PAAD domain-containing polypeptides can be identified.

4.0 Plasmid Constructions.

Complementary DNA encoding a PAAD domain-containing polypeptide, or a functional fragment thereof is amplified from Jurkat cDNAs with Turbo Pfu DNA polymerase (Stratagene) and desired primers, such as those described above. The resultant PCR fragments are digested with restriction enzymes such as EcoRI and Xho I and ligated into pGEX-4T1 (Pharmacia) and pcDNA-myc vectors.

5.0 In vitro Protein Binding Assays.

PAAD domain-containing or fragments thereof encoded in pGEX-4T1 are expressed in XL-1 blue *E. coli* cells (Stratagene), and affinity-purified using glutathione (GSH)-sepharose according to known methods, such as those in *Current Protocols in Molecular Biology*, Ausubel et al. eds., John Wiley and Sons (1999). For GST pull-down assays, purified PAAD domain GST fusion proteins and GST alone (0.1–0.5 µg immobilized on 10–15 µl GSH-sepharose beads) are incubated with 1 mg/ml of BSA in 100 µl Co-IP buffer [142.4 mM KCl, 5 mM $M_gCl_2$, 10 mM HEPES (pH 7.4), 0.5 mM EGTA, 0.2% NP-40, 1 mM DTT, and 1 mM PMSF] for 30 min. at room temperature. The beads are then incubated with 1 µl of rat reticulocyte lysates (TnT-lysate; Promega, Inc.) containing $^{35}$S-labeled, in vitro translated PAAD domain-containing or control protein Skp-1 in 100 µl Co-IP buffer supplemented with 0.5 mg/ml BSA for overnight at 4° C. The beads are washed four times in 500 µl Co-IP buffer, followed by boiling in 20 µl Laemmli-SDS sample buffer. The eluted proteins are analyzed by SDS-PAGE. The bands of SDS-PAGE gels are detected by fluorography.

The resultant oligomerization pattern will reveal that PAAD:PAAD other protein:protein interactions occur with invention PAAD domain-containing polypeptides (e.g., PAN2 through PAN6, and the like) or fragments thereof.

In vitro translated candidate PAAD-associated polypeptides, along with a control, are subjected to GST pull-down assay using GSH-sepharose beads conjugated with GST and GST-PAAD domain-containing polypeptides as described above. Lanes containing GST-PAAD domain yield positive binding signals when incubated with a PAAD-associated polypeptide selected from APAF-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, IκB, p65, p50, IKAP, pyrin, pyrin2, PAN1, PAN2, PAN3, PAN4, PAN5, PAN6, ASC, ASC2, NAC, AIM2, IFI16, MO13L, p52, p100, p105, ParaCaspase (MALT1), and all members of the NFκB/IκB families, whereas, the controls GST alone and Skp-1 yield negligible signals.

6.0 Self-Association of NB-ARC Domain of PAAD Domain-containing Polypeptides.

In vitro translated, $^{35}$S-labeled rabbit reticulocyte lysates (1 µl) containing an NB-ARC domain of an invention PAN protein or a control protein, such as SKP-1, are incubated with GSH-sepharose beads conjugated with purified GST-NB-ARC or GST alone for GST pull-down assay, resolved on SDS-PAGE and visualized by fluorography as described above. One tenth of input is loaded for NB-ARC or Skp-1 as controls. The results indicate that the NB-ARC domains of invention PAN proteins can self-associate by binding through the NB-ARC domains.

7.0 Protein-Protein Interactions of PAAD Domain-containing Polypeptides.

Transient transfections of 293T, a human embryonic kidney fibroblast cell line, are conducted using SuperFect reagents (Qiagen) according to manufacturer's instructions. 293T cells are transiently transfected with an expression plasmid (2 μg) encoding HA-tagged Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-1, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, IκB, p65, p50, IKAP, pyrin, pyrin2, PAN1, PAN2, PAN3, PAN4, PAN5, PAN6, ASC; ASC2, NAC, AIM2, IFI16, MO13L, p52, p100, p105, ParaCaspase (MALT1), and all members of the NFκB/IκB families, or the like, in the presence or absence of a plasmid (2 μg) encoding a myc-tagged PAAD domain-containing polypeptide. After 24 hr growth in culture, transfected cells are collected and lysed in Co-IP buffer [142.4 mM KCl, 5 mM $MgCl_2$, 10 mM HEPES (pH 7.4), 0.5 mM EGTA, 0.1% NP-40, and 1 mM DTT] supplemented with 12.5 mM β-glycerolphosphate, 2 mM NaF, 1 mM $Na_3VO_4$1 mM PMSF, and 1×protenase inhibitor mix (Boehringer Mannheim). Cell lysates are clarified by microcentrifugation and subjected to immunoprecipitation using wither a mouse monoclonal antibody to myc (Santa Cruz Biotechnologies, Inc.) or a control mouse IaG. Proteins from the immune complexes are resolved by SDS-PAGE, transferred to nitrocellulose membranes, and subjected to immunoblot analysis using anti-HA antibodies followed by anti-myc antibodies using a standard Western blotting procedure and ECL reagents from Amersham-Pharmacia Biotechnologies, Inc. (Krajewski et al., *Proc. Natl. Acad. Sci. USA* 96:5752–5757 (1999)).

The results indicate that invention PAAD domain-containing polypeptides can bind to themselves (e.g., homodimers, and the like) and to one or more polypeptides selected from Apaf-1, CED4, Nod1/CARD4, ASC-1, CARDX1, pro-Casp1, pro-Casp2, pro-Casp4, pro-Casp5, pro-Casp7, pro-Casp11, pro-Casp12, pro-Casp14, CED3, Dronc, Raidd/CRADD, Cardiak (RIP2, Rick), Bcl-1/CIPER, ARC, NOP30, cIAP-1, cIAP-2, Fadd/mort1, pro-Casp8, pro-Casp10, Dredd, c-Flip/flame, KSV/V-Flip, MCV, DEDD/DEFT, PEA-15, Flash, BAP31, BAR, RIP, IRAK-1, IRAK-2, IRAK-M, My D88, NMP-84, Ankyrin-1, Ankyrin-3, TNFR1, NGFR, Fas, DR3, DR4, DR5, DR6, Tradd, Fadd, Raidd2, DAP Kinase, NIK, IKKα, IKKβ, p65, P50, IKAP, pyrin, pyrin2, PAN1, PAN2, PAN3, PAN4, PAN5, PAN6, ASC, ASC2, NAC, AIM2, IFI16, MO13L, p52, p100, p105, ParaCaspase (MALT1), and all members of the NFκB/IκB families.

8.0 Cloning and Characterization of PAN2

As a first step in cloning PAN2 cDNA, RT-PCR was performed on total RNA from HeLa cells using oligo dT to prime the first-strand synthesis and then 2 PAN2-specific primers designated PAN2/5': 5'-CCGGAATTCACC<u>ATG</u>GCAGCCTCTTTCTTCTCTG-ATTTT-3' (SEQ ID NO:35) and PAN2/3': 5'-CCGCTC-GAG<u>TCA</u>CGTAGAGCTGTGTTCATCCTCTTTCTTAA-3' (SEQ ID NO:36). These primers were designed based on the predicted PAN2 open reading frame identified in the genomic sequence AC022066, as described in Example 2.0. The ATG of PAN2 and an artificial stop codon inserted after amino acid 620 are underlined in SEQ ID NOS:35 and 36, respectively. EcoRI and XhoI restriction sites are shown in italics in SEQ ID NOS:35 and 36, respectively. The resulting PCR product was cloned into a pcDNA3Myc expression vector at the EcoRI(5') and XhoI(3'), and sequenced.

A BLAST search of the human EST database was then performed using the partial PAN2 sequence. Several EST clones were identified, and several corresponding I.M.A.G.E. Consortium cDNA clones (Lennon et al., *Genomics* 33;151–152 (1996)) were obtained. I.M.A.G.E. Consortium CloneID 3139498, corresponding to EST GenBank Accession Number BE278926, was sequenced and determined to contain full-length PAN2 cDNA, including the stop codon, the 3' UTR of the gene and the poly-A tail.

The complete coding sequence of PAN2 was cloned by PCR from I.M.A.G.E. Consortium CloneID 3139498 by PCR, using as the 5' primer SEQ ID NO:35 and as the 3' primer PAN2STOP4: 5'-CCTCTCGAGTCAGATCTCTA-CCCTTGTGATTGTGTCAC-3' (SEQ ID NO:40). The PAN2 cDNA was independently amplified from HeLa cells using overlapping primers to confirm that the I.M.A.G.E. clone contained an intact, single cDNA. The PAN2 cDNA coding sequence (SEQ ID NO:15) is 2985 nucleotides and encodes an amino acid sequence (SEQ ID NO:16) of 995 amino acids.

Several domains within PAN2 were identified, based on homology with known proteins. The PAAD domain (SEQ ID NO:2) corresponds to amino acids 14–89 of SEQ ID NO:16. The nucleotide-binding domain (NB-ARC) (SEQ ID N:37) corresponds to amino acids 147–336 of SEQ ID NO:16. The Angiotensin receptor-like domain (AR-like) (SEQ ID NO:38) corresponds to amino acids 465–605 of SEQ ID NO:16. The Leucine rich region (LRR) (SEQ ID NO:39) corresponds to amino acids 620–995 of SEQ ID NO:16.

Expression of PAN2 in human tissues was determined using a panel of Clontech (Palo Alto, Calif.) first-strand cDNAs to amplify a region of PAN2 corresponding to the NB-ARC domain (amino acids 147–465), following manufacturer's recommended procedures. PAN2 was found to be expressed in several human tissues, including placenta, lung, liver, muscle, kidney, pancreas, spleen, thymus, prostate, testis and ovary.

In order to determine whether the PAAD domain of PAN2 is able to self-associate, fusions of the PAN2 PAAD domain (amino acids 1–89 of SEQ ID NO:16) and PAN2(1–620) (amino acids 1–620 of SEQ ID NO:16) with glutathione-S-transferase (GST) were constructed, expressed in bacteria and attached to glutathione beads. The GST fusion proteins were used to pull down in vitro-translated PAN2 PAAD or PAN2(1–620). GST alone and GST-CD40 were used as controls. The PAAD domain of PAN2 was determined not to self-associate or to associate with PAN2. However, PAN2 (1–620) was determined to self-associate, likely through its NB-ARC domain. Therefore, the PAAD domain is likely not involved in PAN2/PAN2 interactions.

The effect of expression of the PAN2 PAAD domain on NF-κB activation by the TNFα pathway and IL-1β pathway were assessed as follows. 10,000 293N cells were seeded into 96-well plates and cells were transfected the following day using SuperFect™ transfection reagent (Qiagen, Venlo, The Netherlands) with 10 ng of pNFκB-luc and 2.5 ng of thymidine kinase promoter-Renilla luciferase (pRL-TK) reporter vectors (Stratagene, San Diego, Calif.) together with 100 ng of plasmids encoding proteins in the TNF-α pathway (pCMV TNFR1, pcDNA3 Traf2 or pcDNA3HA RIP) or in the IL-β pathway (pCMVFlag IL-1R, pcDNA3His MyD88, pcDNA3HA IRAK3 or pcDNA3HA Traf6), and either 400 ng of pcDNA3Myc ("Empty") or 400 ng of pcDNA3Myc PAAD 1–89 ("PAAD"). After 36 hours, cells were harvested and luciferase activities were determined using the Dual Luciferase System (Promega, Madison, Wis.).

The results of the luciferase assays for cells transfected with molecules in the TNFα pathway are shown in Table 1, below. For the "TNFα" condition, cells were stimulated with 10 ng TNFα for 6–8 hours prior to lysis. The numbers indicate the fold induction of NFκB activity.

TABLE 1

|  | TNFR1 | TNFα | TRAF2 | RIP |
| --- | --- | --- | --- | --- |
| EMPTY | 20.04 | 21.05 | 33.53 | 53.93 |
| PAAD2 | 19.62 | 7.14 | 15.75 | 23.51 |

The results of the luciferase assays for cells transfected with molecules in the IL-1β pathway are shown in Table 2, below. The numbers indicate the fold induction of NFκB activity.

TABLE 2

|  | IL1R | MyD88 | IRAK2 | TRAF6 |
| --- | --- | --- | --- | --- |
| EMPTY | 6 | 28.16 | 10.27 | 28.17 |
| PAAD2 | 4.27 | 21.23 | 4.58 | 20.41 |

The results of the NFκB activation assays shown in Tables 1 and 2 indicate that expression of the PAAD domain of PAN2 significantly inhibits NFκB activation by either the TNFα or the IL-1β pathway.

Expression of full-length PAN2 was also demonstrated to inhibit NFκB activation by either the TNFα or the IL-1β pathway. At the same DNA concentration, the inhibition of NFκB activation following transfection with pcDNA3Myc PAN2 was almost the same as the extent of inhibition following transfection with pcDNA3Myc PAAD 1–89. It was concluded that inhibition of NFκB activation by PAN2 was mediated by the PAAD domain.

Figure 5:
FIG. 5 shows a luciferase reporter assay in which NFκB transcription activity was determined in cells transfected with NIK, IKKα or IKKβ and either an empty vector or the indicated amounts of a vector expressing PAN2.

In order to determine whether PAN2 affects activation of NFκB mediated by upstream components in the NFκB activation pathway, plasmids encoding either NIK (pCMV-NIK), IKKα (pRE-HA-IKKα) or IKKβ (pRE-HA-IKKβ) were co-transfected into 293N cells as described above with from 10 ng to 300 ng of pcDNA3Myc PAN2 or with empty vector, together with 10 ng of pNFκB-luc and 2.5 ng of pTK-RL. Luciferase activities determined as described above. As shown in FIG. 5, PAN2 expression dose-dependently blocked the activation of NFκB mediated by either NIK, IKKα or IKKβ. Therefore, PAN2 acts downstream of the IκB kinase complex.

NFκB is normally sequestered into the cytoplasm of nonstimulated cells by a family of inhibitory proteins, called IκB (α, β, γ and ε). Exposure of cells to various stimuli leads to the rapid phosphorylation, ubiquitination and proteolytic degradation of IκB, which frees NFκB to translocate to the nucleus where it regulates gene expression. Accordingly, it was hypothesized that the PAN2 inhibitory effect on NFκB activation could be related to IκB. To test this hypothesis, the in vivo interactions between PAN2 and IκBα were determined.

For co-immunoprecipitation experiments, HEK293T cells were seeded at 3×10⁶ cells per well in 100 mm dishes and transfected with 6–8 μg plasmid DNA using Lipofectamine Plus™ transfection reagent (GIBCO) 24 hours later. After culturing for 36 hours, cells were collected, washed in PBS and lysed in isotonic lysis buffer [150 or 500 mM NaCl, 20 mM Tris/HCl (pH 7.4), 1% NP-40, 12.5 mM β-glycerophosphate, 2 mM NaF, 1 mM Na₃VO₄, 1 mM PMSF, and 1×protease inhibitor mix (Roche). Lysates were clarified by centrifugation and subjected to immunoprecipitation using agarose-conjugated anti-c-Myc antibodies (Santa Cruz) or anti-FlagM2 antibodies (Sigma) or nonspecific control antibodies and Protein G-agarose for 2–4 hours at 4° C. Immune-complexes were washed 3–5 times with lysis buffer and once with PBS, boiled in 1.5×Laemmli buffer, and separated by 12–15% PAGE. Immune-complexes were then transferred to PVDF membranes (Millipore) and immunoblotted with anti-c-Myc (Santa Cruz) or anti-Flag (Sigma) antibodies in 5% dry milk in TBS-T. Membranes were washed, incubated with HRP-conjugated secondary antibodies, and reactive proteins were detected using ECL.

Figure 6:
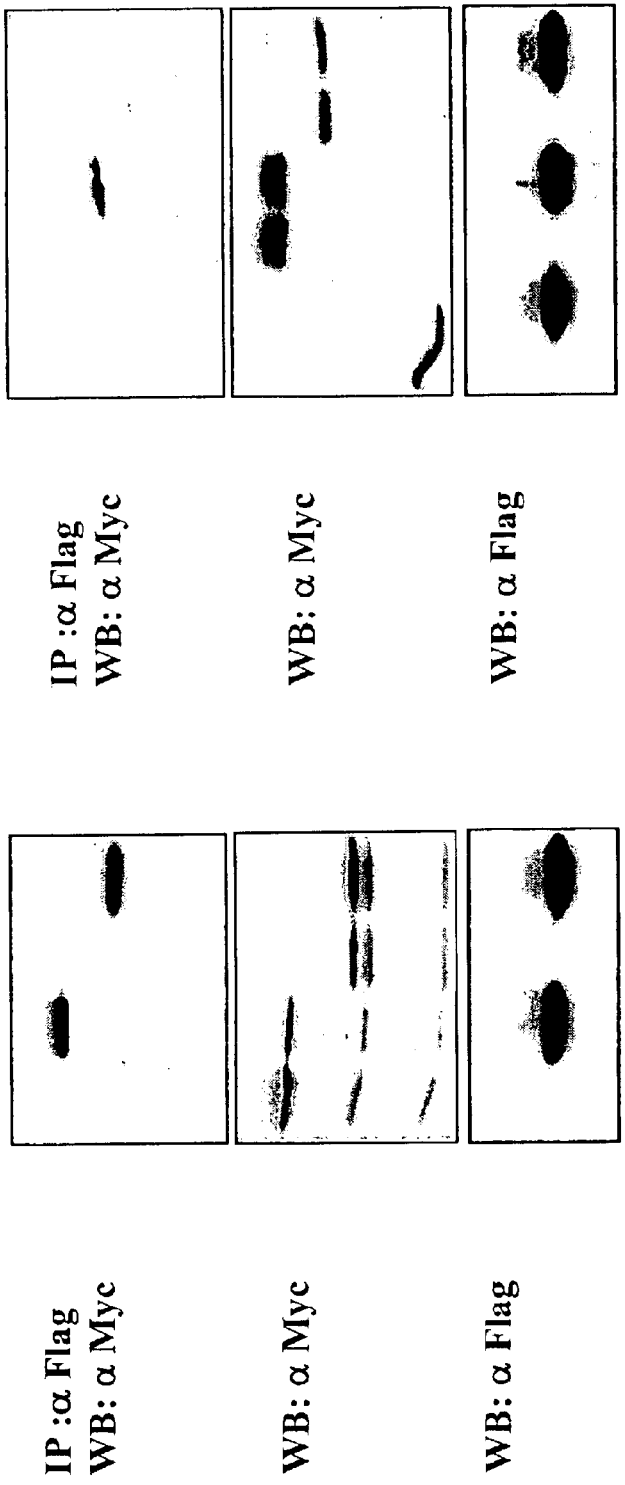
FIG. 6 shows a protein interaction assay in which vectors expressing Myc-tagged PAN2, or Myc-tagged domains of PAN2 as indicated, and either Flag-tagged IKBα or Flag-tagged empty vector, were co-transfected into 293T cells. The lysates were immunoprecipitated with an anti-Flag antibody and blotted with either an anti-Myc or an anti-Flag antibody.

As shown in FIG. 6, Flag-tagged IκBα co-immunoprecipitated with Myc-tagged PAN2 ("f.l.") when both plasmids were expressed in 293T cells.

In order to determine which domain of PAN2 is responsible for association with IκB, the following constructs were coexpressed in 293T cells with Flag-tagged IκBα or an empty Flag-tagged vector: Myc-tagged full-length PAN2, Myc-tagged PAN2 ΔLRR (amino acids 1–619 of PAN2), Myc-tagged PAN2PAAD (amino acids 1–89 of PAN2), Myc-tagged PAN2NBARC (amino acids 147–465 of PAN2) or Myc-tagged PAN2AR-like (amino acids 336–605 of PAN2). Immunoprecipitation and immunoblot assays were performed as described above.

As shown in FIG. 6, Flag-tagged IκBα co-immunoprecipitated with Myc-tagged full-length PAN2 ("f.l."), Myc-tagged PAN2 ΔLRR, and Myc-tagged PAN2NBARC, each of which contained the NBARC domain, but not with. Myc-tagged PAN2PAAD or Myc-tagged PAN2AR-like.

These results indicate that the NBARC domain of PAN2 is responsible for association with IκBα, whereas the PAAD domain of PAN2 is responsible for inhibition of NFκB interaction.

9.0 Cloning and Characterization of PAN5

In order to clone PAN5 cDNA, first strand cDNA was synthesized at 42° C. for 1 hour from HeLa total RNA (1 μg) using the PAN5 specific primer (300 ng): L1515 ( reverse): TTGCTCGAGTCATCTGAATAC (SEQ ID NO:53), and the ProStart Ultra HF RT-PCR system (Stratagene) as described by the manufacturer. A control mRNA and primers provided in the kit were also used (positive control). The completed first-strand cDNA was used for PCR amplification using Pfu DNA polymerase (2.5 units) and PAN5-specific primers (100 ng each), U1 (forward: ATGGCCATG-GCCAAGGC CAGAAAGC (SEQ ID NO:54) and L1515 (reverse): TTGCTCGAGTCATCTGAATAC (SEQ ID NO:55). The following PCR conditions were used: 4' HOT start at 94° C., 35 cycles of 94° C. denaturation for 1 minute, 44° C. annealing for 1 minute and extension at 72° C. for 2 minutes and a final 10 minute extension at 72° C. A 1515 bP PCR product corresponding to PAN5 was observed on an agarose gel. The resultant PCR product was cloned into pcDNA4-His/Max Topo (Invitrogen) following the recommendations of the manufacturer.

The PAAD domain of PAN5 ("PAAD5"), corresponding to bp34–271 of PAN5 cDNA (SEQ ID NO:21), encoding amino acids 12–90 of SEQ ID NO:22, was amplified by PCR from a HeLa cDNA library using the primer set EA-PAC5-Eco-U34: GAATTCCTCTGGGCCTTGAGT-GACCTTGAG (SEQ ID NO:51) and EA-PAC5-Xho-St-L271: CCAGCCGACCTCGAGCAGTCAAATATGGC (SEQ ID NO:52). PCR reactions contained in a total volume of 50 μl: 10×PCR buffer, 20 mM each dNTPs, amplitaq polymerase (0.5 U), 100 ng HeLa cDNA, 5 ng of each primer and 10% DMSO. The same mixture lacking DNA was used as a negative control. The PCR conditions used were as follows: the DNA was first denatured for 3 minutes (hot start). The prime mixture was then added and for 30 subsequent cycles of PCR, the samples were denatured at 94° C. for 30 seconds, annealed at 44° C. for 30 seconds and extended at 72° C. for 1 minute. The 30 cycles of PCR were followed by a 10 minute extension at 72° C.

The PAAD5 domain was first cloned into pCR-II-Topo, sequence-verified and then digested with EcoR1/Xho1. The digest was then analyzed by gel electrophoresis and the 238 bp band containing PAAD5 domain gel purified for sub-cloning into pcDNA3-Myc at the EcoR1/XhoI sites for expression in mammalian cells.

In order to determine the effect of PAN5 or the PAAD5 domain on NFκB activation, HEK293 cells were transiently transfected using SuperFect™ transfection reagent (1.5 μl/well) with pNFκB-Luc (50 ng) and pRL-TK (10 ng) luciferase reporter constructs, pcDNA3-PAAD5 or cDNA4-PAN5 (390 ng) and 50 ng each of different components of the TNF, LPS or IL signaling pathways, as indicated in Table 3. After incubation for 3 hours, the transfection reagent was removed, fresh serum-containing media was added and cells were then incubated for 36 hours. After 36 hours, cells were lysed with Passive lysis buffer (1x; Promega) and then the effect of PAAD5 domain or PAN5 on NFκB activaty was measured with a luminometer. Co-transfection of pToF-Flash/β-catenin was used as a control for stickiness.

The results of the luciferase assays are shown in Table 3, below.

TABLE 3

| Construct | NFkB Activity (fold induction) |
|---|---|
| Control | 1 |
| TNFα | 24 |
| PAAD5 | 3 |
| PAN5 | 4 |
| TNFR1 | 23 |
| TNFR1/PAAD5 | 21 |
| TNFR1/PAN5 | 24 |
| NIK | 30 |
| NIK/PAAD5 | 5 |
| NIK/PAN5 | 3 |
| IKKβ | 45 |
| IKKβ/PAAD5 | 6 |
| IKKβ/PAN5 | 8 |
| p65 | 55 |
| p65/PAAD5 | 13 |
| p65/PAN5 | 46 |
| ToF-Flash + β-catenin | 16 |
| ToF-Flash + β-catenin/PAAD5 | 15 |
| ToF-Flash + β-catenin/PAN5 | 17 |

As evidenced by the data shown in Table 3, overexpression of either PAN5, or the PAAD domain of PAN5, inhibits NFκB activation by a variety of proteins in the TNF, LPS or IL signaling pathways. Therefore, the PAAD domain of PAN5, like the PAAD domain of other PAN proteins described herein, is responsible for the inhibition of NFκB activation.

In order to determine the expression of PAN5 in human tissues, a commercially available Northern membrane (Stratagene) was prehybridized with QuikHyb hybridization solution (Stratagene) containing single stranded sperm DNA for 1–2 hours at 68° C. $^{32}$P-primer labeling of the DNA probe (the 1.5 kb fragment corresponding to the PAN5 ORF) was performed at 37° C., for 30 minutes, using the RTS radprime DNA labeling kit (Life Technologies), as described by the manufacturer. The $^{32}$P-primer labeling reaction contained 25 ng of denatured DNA, dATP, dAGTP, dTTP, random octamer primers, 50 μCi [$^{32}$P] dCTP and Klenow fragment. The prehybridization solution was removed, and the denatured radiolabeled probe was added to the hybridization solution (same as prehybridization buffer) and the membrane was hybridized overnight at 68° C. The membrane was washed three times for 40' with 2×SSC/0.05% SDS at room temperature, washed twice for 40' at 50° C., and exposed to Kodak XAR-5 film with intensifying screens at −70° C. C for 1–3 days.

Two transcripts, of 1.8 kb and 1.35 kb, were found to be expressed at varying levels in most human tissues tested. Thymus, spleen, placental and lung had the highest expression of PAD5 transcripts. In thymus and spleen, the 1.35 kb transcript was more abundant than the 1.8 kb transcript, whereas in placenta the 1.8 kb transcript was more abundant than the 1.35 kb transcript.

10.0 Cloning and Characterization of PAN6

The PAAD domain of PAN6 ("PAAD6") corresponding to bp34–271 of PAN6 cDNA (SEQ ID NO:23), encoding amino acids 12–90 of SEQ ID NO:24, was amplified by PCR from HeLa cDNA library using the primer set EA-PAAD6-U22: GACGGATCCTGTGGCATGGCCACCTACTTGG (SEQ ID NO:56) and EA-PAAD6-L291: ATCCCTCACGAATTC-CCCTCACTGTCCTC (SEQ ID NO:57), essentially as described for PAAD5. The PAAD 6 domain was first cloned into pCR-II-Topo, sequence-verified and then digested with BamH1 and Xho1. The 270 bp band containing the PAAD 6 domain was gel purified and ligated into pcDNA3-Myc for expression in mammalian cells, into pGEX-4T.3 for GST-fusion protein production and into pGilda for yeast two-hybrid studies, at the BamH1/Xho1 sites of the relevant vector.

In order to determine the effect of PAAD6 expression on NFκB activation, HEK293 cells were transiently transfected with pNFκB-Luc (50 ng) and pRL-TK (10 ng) luciferase reporter constructs, pcDNA3-PAAD6(390 ng) and 50 ng each of different components of the TNF, LPS or IL signaling pathways, as indicated in Table 4, as described above for PAAD5.

The results of the luciferase assays are shown in Table 4, below.

TABLE 4

| Construct | NFkB Activity (fold induction) |
|---|---|
| Control | 1 |
| TNFα | 20 |
| PAAD6 | 4 |
| IRAK2 | 18 |
| IRAK2/PAAD6 | 2 |
| TRAF2 | 44 |
| TRAF2/PAAD6 | 5 |
| TRAF6 | 45 |
| TRAF6/PAAD6 | 6 |
| NIK | 29 |
| NIK/PAAD6 | 3 |
| RIP | 45 |
| RIP/PAAD6 | 2 |
| p65 | 50 |
| p65/PAAD6 | 11 |
| IKKβ | 42 |
| IKKβ/PAAD6 | 2 |
| Bcl10 | 10 |
| Bcl10/PAAD6 | 1 |
| Nod1 | 17 |
| Nod1/PAAD6 | 18 |
| TNFR1 | 25 |
| TNFR1/PAAD6 | 19 |

TABLE 4-continued

| Construct | NFkB Activity (fold induction) |
|---|---|
| ToF-Flash + β-catenin | 18 |
| ToF-Flash + β-catenin/PAAD6 | 17 |

As evidenced by the data shown in Table 4, overexpression of the PAAD domain of PAN6 inhibits NFκB activation by a variety of proteins in the TNF, LPS or IL signaling pathways. Therefore, the PAAD domain of PAN6, like the PAAD domain of other PAN proteins described herein, is responsible for the inhibition of NFκB activation.

In order to identify proteins that associate with PAN6 in vivo, the pGilda plasmid was used to express as a "bait" protein the PAAD domain of PAN6 (nucleotides 22–291 of PAN6 cDNA, corresponding to amino acids 8–97 of SEQ ID NO:24). The plasmid expressing the LexA-PAAD6 bait protein was then used to transform the yeast strain EGY48 (MAT,trp1,ura3, his,his leu2::6LexAop-LEU2. The ability of the LexA-2-PAAD6 bait protein alone to activate LEU2 or LacZ reporter genes was also tested. The LexA-PAAD6 bait protein was used to screen a human fetal brain and Jurkat T cell pJG4–5 cDNA libraries. Briefly, cells were grown in either YPD medium with 1% yeast extract, 2% polypeptone and 2% glucose, or in Burkholder's minimal medium (BMM) supplemented with appropriate amino acids. Transformations were performed by a LiCl method using 0.1 mg of pJG4–5 cDNA library DNA and 5 mg denatured salmon sperm DNA. The potential positive transformants that grew on Leu deficient BMM plates containing 2% galactose were transferred to BMM plates containing leucine and 2% glucose. Filter assays were then performed to measure 5-galactosidase activity as described in Sato et al. *Proc. Natl. Acad. Sci USA* 91:9238–9242 (1994). As a result of the screening, 7 β-galactosidase positive clones out of 11 clones from the Jurkat T cell cDNA library were obtained that transactivated the LEU2 reporter gene (based on the ability to grow on leu deficient media). The screening of a fetal brain cDNA library gave 430 positive clones for the transactivation of the LEU2 reporter gene. Of those, 42 colonies were also positive in the β-galactosidase assay.

Two of the clones identified encoding PAAD6-interacting proteins by yeast two hybrid analysis encoded IKAP, which is an IKβ kinase complex associated protein. The region of IKAP that interacted with PAAD6 was within amino acids 1089–1232. IKAP is known in the art and described, for example, in Cohen et al., *Nature* 395:292–296 (1998).

In order to determine the expression of PAAD6 in human tissues, a commercially available Northern membrane (Stratagene) was hybridized as described above in regard to PAN5 expression, using the EST I.M.A.G.E. clone 2900568, corresponding to nucleotides 892–2331 of PAN6 as the radiolabeled probe.

A PAN6 transcript of 3.3 kb was observed at highest levels in thymus, spleen and skeletal muscle, with lower levels in other tissues.

11.0 Cloning and Characterization of ASC and ASC2

ASC and ASC2 were cloned as following. The ASC or ASC2 (SEQ ID NO:27) open reading frames, or the ASC CARD or PAAD domains, were amplified by high fidelity PCR using primers containing EcoRI and XhoI sites and sub cloned into pcDNA3 vectors containing Myc, Flag or HA epitope tags on the N- or C-terminal end. As template either the ASC cDNA described in Masumoto et al., *J. Biol. Chem.* 274:33835–33838 (1999) or the 619 bp EST with GenBank Accession No. W73523 (gi:1383656) were used. Authenticity of all constructs was confirmed by DNA sequencing. The primers used were as follows:

```
                              (SEQ ID NO: 41)
ASC:      5'-GAATTCGATCCTGGAGCCATGGGG-3';

(SEQ ID NO: 42)
          5'-CTCGAGCCGGAGTGTTGCTGGGAA-3';

(SEQ ID NO: 43)
ASC-PAAD: 5'-GAATTCGATCCTGGAGCCATGGGG-3;

(SEQ ID NO: 44)
          5'-CTCGAGTCAGCTTGGCTGCCGACT-3' or (SEQ ID NO: 45)
          5-CCCCCTCGAGGGCCTGGCTTGGCTGCCGACT-3';

(SEQ ID NO: 46)
ASC-CARD: 5'-GAATTCCCTCAGTCGGCAGCCAAG-3';

(SEQ ID NO: 47)
          5'-CTCGAGCCGGAGTGTTGCTGGGAA-3';

(SEQ ID NO: 48)
ASC2:     5'-GAATTCGAGGCGCAGGGCTGTG-3';

(SEQ ID NO: 49)
          5'-CTCGAGGCTTCACAGGCGTTGCAT-3' or (SEQ ID NO: 50)
          5'-CTCGAGGCTACACAGGCGTTGCAT-3'.
```

ASC contains a PAAD domain at the N-terminus followed by a CARD domain. ASC2 contains only a PAAD domain, which shares extensive sequence homology with the PAAD domain of ASC. The ASC gene is localized at chromosome 16p12–11.2, whereas the ASC2 gene is localized at chromosome 16.p13.

To determine associations between various domains of ASC and ASC2, GST pull-down assays and yeast two-hybrid assays were performed. For GST pull-down assays, ASC-PAAD and ASC2 were subcloned into pGEX4-T1 (Pharmacia) and affinity purified as GST-fusion proteins from *E. coli* XL-1 blue (Stratagene) using GSH-Sepharose. Purified GST-fusion proteins (0.1 μg) immobilized on 10–15 μl of GSH-Sepharose beads were incubated with 1 mg/ml bovine serum albumin in 100 μl buffer A [142.4 mM KCl, 5 mM MgCl$_2$, 10 mM HEPES (pH 7.4), 0.5 mM EGTA, 1 mM EDTA, and 0.2% Nonidet P-40, supplemented with 1 mM dithiothreitol, 12.5 mM β-glycerol phosphate, 1 μM Na$_3$VO$_4$, 1 mM phenylmethylsulfonyl fluoride, and 1×protease inhibitor mix (Roche)] for 30 min at 25° C. The beads were washed twice and incubated overnight at 4° C. with 1 μl of rabbit reticulocyte lysate (Quick-TNT-lysate, Promega) containing $^{35}$S-labeled, in vitro-translated proteins in 100 μl of buffer A supplemented with 0.5 mg/ml bovine serum albumin. Bound proteins were washed four times in 500 μl of buffer A, followed by boiling in 20 μl of Laemmli-SDS sample buffer, SDS-PAGE and detected by fluorography.

By the GST pull-down assays, the PAAD domain of ASC did not associate with the CARD domain of ASC, but weakly associated with full-length ASC and with ASC2, suggesting that the PAAD domain of ASC self-associates and also associates with ASC2.

For the yeast two-hybrid assays, the yeast EGY-48 strain was transformed with various combinations of ASC, ASC- CARD, ASC-PAAD, and ASC2 in the plasmids pGilda and pJG 4–5, together with the β-galactosidase expression plasmid pSH-18–34 (Invitrogen). Colonies were plated on both LEU+ and LEU– media and also used for a β-Gal-assay. The results of the yeast interaction assays are shown in Table 5, below.

TABLE 5

| pJG 4–5 | pGilda | Leu | β-Gal |
|---|---|---|---|
| ASC-CARD | ASC-CARD | + | + |
| ASC-CARD | empty | – | – |
| ASC-CARD | ASC | + | + |
| ASC-CARD | ASC-PAAD | – | – |
| ASC-CARD | ASC2 | – | – |
| ASC-PAAD | empty | – | – |
| ASC-PAAD | ASC-PAAD | + | + |
| ASC2 | empty | – | – |
| ASC2 | ASC2 | + | – |
| ASC2 | ASC | + | + |
| ASC | empty | – | – |

As shown in Table 5, the CARD domain of ASC self associates. In this in vivo assay, the PAAD domain of ASC was shown to self-associate, and also to associate with ASC2.

For co-immunoprecipitation experiments, HEK293T cells were seeded at 5×10$^5$ cells per well in six-well plates (35 mm wells) and transfected with 2 µg plasmid DNA using Superfect (Qiagen) 24 hours later. After culturing for 36 hours, cells were collected, washed in PBS and lysed in isotonic lysis buffer [150 or 500 mM NaCl, 20 mM tris/HCl (pH 7.4), 0.2% NP-40, 12.5 mM β-glycerophosphate, 2 mM NaF, 1 mM Na$_3$VO$_4$, 1 mM PMSF, and 1×protease inhibitor mix (Roche). Lysates were clarified by centrifugation and subjected to immunoprecipitation using agarose-conjugated anti-c-Myc antibodies (Santa Cruz), anti-HA antibodies (Santa Cruz, Roche) anti-FlagM2 antibodies (Sigma) or non-specific control antibodies and Protein G-agarose for 2–4 hours at 4° C. Immune-complexes were washed 3–5 times with lysis buffer and once with PBS, boiled in 1.5× Laemmli buffer, and separated by 12–15% PAGE next to 10% of the total lysate. Immune-complexes were then transferred to PVDF membranes (Millipore) and immunoblotted with anti-c-Myc (Santa Cruz), anti-HA (Roche), or anti-Flag (Sigma) antibodies in 5% dry milk in TBS-T. Membranes were washed, incubated with HRP-conjugated secondary antibodies, and reactive proteins were detected using ECL.

The results of the co-immunoprecipitation assays are shown in Table 6, below, with a "+" sign indicating co-immunoprecipitation.

TABLE 6

| Myc-ASC | HA-ASC | + |
|---|---|---|
| Myc-Caspase-1 | HA-ASC | + |
| Myc-Card10 | HA-ASC | + |
| Flag-Nod1 | HA-ASC | + |
| Flag-Cardiak | HA-ASC | + |
| Myc-ASC2 | HA-ASC-PAAD | + |
| Flag-Nod1 | HA-ASC-PAAD | + |
| Flag-Cardiak | HA-ASC-PAAD | + |
| Myc-NIK | HA-ASC-PAAD | + |
| Flag-IKK-i | HA-ASC-PAAD | + |
| Flag-IκBα | HA-ASC-PAAD | – |
| HA-IKKβ | Myc-ASC-PAAD | – |

The results shown in Table 6 indicate that ASC associates with ASC, ASC2, Caspase-1, CARD10, Nod1, Cardiak, NIK and IKK-i.

GST pull-down assays, as described above, were used to determine whether the CARD domain of ASC is able to associate with other proteins, including other CARD domain-containing proteins. The results of these assays are shown in Table 7, with a "+" indicating a detectable interaction between the GST-ASC-CARD domain and the indicated in vitro-translated (IVT) test protein.

TABLE 7

| GST-ASC-CARD/IVT Caspase-8 | – |
|---|---|
| GST-ASC-CARD/IVT Caspase-9 | – |
| GST-ASC-CARD/IVT Caspase-10 | – |
| GST-ASC-CARD/IVT Bcl-10 | – |
| GST-ASC-CARD/IVT RAIDD | – |
| GST-ASC-CARD/IVT ASC-2 | – |
| GST-ASC-CARD/IVT ASC | + |
| GST-ASC-CARD/IVT Xiap | – |
| GST-ASC-CARD/IVT cIAP-1 | – |
| GST-ASC-CARD/IVT cIAP-2 | – |

As shown in Table 7, the CARD domain of ASC, while self-associating, does not associate with several other CARD domain-containing proteins.

In order to determine the localization of ASC and ASC2, Cos-7 cells were seeded onto 12-well plates and transfected with 1.5 µg total fusion plasmid DNA (either) EGFP-ASC, EGFP-ASC2 or EGFP-ASC in combination with RFP-ASC2) (Clontech) using Lipofectamine plus (Life Technologies) 24 hours later. The next day cells were trypsinized and seeded onto 4- or 8-well chamber slides (LabTec) and fixed with 4% paraformaldehyde and mounted (Vectashield). Confocal laser scanning microscopy was then performed.

The microscopy results indicated that ASC, when expressed alone, was localized to characteristic "speckles." ASC2, when expressed alone, exhibited a diffuse pattern of cytoplasmic and nuclear localization. However, when expressed together, ASC and ASC2 co-localized in ASC speckles. Therefore, ASC is apparently able to recruit ASC2 into ASC "speckles." This co-localization is further evidence that ASC and ASC2 associate in vivo.

In order to determine the effect of ASC, ASC-CARD, ASC-PAAD and ASC2 on NFκB induction in response to TNFα, IL-1β, Nod1 or Cardiak, reporter assays were performed using the Dual-Luciferase assay system (Promega). In brief, HEK293N cells were seeded onto 24-well plates and transfected with 1 µg total plasmid DNA including 6 ng of pRL-TK and 150 ng pRL-NF-κB or pRL-p53 (all Promega) using SuperFect™ transfection reagent (Qiagen) 24 hours later. After culturing for 48 hours, cells were lysed in 100 µl passive lysis buffer (Promega) and frozen at –80° C. Subsequently, 5–10 µl of lysate were transferred to 96-well plates and analyzed using a Luminometer (Wallach, Perkin Elmer). If indicated, cells were treated with 10 ng TNF-α or IL-1β 6–8 hours prior to lysis. All experiments were performed in triplicate and repeated at least twice.

Figure 7A:
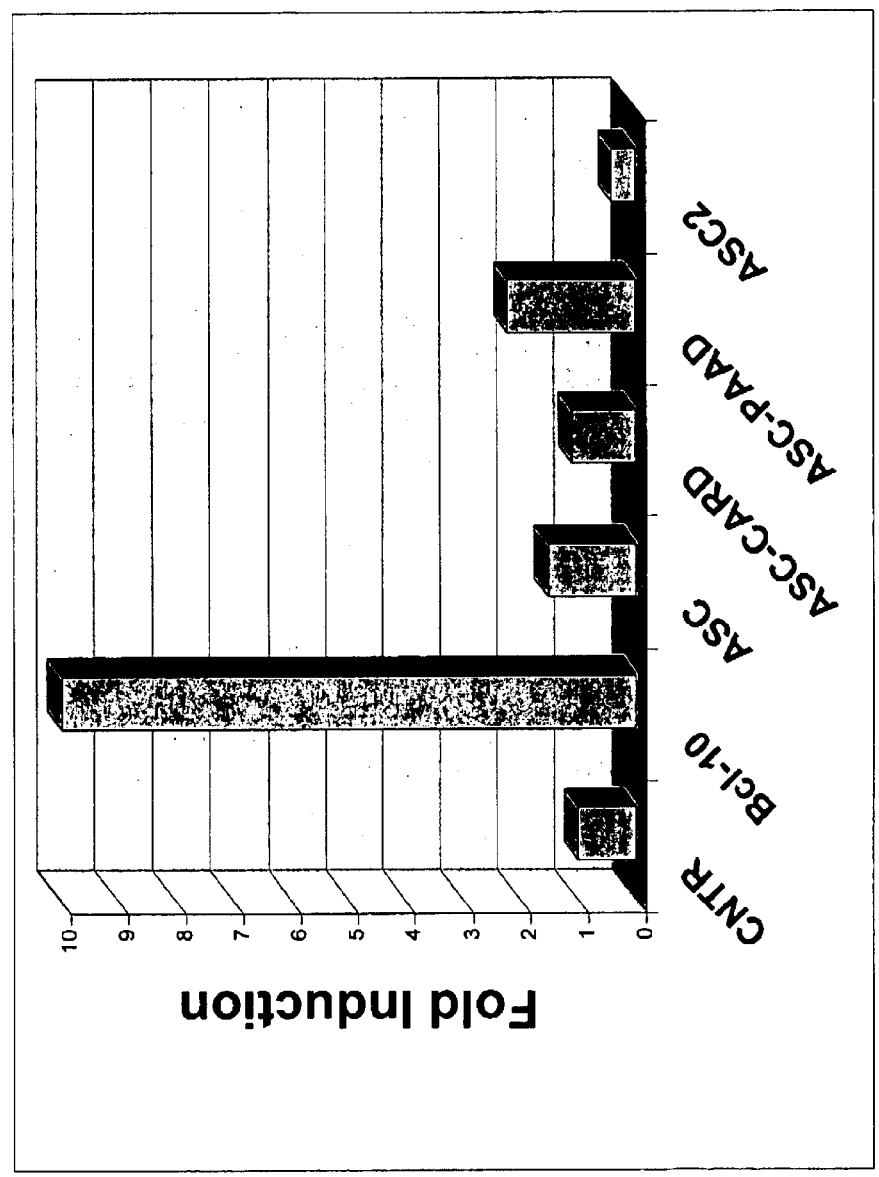
FIG. 7 shows a luciferase reporter assay in which NFκB transcriptional activity was determined in cells transfected with Bcl10 (A), contacted with TNFα (B), contacted with IL-1β (C), or transfected with Bcl10, Nod1 or Cardiak (D), and further transfected with either an empty vector (CNTR), or vectors expressing ASC, domains therefrom, or ASC2, as indicated.
Figure 7B:
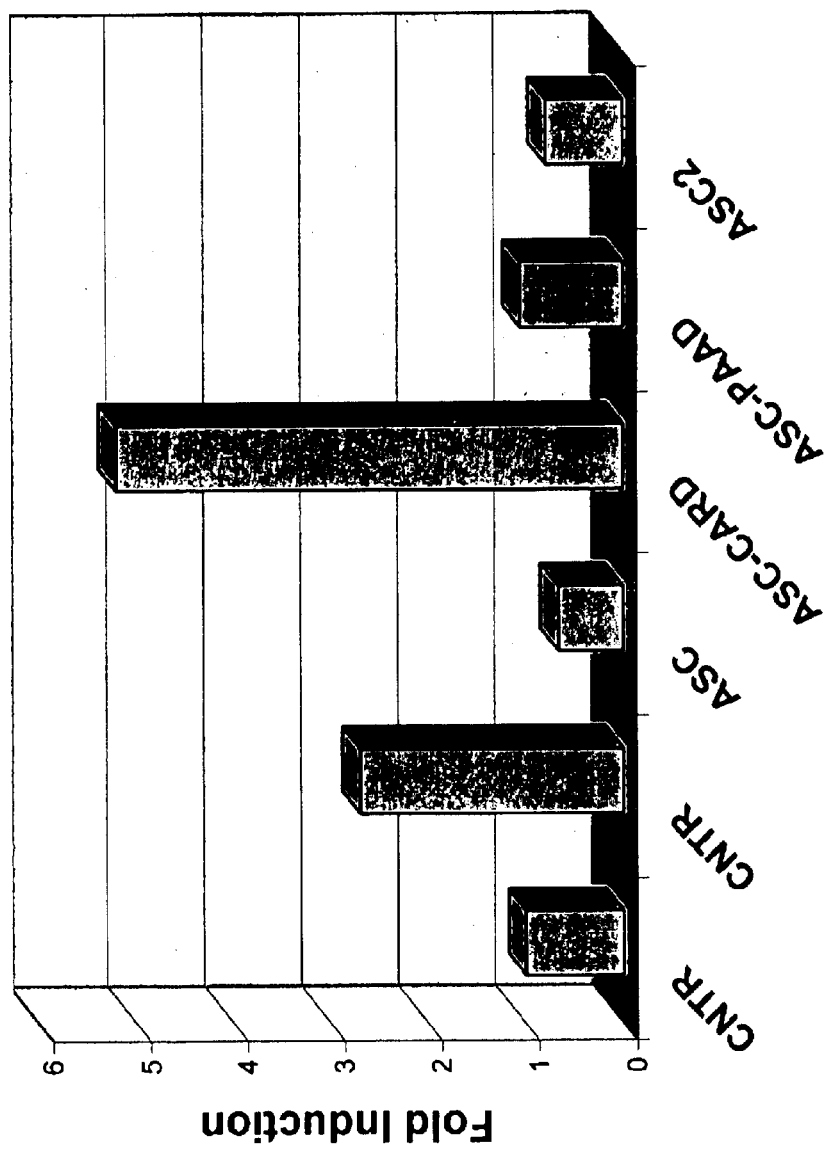
Figure 7C:
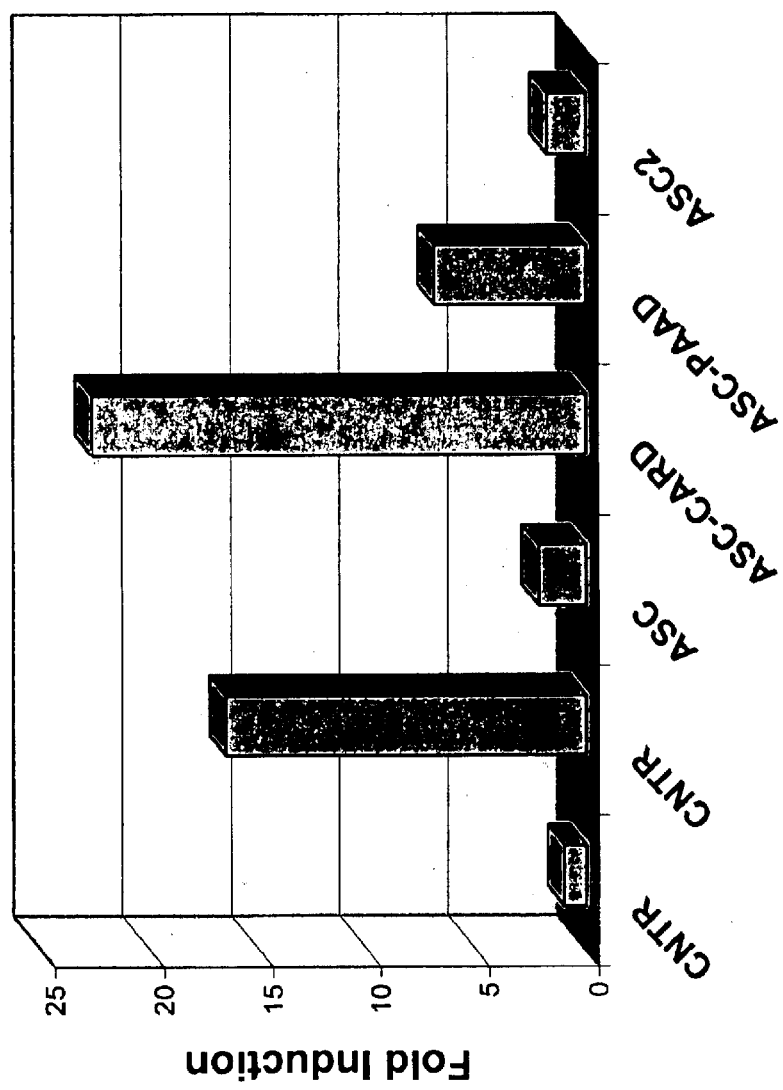
Figure 7D:
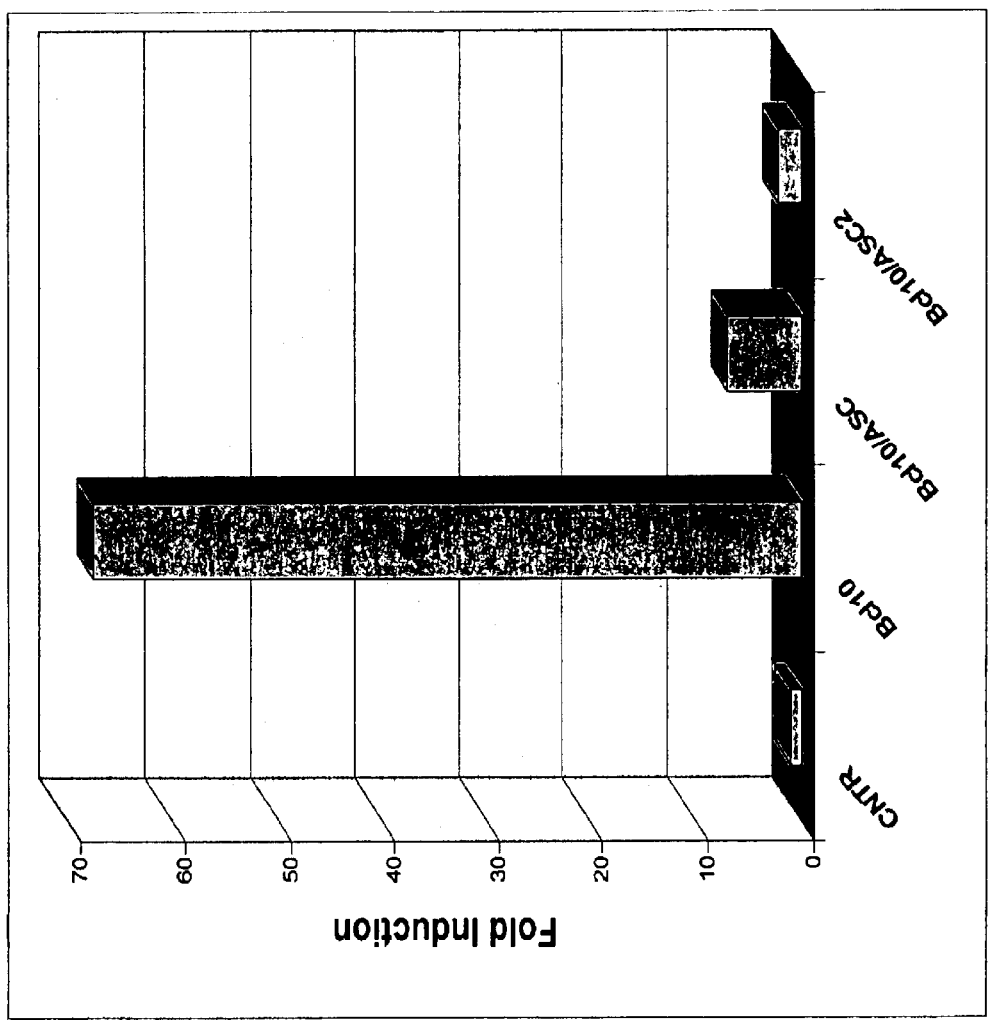
Figure 7E:
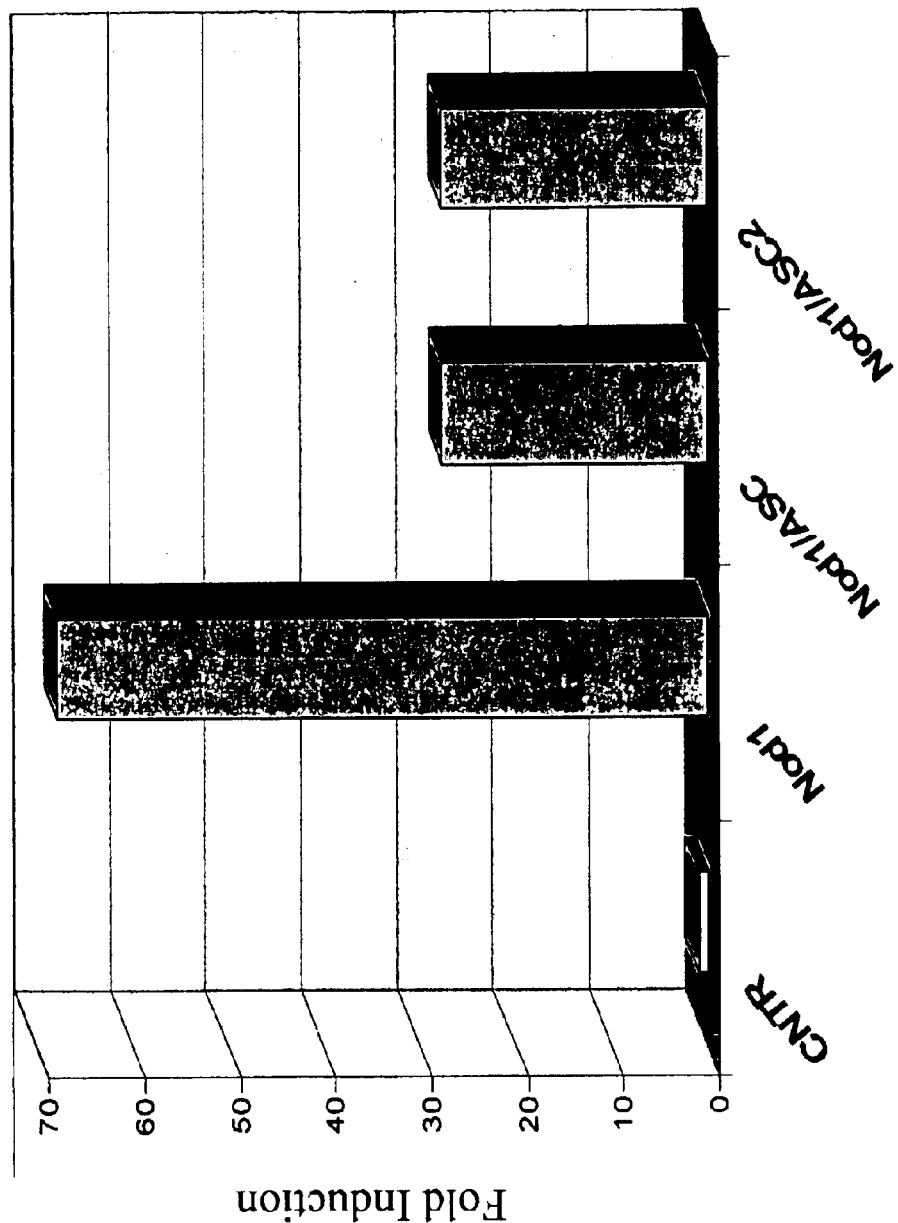
Figure 7F:
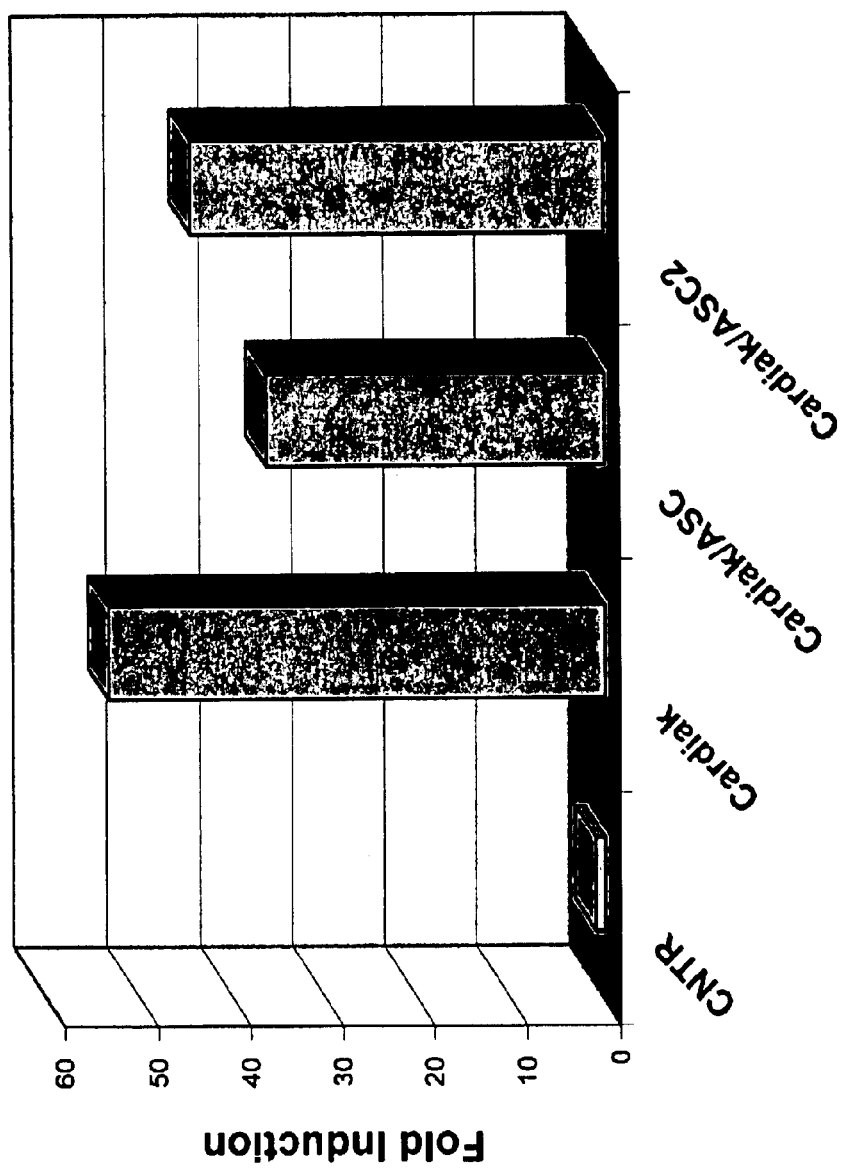

As shown in FIGS. 7A–7C, ASC, ASC2 and the PAAD domain of ASC are each able to inhibit NFκB induction by Bcl-10, TNFα and IL-1β. As shown in FIG. 7D, ASC and ASC2 also inhibited NFκB induction by Nod1 and, to a lesser extent, by Cardiak. In other experiments, the inhibition of TNFα-induced NFκB activation was shown to be dependent on the amount of either ASC or ASC2 transfected, and also to be specific for NFκB, as no inhibition of adriamycin-induced p53 activation by ASC was observed.

Figure 8:
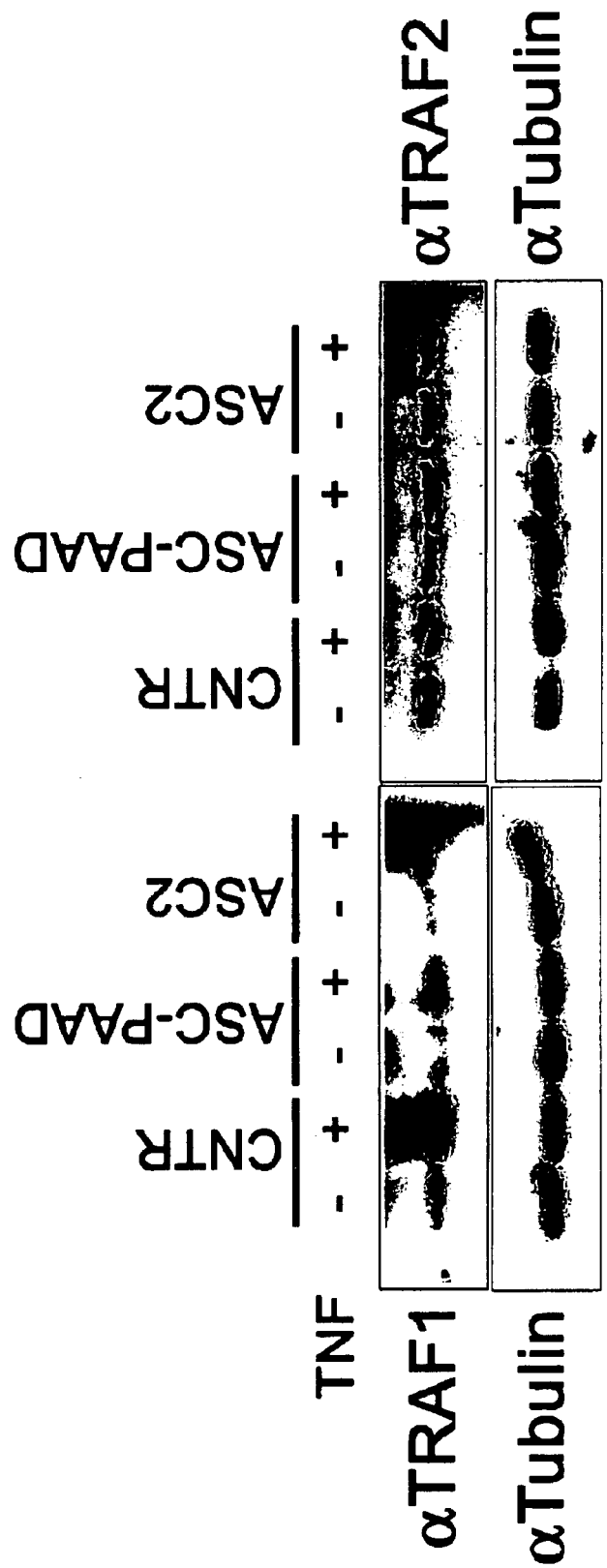
FIG. 8 shows an immunoblot in which the expression of TRAF1 and TRAF2 was examined in cells transfected with the indicated expression vectors and either stimulated with TNF or unstimulated. The expression of Tubulin was determined as a control.

Certain genes are induced by NFκB, including TRAF1 (Carpentier et a., FEBS Lett. 460:246–250 (1999). TNFα is a potent inducer of NFκB activation. In order to examine the effect of ASC-PAAD and ASC2 on TNFα-induced expression of the endogenous NFκB target gene TRAF1, HEK 293N cells were transiently transfected with expression plasmids for ASC-PAAD or ASC2, and either treated for 4 hours with TNFα or left untreated. Cleared lysates were immunoblotted with anti-TRAF1 or anti-TRAF2 antibodies. Equal loading was confirmed by re-blotting with an anti-Tubulin antibody. As shown in FIG. 8, treatment with TNF normally causes an increase in expression of TRAF1 but not TRAF2 protein (see lanes marked CNTR, compare − and + TNF). Expression of either ASC-PAAD or ASC2 decreased both basal and TNF-induced expression of TRAF1, without affecting expression of TRAF2. Because increased TRAF1 expression in response to TNF stimulation is mediated by NFκB activation, this result is consistent with the determination (see FIG. 7) that ASC-PAAD or ASC2 inhibit NFκB activation.

Active caspase-1 cleaves pro-IL-1β, resulting in the generation of bioactive IL-1β which is secreted from cells. In order to determine whether ASC or ASC2 affected caspase-1-induced pro-IL-1β processing, COS-7 cells and HEK293N cells were grown in 24 well plates (14 mm wells) and transfected with 1 μg plasmid DNA (Myc-tagged pro-caspase-1, pro-IL-1β (Lee et al., J. Biol. Chem. 276:34495–34500 (2001); Damiano et al., *Genomics* 75:77–83 (2001)), HA-tagged ASC and HA-tagged ASC2 in various combinations) using Lipofectamine plus (Gibco BRL, Grand Island, N.Y.) or Superfect (Qiagen, Valencia, Calif.) 24 hours later. After culturing for 36 hours at 37° C. and 5% $CO_2$ in Dulbecco's modified Eagle medium (DMEM) supplemented with either 20% or 10% heat-inactivated fetal bovine serum (FBS), 1 mM L-glutamine, and antibiotics, supernatants were collected, volume adjusted and stored at −80° C. or used immediately for an IL-1β ELISA assay (R&D Systems, Minneapolis, Minn.) according to the manufacturer's instructions. Cells were washed in PBS, lysed in isotonic lysis buffer, and directly analyzed by immunoblotting using anti-Myc and anti-HA antibodies. Results from one representative experiment of at least three experiments are shown in FIG. 9.

Figure 9:
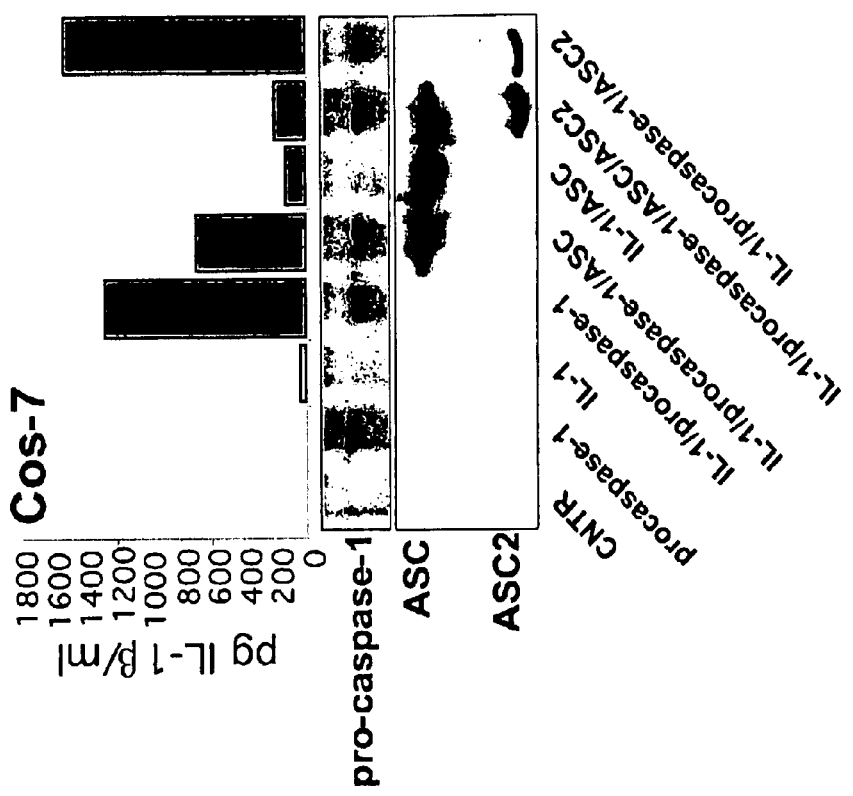
FIG. 9 shows the amount of interleukin-1β secreted from 293N or Cos-7 cells transfected with the indicated expression vectors.
Figure 9:
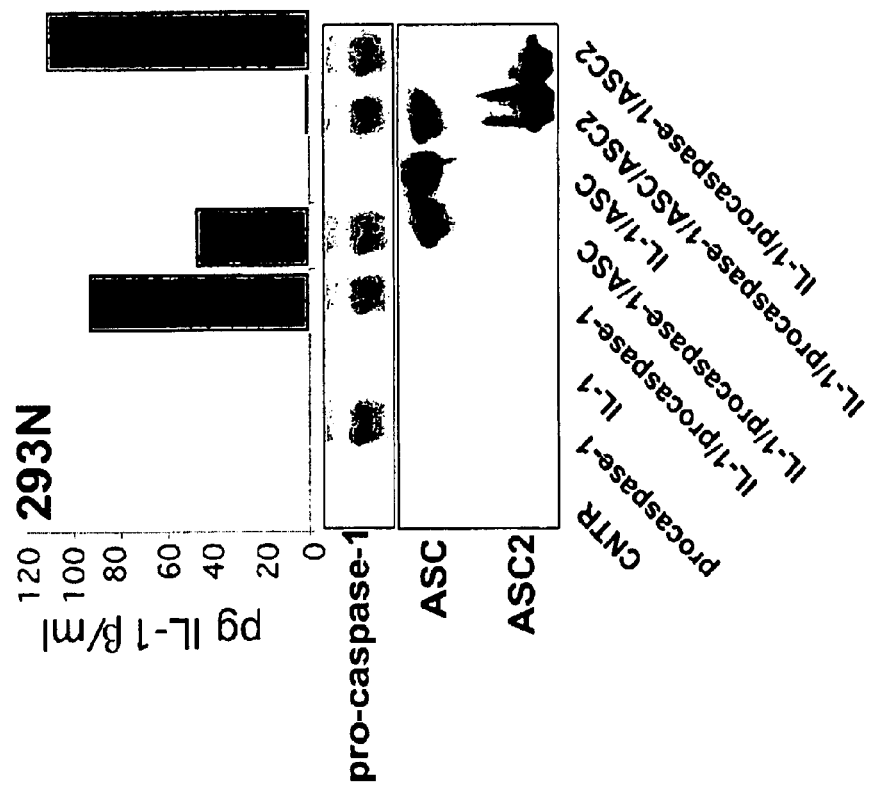

As shown in FIG. 9, co-expression of procaspase-1 and pro-IL-1β ("IL-1") resulted in a high level of secretion of active IL-1β. This IL-1β secretion was inhibited by about 50% by co-expression of ASC, and almost completely inhibited by co-expression of both ASC and ASC2, but was not inhibited by expression of ASC2 alone. Therefore, ASC interferes with activation of a CARD-containing caspase, caspase-1. The association between Cardiak and ASC (see Table 6) may be involved in the inhibition of caspase-1 activation.

Figure 10A:
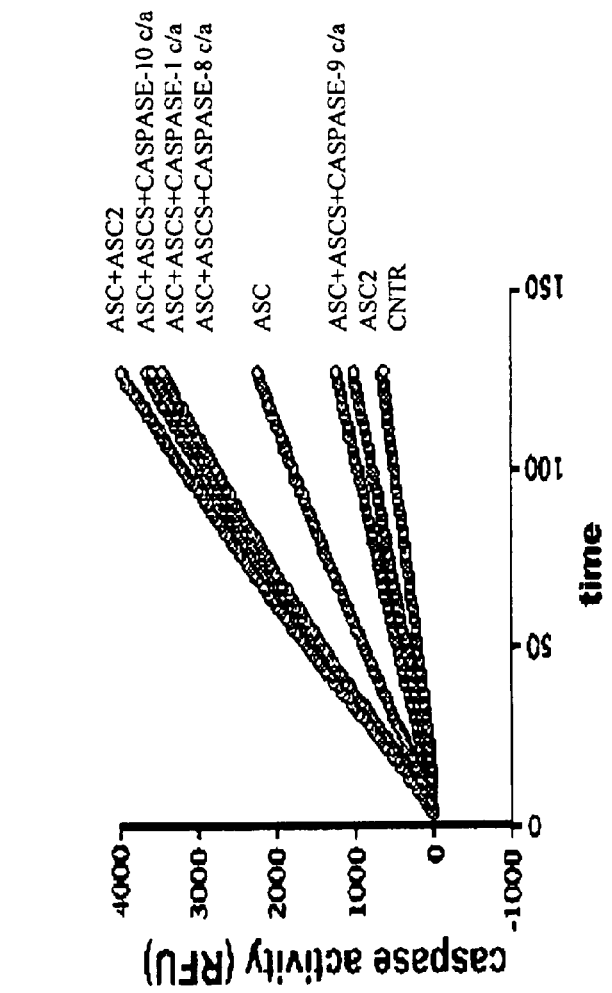
FIGS. 10A–10B show shows caspase activity, indicated by the cleavage of the fluorogenic substrate AC-DEVD-AFC over time in cells transfected with the indicated expression vectors. c/a indicates that the caspase is an active site mutant.
Figure 10B:
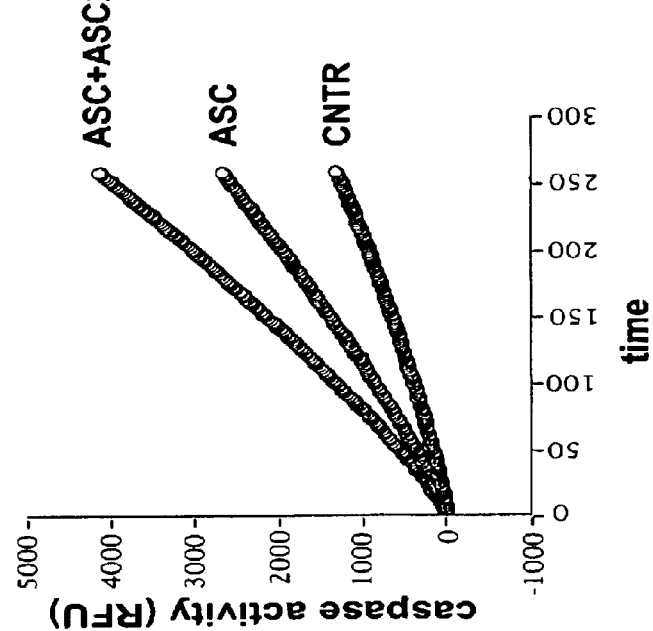

Caspases that cleave the tetrapeptide substrate DEVD-AFC are directly involved in apoptosis, and thus DEDVase activity serves as a surrogate marker of apoptosis. In order to determine the effect of ASC and ASC2 on caspase activation, HEK293N cells were transiently transfected with expression plasmids for ASC; or ASC in combination with ASC2 alone or further in combination with active site mutants of caspase-1, caspase-8, caspase-9 or caspase-10. Transfected HEK293N cells were directly lysed in caspase lysis buffer (10 mM HEPES (pH 7.4), 25 mM NaCl, 0.25% Triton X-100, and 1 mM EDTA), normalized for protein content, and protease activity was measured continuously by monitoring the release of fluorigenic Ac-DEVD-AFC (Bachem, Philadelphia, Pa.) at 37° C. As shown in FIG. 10, caspase activity was increased by expression of ASC (A and B), and further increased by expression of ASC and ASC2 in combination (A and B). Caspase activity was only slightly increased by expression of ASC2 alone (B). Expression of catalytic site mutants of caspase-1, caspase-8 or caspase-10 (c/a) only slightly decreased ASC-ASC2-mediated caspase activity (B), whereas expression of a catalytic site mutant of caspase-9 (c/a) strongly inhibited ASC+ASC2-mediated caspase activity (B). Therefore, ASC and ASC2 activate a caspase-9-dependent pathway for apoptosis.

Although the invention has been described with reference to the examples above, it should be understood that various modifications can be made without departing from the spirit of the invention. Accordingly, the invention is limited only by the following claims.

We claim:

1. An isolated nucleic acid molecule encoding a PAN6 polypeptide, comprising:
   (a) a nucleic acid molecule encoding a polypeptide comprising the amino acid sequence set forth as SEQ ID NO: 24; or
   (b) a nucleic acid molecule that hybridizes to the nucleic acid molecule of (a) under highly stringent conditions, wherein the nucleic acid of (a) or (b) encodes a PAAD domain-containing polypeptide having NFκB activation inhibiting activity.

2. The nucleic acid molecule of claim 1, comprising a nucleotide sequence set forth as SEQ ID NO:23.

3. A vector containing the nucleic acid molecule of claim 1.

4. A recombinant cell containing the nucleic acid molecule of claim 1.

* * * * *